(12) United States Patent
Swenson et al.

(10) Patent No.: US 11,193,119 B2
(45) Date of Patent: Dec. 7, 2021

(54) DEVICES AND METHODS FOR NUCLEIC ACID EXTRACTION

(71) Applicant: Visby Medical, Inc., San Jose, CA (US)

(72) Inventors: David D. Swenson, Santa Clara, CA (US); Gregory C. Loney, Los Altos, CA (US); Valeria Revilla, East Palo Alto, CA (US); Adrienne C. Lam, Fremont, CA (US); Helen Huang, San Pablo, CA (US); Colin Kelly, San Francisco, CA (US); Victor Briones, Gilroy, CA (US); Brian Ciopyk, Pleasanton, CA (US); Boris Andreyev, Foster City, CA (US); Adam De La Zerda, Palo Alto, CA (US); Keith Moravick, Mountain View, CA (US); Jesus Ching, Saratoga, CA (US); Jennifer Albrecht, Sunnyvale, CA (US); Ryan Cena, San Jose, CA (US); Edward Biba, Santa Clara, CA (US); Jonathan Hong, San Jose, CA (US)

(73) Assignee: Visby Medical, Inc., San Jose, CA (US)

( * ) Notice: Subject to any disclaimer, the term of this patent is extended or adjusted under 35 U.S.C. 154(b) by 350 days.

(21) Appl. No.: 16/186,240

(22) Filed: Nov. 9, 2018

(65) Prior Publication Data

US 2019/0136226 A1    May 9, 2019

Related U.S. Application Data

(63) Continuation of application No. PCT/US2017/032035, filed on May 10, 2017.
(Continued)

(51) Int. Cl.
*C12Q 1/6806* (2018.01)
*C12N 15/10* (2006.01)
(Continued)

(52) U.S. Cl.
CPC .... *C12N 15/1017* (2013.01); *B01L 3/502715* (2013.01); *C12Q 1/00* (2013.01);
(Continued)

(58) Field of Classification Search
None
See application file for complete search history.

(56) References Cited

U.S. PATENT DOCUMENTS 3,697,227 A    10/1972  Goldstein et al.
4,710,355 A    12/1987  Ushikubo et al.
(Continued)

FOREIGN PATENT DOCUMENTS

CN    101538567 A    9/2009
CN    105239164 A    1/2016
(Continued)

OTHER PUBLICATIONS

Brunklaus, S. et al., Fast nucleic acid amplification for integration in point-of-care applications, Electrophoresis, 2012, vol. 33, pp. 3222-3228.
(Continued)

*Primary Examiner* — Robert T. Crow
(74) *Attorney, Agent, or Firm* — Cooley LLP

(57) ABSTRACT

Disclosed herein are methods and devices for preparing a sample of nucleic acid molecules from a biological sample. The methods and devices may perform similarly to or better than standard sample preparation methods. The nucleic acid molecules prepared using the methods and devices provided
(Continued)

herein may be utilized for downstream applications, including polymerase chain reaction (PCR).

17 Claims, 22 Drawing Sheets

Related U.S. Application Data

(60) Provisional application No. 62/334,982, filed on May 11, 2016, provisional application No. 62/356,451, filed on Jun. 29, 2016, provisional application No. 62/356,596, filed on Jun. 30, 2016.

(51) Int. Cl.
*C12Q 1/00* (2006.01)
*G01N 33/48* (2006.01)
*B01L 3/00* (2006.01)
*C12Q 1/37* (2006.01)
*C12Q 1/686* (2018.01)

(52) U.S. Cl.
CPC ............. *C12Q 1/37* (2013.01); *C12Q 1/6806* (2013.01); *C12Q 1/686* (2013.01); *G01N 33/48* (2013.01); *B01L 2300/0636* (2013.01); *B01L 2300/0681* (2013.01); *B01L 2300/1805* (2013.01); *C12Y 304/21064* (2013.01)

(56) References Cited

U.S. PATENT DOCUMENTS

| | | | |
|---|---|---|---|
| 4,789,630 A | 12/1988 | Bloch et al. | |
| 4,889,692 A | 12/1989 | Holtzman et al. | |
| RE33,858 E | 3/1992 | Gropper et al. | |
| 5,164,159 A | 11/1992 | Hayashi et al. | |
| 5,229,297 A | 7/1993 | Schnipelsky et al. | |
| 5,270,183 A | 12/1993 | Corbett et al. | |
| 5,273,905 A | 12/1993 | Muller et al. | |
| 5,405,585 A | 4/1995 | Coassin et al. | |
| 5,429,807 A | 7/1995 | Matson et al. | |
| 5,498,392 A | 3/1996 | Wilding et al. | |
| 5,631,165 A | 5/1997 | Chupp et al. | |
| 5,633,168 A | 5/1997 | Glasscock et al. | |
| 5,660,993 A | 8/1997 | Cathey et al. | |
| 5,726,026 A | 3/1998 | Wilding et al. | |
| 5,773,234 A | 6/1998 | Pronovost et al. | |
| 5,882,903 A | 3/1999 | Andrevski et al. | |
| 5,922,591 A | 7/1999 | Anderson et al. | |
| 5,952,664 A | 9/1999 | Wake et al. | |
| 5,976,470 A | 11/1999 | Maiefski et al. | |
| 6,039,924 A | 3/2000 | Horn et al. | |
| 6,126,804 A | 10/2000 | Andresen et al. | |
| 6,146,591 A | 11/2000 | Miller et al. | |
| 6,153,425 A | 11/2000 | Kozwich et al. | |
| 6,168,760 B1 | 1/2001 | Horn et al. | |
| 6,235,479 B1 | 5/2001 | Rogers | |
| 6,261,431 B1 | 7/2001 | Mathies et al. | |
| 6,303,081 B1 | 10/2001 | Mink et al. | |
| 6,313,471 B1 | 11/2001 | Giebeler et al. | |
| 6,365,378 B1 | 4/2002 | Hirota et al. | |
| 6,369,893 B1 | 4/2002 | Christel et al. | |
| 6,374,684 B1 | 4/2002 | Dority et al. | |
| 6,416,718 B1 | 7/2002 | Maiefski et al. | |
| 6,426,215 B1 | 7/2002 | Sandell et al. | |
| 6,514,750 B2 | 2/2003 | Bordenkircher et al. | |
| 6,610,499 B1 | 8/2003 | Fulwyler et al. | |
| 6,645,758 B1 | 11/2003 | Schnipelsky et al. | |
| 6,649,378 B1 | 11/2003 | Kozwich et al. | |
| 6,656,744 B2 | 12/2003 | Pronovost et al. | |
| 6,677,151 B2 | 1/2004 | Sandell et al. | |
| 6,680,617 B2 | 1/2004 | Moreland et al. | |
| 6,767,512 B1 | 7/2004 | Lurz et al. | |
| 6,780,380 B2 | 8/2004 | Hunnell et al. | |
| 6,780,617 B2 | 8/2004 | Chen et al. | |
| 6,781,056 B1 | 8/2004 | O'Rourke et al. | |
| 6,813,568 B2 | 11/2004 | Powell et al. | |
| 6,821,771 B2 | 11/2004 | Festoc et al. | |
| 6,875,403 B2 | 4/2005 | Liu et al. | |
| 6,893,879 B2 | 5/2005 | Petersen et al. | |
| 6,901,217 B2 | 5/2005 | Gamboa et al. | |
| 6,911,181 B1 | 6/2005 | McNeil et al. | |
| 6,964,862 B2 | 11/2005 | Chen et al. | |
| 6,990,290 B2 | 1/2006 | Kylberg et al. | |
| 7,041,481 B2 | 5/2006 | Anderson et al. | |
| 7,144,742 B2 | 12/2006 | Boehringer et al. | |
| 7,179,639 B2 | 2/2007 | Pottathil et al. | |
| 7,189,522 B2 | 3/2007 | Esfandiari et al. | |
| 7,192,721 B1 | 3/2007 | Esfandiari et al. | |
| 7,235,216 B2 | 6/2007 | Kiselev et al. | |
| 7,297,313 B1 | 11/2007 | Northrup et al. | |
| 7,341,697 B2 | 3/2008 | Takeuchi et al. | |
| 7,377,291 B2 | 5/2008 | Moon et al. | |
| 7,378,285 B2 | 5/2008 | Lambotte et al. | |
| 7,384,782 B2 | 6/2008 | Nakatani et al. | |
| 7,416,892 B2 | 8/2008 | Battrell et al. | |
| 7,438,852 B2 | 10/2008 | Tung et al. | |
| 7,459,302 B2 | 12/2008 | Reid et al. | |
| 7,491,551 B2 | 2/2009 | Boehringer et al. | |
| 7,517,495 B2 | 4/2009 | Wu et al. | |
| 7,544,324 B2 | 6/2009 | Tung et al. | |
| 7,550,112 B2 | 6/2009 | Gou et al. | |
| 7,553,675 B2 | 6/2009 | Jerome et al. | |
| 7,569,382 B2 | 8/2009 | Li et al. | |
| 7,579,172 B2 | 8/2009 | Cho et al. | |
| 7,592,139 B2 | 9/2009 | West et al. | |
| 7,632,687 B2 | 12/2009 | Gokhan et al. | |
| 7,648,835 B2 | 1/2010 | Breidford et al. | |
| 7,682,801 B2 | 3/2010 | Esfandiari et al. | |
| 7,691,644 B2 | 4/2010 | Lambotte et al. | |
| 7,705,339 B2 | 4/2010 | Smith et al. | |
| 7,709,250 B2 | 5/2010 | Corbett et al. | |
| 7,754,452 B2 | 7/2010 | Kim et al. | |
| 7,767,439 B2 | 8/2010 | Oh et al. | |
| 7,794,656 B2 | 9/2010 | Liang et al. | |
| 7,799,521 B2 | 9/2010 | Chen et al. | |
| 7,837,939 B2 | 11/2010 | Tung et al. | |
| 7,858,396 B2 | 12/2010 | Corstjens et al. | |
| 7,871,568 B2 | 1/2011 | Liang et al. | |
| 7,879,293 B2 | 2/2011 | Niedbala et al. | |
| 7,914,986 B2 | 3/2011 | Nunn et al. | |
| 7,915,013 B2 | 3/2011 | Cho et al. | |
| 7,935,504 B2 | 5/2011 | Chen et al. | |
| 7,943,348 B2 | 5/2011 | Cho et al. | |
| 7,959,877 B2 | 6/2011 | Esfandiari et al. | |
| 7,985,716 B2 | 7/2011 | Yershov et al. | |
| 7,988,915 B2 | 8/2011 | Lee et al. | |
| 7,998,757 B2 | 8/2011 | Darrigrand et al. | |
| 8,008,046 B2 | 8/2011 | Maltezos et al. | |
| 8,008,080 B2 | 8/2011 | Tokhtuev et al. | |
| 8,012,427 B2 | 9/2011 | Bommarito et al. | |
| 8,018,593 B2 | 9/2011 | Tan et al. | |
| 8,048,386 B2 | 11/2011 | Dority et al. | |
| 8,062,883 B2 | 11/2011 | Woudenberg et al. | |
| 8,075,854 B2 | 12/2011 | Yang et al. | |
| 8,076,129 B2 | 12/2011 | Hanafusa et al. | |
| 8,088,616 B2 | 1/2012 | Handique et al. | |
| 8,110,148 B2 | 2/2012 | Ball et al. | |
| 8,110,392 B2 | 2/2012 | Battrell et al. | |
| 8,133,671 B2 | 3/2012 | Williams et al. | |
| 8,133,703 B2 | 3/2012 | Ching et al. | |
| 8,148,116 B2 | 4/2012 | Chen et al. | |
| 8,163,489 B2 | 4/2012 | Murray et al. | |
| 8,163,535 B2 | 4/2012 | Reed et al. | |
| 8,169,610 B2 | 5/2012 | Oldham et al. | |
| 8,173,077 B2 | 5/2012 | Korampally et al. | |
| 8,187,557 B2 | 5/2012 | Van et al. | |
| 8,198,074 B2 | 6/2012 | Moriwaki et al. | |
| 8,216,832 B2 | 7/2012 | Battrell et al. | |
| 8,222,023 B2 | 7/2012 | Battrell et al. | |
| 8,231,844 B2 | 7/2012 | Gorfinkel et al. | |
| 8,232,091 B2 | 7/2012 | Maltezos et al. | |
| 8,232,094 B2 | 7/2012 | Hasson et al. | |
| 8,247,221 B2 | 8/2012 | Fawcett et al. | |

(56) References Cited

U.S. PATENT DOCUMENTS

| | | |
|---|---|---|
| 8,263,392 B2 | 9/2012 | Gale et al. |
| 8,277,763 B2 | 10/2012 | Steinmann et al. |
| 8,278,091 B2 | 10/2012 | Rutter et al. |
| 8,298,763 B2 | 10/2012 | Regan et al. |
| 8,323,583 B2 | 12/2012 | Gou et al. |
| 8,329,453 B2 | 12/2012 | Battrell et al. |
| 8,343,442 B2 | 1/2013 | McBride et al. |
| 8,343,754 B2 | 1/2013 | Wittwer et al. |
| 8,357,490 B2 | 1/2013 | Froehlich et al. |
| 8,372,340 B2 | 2/2013 | Bird et al. |
| 8,389,960 B2 | 3/2013 | Pieprzyk et al. |
| 8,394,322 B2 | 3/2013 | Windeyer et al. |
| 8,394,608 B2 | 3/2013 | Ririe et al. |
| 8,394,626 B2 | 3/2013 | Ramsey et al. |
| 8,426,134 B2 | 4/2013 | Piepenburg et al. |
| 8,431,413 B2 | 4/2013 | Dority et al. |
| 8,435,461 B2 | 5/2013 | Kirby et al. |
| 8,448,824 B2 | 5/2013 | Diperna et al. |
| 8,492,136 B2 | 7/2013 | Carlisle et al. |
| 8,507,259 B2 | 8/2013 | Esfandiari et al. |
| 8,557,518 B2 | 10/2013 | Jovanovich et al. |
| 8,580,575 B2 | 11/2013 | Hanafusa et al. |
| 8,597,937 B2 | 12/2013 | Ward et al. |
| 8,603,835 B2 | 12/2013 | Esfandiari et al. |
| 8,617,486 B2 | 12/2013 | Kirby et al. |
| 8,629,264 B2 | 1/2014 | Reed et al. |
| 8,637,250 B2 | 1/2014 | Jenison et al. |
| 8,663,976 B2 | 3/2014 | Chung et al. |
| 8,673,238 B2 | 3/2014 | Dority et al. |
| 8,673,239 B2 | 3/2014 | Niedbala et al. |
| 8,691,561 B2 | 4/2014 | Igata et al. |
| 8,722,426 B2 | 5/2014 | Lambotte et al. |
| 8,728,765 B2 | 5/2014 | Ching et al. |
| 8,735,103 B2 | 5/2014 | Chung et al. |
| 8,758,701 B2 | 6/2014 | Van et al. |
| 8,765,367 B2 | 7/2014 | Breidenthal et al. |
| 8,765,454 B2 | 7/2014 | Zhou et al. |
| 8,772,017 B2 | 7/2014 | Battrell et al. |
| 8,795,592 B2 | 8/2014 | Eiriksson et al. |
| 8,859,199 B2 | 10/2014 | Hellyer et al. |
| 8,865,458 B2 | 10/2014 | Ramsey et al. |
| 8,871,155 B2 | 10/2014 | Wu et al. |
| 8,877,450 B2 | 11/2014 | Esfandiari et al. |
| 8,894,946 B2 | 11/2014 | Nielsen et al. |
| 8,895,255 B1 | 11/2014 | Goldberg et al. |
| 8,900,828 B2 | 12/2014 | Smith et al. |
| 8,900,853 B2 | 12/2014 | Verhaar et al. |
| 8,911,941 B2 | 12/2014 | Michlitsch et al. |
| 8,911,949 B2 | 12/2014 | Bertrand et al. |
| 8,916,375 B2 | 12/2014 | Landers et al. |
| 8,945,843 B2 | 2/2015 | Alvino et al. |
| 8,975,027 B2 | 3/2015 | Gale et al. |
| 8,980,177 B2 | 3/2015 | Carlisle et al. |
| 8,980,561 B1 | 3/2015 | Cai et al. |
| 8,986,927 B2 | 3/2015 | Lee et al. |
| 8,992,854 B2 | 3/2015 | Brewster et al. |
| 9,011,770 B2 | 4/2015 | Wu et al. |
| 9,012,236 B2 | 4/2015 | Jovanovich et al. |
| 9,023,639 B2 | 5/2015 | Kim et al. |
| 9,044,729 B2 | 6/2015 | Rengifo et al. |
| 9,150,907 B2 | 10/2015 | Shaikh et al. |
| 9,207,236 B2 | 12/2015 | Cary |
| 9,207,241 B2 | 12/2015 | Lambotte et al. |
| 9,238,833 B2 | 1/2016 | Chen et al. |
| 9,243,288 B2 | 1/2016 | Ness et al. |
| 9,260,750 B2 | 2/2016 | Hillebrand et al. |
| 9,387,478 B2 | 7/2016 | Bergstedt et al. |
| 9,428,781 B2 | 8/2016 | Cai et al. |
| 9,453,255 B2 | 9/2016 | Ozawa et al. |
| 9,469,871 B2 | 10/2016 | Bearinger et al. |
| 9,475,049 B2 | 10/2016 | Siciliano et al. |
| D776,290 S | 1/2017 | Wan et al. |
| 9,623,415 B2 | 4/2017 | Andreyev et al. |
| 9,725,754 B2 | 8/2017 | Boyle et al. |
| 9,752,182 B2 | 9/2017 | Collier et al. |
| 10,040,069 B2 | 8/2018 | Moore et al. |
| 10,173,182 B2 | 1/2019 | Tachibana et al. |
| 10,233,483 B2 | 3/2019 | Talebpour et al. |
| 10,603,664 B2 | 3/2020 | Khattak |
| 2001/0055799 A1 | 12/2001 | Baunoch et al. |
| 2002/0086417 A1 | 7/2002 | Chen et al. |
| 2003/0027203 A1 | 2/2003 | Fields |
| 2003/0027244 A1 | 2/2003 | Colston et al. |
| 2004/0018502 A1 | 1/2004 | Makino et al. |
| 2004/0110141 A1 | 6/2004 | Pusey et al. |
| 2004/0209331 A1 | 10/2004 | Ririe et al. |
| 2004/0224317 A1 | 11/2004 | Kordunsky et al. |
| 2004/0251426 A1 | 12/2004 | Birk et al. |
| 2005/0019875 A1 | 1/2005 | Chen et al. |
| 2005/0064598 A1 | 3/2005 | Yuan et al. |
| 2005/0100946 A1 | 5/2005 | Lipshutz et al. |
| 2005/0142036 A1 | 6/2005 | Kim et al. |
| 2005/0194316 A1 | 9/2005 | Pourahmadi et al. |
| 2005/0227275 A1 | 10/2005 | Jung et al. |
| 2006/0001689 A1 | 1/2006 | Ahne et al. |
| 2006/0088931 A1 | 4/2006 | Ririe et al. |
| 2006/0127924 A1 | 6/2006 | Hellyer et al. |
| 2006/0154341 A1 | 7/2006 | Chen et al. |
| 2006/0160205 A1 | 7/2006 | Blackburn et al. |
| 2006/0177841 A1 | 8/2006 | Wangh et al. |
| 2006/0246493 A1 | 11/2006 | Jensen et al. |
| 2006/0258012 A1 | 11/2006 | Yang et al. |
| 2007/0026391 A1 | 2/2007 | Stoughton et al. |
| 2007/0036691 A1 | 2/2007 | Lin et al. |
| 2007/0042427 A1 | 2/2007 | Gerdes et al. |
| 2007/0154922 A1 | 7/2007 | Collier et al. |
| 2007/0277251 A1 | 11/2007 | Wartiovaara et al. |
| 2007/0284360 A1 | 12/2007 | Santoruvo et al. |
| 2007/0292941 A1 | 12/2007 | Handique et al. |
| 2008/0026451 A1 | 1/2008 | Braman et al. |
| 2008/0038737 A1 | 2/2008 | Smith et al. |
| 2008/0043235 A1 | 2/2008 | Oldham et al. |
| 2008/0050735 A1 | 2/2008 | Pushnova et al. |
| 2008/0057572 A1 | 3/2008 | Petersen et al. |
| 2008/0113391 A1 | 5/2008 | Gibbons et al. |
| 2008/0145852 A1 | 6/2008 | Shuber et al. |
| 2008/0153078 A1 | 6/2008 | Braman et al. |
| 2008/0220468 A1 | 9/2008 | Windeyer et al. |
| 2008/0274513 A1 | 11/2008 | Shenderov et al. |
| 2008/0280285 A1 | 11/2008 | Chen et al. |
| 2009/0029422 A1 | 1/2009 | Hanafusa et al. |
| 2009/0042256 A1 | 2/2009 | Hanafusa et al. |
| 2009/0130745 A1 | 5/2009 | Williams et al. |
| 2009/0186344 A1 | 7/2009 | Farinas |
| 2009/0215072 A1 | 8/2009 | McDevitt et al. |
| 2009/0325276 A1 | 12/2009 | Battrell et al. |
| 2010/0003683 A1 | 1/2010 | Sarofim et al. |
| 2010/0025242 A1 | 2/2010 | Pamula |
| 2010/0113762 A1 | 5/2010 | Ball et al. |
| 2010/0173393 A1 | 7/2010 | Handique et al. |
| 2010/0210038 A1 | 8/2010 | Blatt et al. |
| 2010/0291588 A1 | 11/2010 | McDevitt et al. |
| 2010/0297640 A1 | 11/2010 | Kumar et al. |
| 2011/0020876 A1 | 1/2011 | Wilding et al. |
| 2011/0039303 A1 | 2/2011 | Jovanovich et al. |
| 2011/0160090 A1 | 6/2011 | Cary |
| 2011/0203688 A1 | 8/2011 | Reed et al. |
| 2011/0207121 A1 | 8/2011 | Chen et al. |
| 2011/0211331 A1 | 9/2011 | Alkjaer et al. |
| 2011/0227551 A1 | 9/2011 | Black et al. |
| 2011/0253224 A1 | 10/2011 | Linder et al. |
| 2011/0269191 A1 | 11/2011 | Belgrader et al. |
| 2011/0275055 A1 | 11/2011 | Conner |
| 2011/0300545 A1 | 12/2011 | Cano et al. |
| 2011/0312666 A1 | 12/2011 | Azimi et al. |
| 2011/0312787 A1 | 12/2011 | Silverbrook et al. |
| 2011/0312793 A1 | 12/2011 | Azimi et al. |
| 2011/0312841 A1 | 12/2011 | Silverbrook et al. |
| 2011/0313148 A1 | 12/2011 | Christ et al. |
| 2012/0021454 A1 | 1/2012 | Bikker et al. |
| 2012/0064534 A1 | 3/2012 | Pipper et al. |
| 2012/0070878 A1 | 3/2012 | Fink et al. |
| 2012/0088294 A1 | 4/2012 | Sun et al. |
| 2012/0115738 A1 | 5/2012 | Zhou et al. |

(56) References Cited

U.S. PATENT DOCUMENTS

| | | |
|---|---|---|
| 2012/0130061 A1 | 5/2012 | Himmelreich et al. |
| 2012/0135511 A1 | 5/2012 | Battrell et al. |
| 2012/0141337 A1 | 6/2012 | Maltezos et al. |
| 2012/0237939 A1 | 9/2012 | Reed et al. |
| 2012/0264202 A1 | 10/2012 | Walker et al. |
| 2012/0276532 A1 | 11/2012 | Chen et al. |
| 2012/0282684 A1 | 11/2012 | Fritchie et al. |
| 2012/0288897 A1 | 11/2012 | Ching et al. |
| 2013/0040296 A1 | 2/2013 | Tulp et al. |
| 2013/0053255 A1 | 2/2013 | Vangbo et al. |
| 2013/0059290 A1 | 3/2013 | Armes |
| 2013/0078736 A1 | 3/2013 | Grover et al. |
| 2013/0115712 A1 | 5/2013 | Yu et al. |
| 2013/0118900 A1 | 5/2013 | Reimitz et al. |
| 2013/0149710 A1 | 6/2013 | Yoon et al. |
| 2013/0171640 A1 | 7/2013 | Kwon et al. |
| 2013/0210080 A1 | 8/2013 | Rajagopal et al. |
| 2013/0217026 A1 | 8/2013 | Egan et al. |
| 2013/0220781 A1 | 8/2013 | Czarnecki et al. |
| 2013/0225801 A1 | 8/2013 | Christoffel |
| 2014/0045191 A1 | 2/2014 | DeJohn et al. |
| 2014/0051159 A1 | 2/2014 | Bergstedt et al. |
| 2014/0073013 A1 | 3/2014 | Gorman et al. |
| 2014/0087359 A1 | 3/2014 | Njoroge et al. |
| 2014/0098252 A1 | 4/2014 | Chang et al. |
| 2014/0120539 A1 | 5/2014 | Tanner et al. |
| 2014/0199685 A1 | 7/2014 | Lambotte et al. |
| 2014/0274770 A1 | 9/2014 | Pack |
| 2014/0329301 A1 | 11/2014 | Handique |
| 2015/0031087 A1 | 1/2015 | Nagai et al. |
| 2015/0176057 A1 | 6/2015 | Smith et al. |
| 2015/0182966 A1 | 7/2015 | Coursey et al. |
| 2015/0240298 A1 | 8/2015 | Piepenburg et al. |
| 2015/0258273 A1 | 9/2015 | Payne et al. |
| 2015/0290639 A1 | 10/2015 | Evtodienko |
| 2015/0322483 A1 | 11/2015 | Nakamura et al. |
| 2015/0346097 A1 | 12/2015 | Battrell et al. |
| 2015/0361419 A1 | 12/2015 | Kim et al. |
| 2016/0008811 A1 | 1/2016 | Laser et al. |
| 2016/0054316 A1 | 2/2016 | Egan et al. |
| 2016/0186240 A1 | 6/2016 | Andreyev et al. |
| 2016/0222442 A1 | 8/2016 | Cary |
| 2016/0256870 A1 | 9/2016 | Ismagilov et al. |
| 2016/0289669 A1 | 10/2016 | Fan et al. |
| 2016/0310948 A1 | 10/2016 | Nowakowski et al. |
| 2017/0021356 A1 | 1/2017 | Dority et al. |
| 2017/0058324 A1 | 3/2017 | Balog et al. |
| 2017/0121756 A1 | 5/2017 | Abate et al. |
| 2017/0152510 A1 | 6/2017 | Lorenz |
| 2017/0173585 A1 | 6/2017 | Mahony et al. |
| 2017/0173588 A1 | 6/2017 | Tang et al. |
| 2017/0182495 A1 | 6/2017 | Strey et al. |
| 2017/0203297 A1 | 7/2017 | Andreyev et al. |
| 2017/0247745 A1 | 8/2017 | Shultz et al. |
| 2017/0259263 A1 | 9/2017 | Andreyev et al. |
| 2017/0304829 A1 | 10/2017 | Andreyev et al. |
| 2018/0071734 A1 | 3/2018 | Andreyev et al. |
| 2018/0117590 A1 | 5/2018 | Andreyev et al. |
| 2018/0135108 A1 | 5/2018 | Etchebarne |
| 2018/0135110 A1 | 5/2018 | Saxena et al. |
| 2018/0304260 A1 | 10/2018 | Thomas et al. |
| 2019/0022643 A1 | 1/2019 | Andreyev et al. |
| 2019/0030532 A1 | 1/2019 | Andreyev et al. |
| 2019/0040451 A1 | 2/2019 | Mahony et al. |
| 2019/0060895 A1 | 2/2019 | Myers, III et al. |
| 2019/0083975 A1 | 3/2019 | Mitra et al. |
| 2019/0094114 A1 | 3/2019 | Myers, III et al. |
| 2019/0136226 A1 | 5/2019 | Swenson et al. |
| 2019/0151844 A1 | 5/2019 | Andreyev et al. |
| 2019/0169677 A1 | 6/2019 | Andreyev et al. |
| 2019/0193077 A1 | 6/2019 | Andreyev et al. |
| 2019/0232283 A1 | 8/2019 | Andreyev et al. |
| 2020/0086324 A1 | 3/2020 | Swenson et al. |
| 2020/0346213 A1 | 11/2020 | Andreyev et al. |
| 2020/0406256 A1 | 12/2020 | Andreyev et al. |
| 2020/0406257 A1 | 12/2020 | Andreyev et al. |
| 2021/0039097 A1 | 2/2021 | Andreyev et al. |
| 2021/0071236 A1 | 3/2021 | Andreyev et al. |
| 2021/0207194 A1 | 7/2021 | Ciopyk et al. |

FOREIGN PATENT DOCUMENTS

| | | |
|---|---|---|
| EP | 1347833 B1 | 10/2011 |
| EP | 2614147 A1 | 7/2013 |
| EP | 2682480 | 1/2014 |
| KR | 20100079360 A | 7/2010 |
| WO | WO-0149416 A1 | 7/2001 |
| WO | WO-2008/082432 | 7/2008 |
| WO | WO-2008149111 A1 | 12/2008 |
| WO | WO-2009047804 A2 | 4/2009 |
| WO | WO-2014035986 A1 | 3/2014 |
| WO | WO-2014144548 A2 | 9/2014 |
| WO | WO-2015138343 A1 | 9/2015 |
| WO | WO-2015138648 A1 | 9/2015 |
| WO | WO-2015164770 A1 | 10/2015 |
| WO | WO-2016040523 A1 | 3/2016 |
| WO | WO-2016109691 A1 | 7/2016 |
| WO | WO-2016203019 A1 | 12/2016 |
| WO | WO-2017/090043 | 6/2017 |
| WO | WO-2017/151195 | 9/2017 |
| WO | WO-2017/160840 | 9/2017 |
| WO | WO-2017197040 A1 | 11/2017 |
| WO | WO-2018/005710 | 1/2018 |
| WO | WO-2018005870 A1 | 1/2018 |
| WO | WO-2018/119443 | 6/2018 |

OTHER PUBLICATIONS

Choi, Gihoon et al., "A field-deployable mobile molecular diagnostic system for malaria at the point of need," Lab on a Chip, Royal Society of Chemistry, 2016, 16, 4341-4349.

Extended European Search Report for European Application No. 15876276.5, dated Aug. 7, 2018.

Extended European Search Report for European Application No. 17821297.3, dated Dec. 17, 2019.

Herbst De Cortina, S. et al. "A Systematic Review of Point of Care Testing for Chlamydia trachomatis, Neisseria gonorrhoeae, and Trichomonas vaginalis," Infectious Diseases in Obstetrics and Gynecology, vol. 2016, 17 pages (Mar. 7, 2016).

Huang et al., "Efficient SNP Discovery by Combining Microarray and Lab-on-a-Chip Data for Animal Breeding and Selection," Microarrays, Nov. 16, 2015, vol. 4, No. 4, pp. 570-595, entire document.

Huppert, J. et al. "What's the Point? How Point-of-Care STI Tests can Impact Infected Patients," National Institutes of Health, vol. 9(1): pp. 36-46 (Mar. 1, 2010).

International Search Report and Written Opinion for International Application No. PCT/US2018/060117, dated Apr. 12, 2019.

Invitation to Pay Additional Fees for International Application No. PCT/US18/60117, dated Feb. 8, 2019.

Kim, Yong Tae et al. "Integrated Microevidence of reverse transcription-polymerase chain reaction with colorimetric immunochromatographic detection for rapid gene expression analysis of influenza A H1N1 virus," Biosensors and Bioelectronics, Elsevier Science Ltd UK, Amsterdam, NL V. 33 No. 1, pp. 88-94, Dec. 14, 2011.

Lee et al. "Single-channel multiplexing without melting curve analysis in real-time PCR," Scientific Reports, Dec. 11, 2014, vol. 4, Art. No. 7439, pp. 1-6, entire document.

Moschou D., et al., 'All-plastic, low-power, disposable, continuous-flow PCR chip with integrated microheaters for rapid DNA amplification', Sensors and Actuators B: Chemical, vol. 199, Aug. 1, 2014, pp. 470-478.

Petralia, Salvatore et al. "PCR Technologies for Point of Care Testing: Progress and Perspectives," ACS Sensors, 2017, 2 (7), pp. 876-891, Jul. 6, 2017.

Roskos, Kristina et al. "Simple System for Isothermal DNA Amplification Coupled to Lateral Flow Detection," PLoS ONE 8(7): e69355. https://doi.org/10.1371/journal.pone.0069355; Jul. 26, 2013, 11 pages.

(56) References Cited

OTHER PUBLICATIONS

Wheeler, E.K., 'Under-three minute PCR: Probing the the limits of fast amplification', published Jul. 27, 2011 by the Royal Society of Chemistry: Analyst 2011 vol. 136 pp. 3707-3712.
Advisory Action for U.S. Appl. No. 15/474,083, dated Mar. 26, 2018.
BioFire Online Demo FilmArray. http://filmarray.com/the-evidence/online-demo. 2014, 6 pages.
Co-pending U.S. Appl. No. 16/228,709, filed Dec. 20, 2018.
Co-pending U.S. Appl. No. 16/234,453, filed Dec. 27, 2018.
Final Office Action for U.S. Appl. No. 15/474,083, dated Jan. 25, 2018.
Gehring, et al., A High-Throughput, Precipitating Colorimetric Sandwich ELISA Microarray for Shiga Toxins, J. Toxins, vol. 6, p. 1855-72, Jun. 11, 2014.
Hwang et al., "Black Printed Circuit Board-based Micro-Polymerase Chain Reaction Chip Structure for Fluorescence Detection Test", International Journal of Control and Automation, 8(10):15-24, 2015.
Interbiotech, "Enzymatic substrates for ImmunoAssays," [retreived from the Internet Nov. 18, 2017:< http://www.interchim.fr/ft/B/BA357a.pdf], 10 pages.
International Search Report and Written Opinion for International Application No. PCT/US2017/029004, dated Aug. 23, 2017.
International Search Report and Written Opinion for International Application No. PCT/US2017/039844, dated Dec. 7, 2017.
Kim, et al., Automated microfluidic DNA/RNA extraction with both disposable and reusable components. Journal of Micromechanics and Microengineering, Dec. 2011; 22(1):pp. 6,8,11.
Kopp et al., Chemical amplification: Continuous-flow PCR on a chip. Science, 280(5366):1046-1048, 1998.
Lee, et al., A polymer lab-on-a-chip for reverse transcription (RT)-PCR based point-of-care clinical diagnostics. The Royal Society of Chemistry, Oct. 2008; 8:2121-27.
Mohammed, et al., Modelling of Serpentine Continuous Flow Polymerase Chain Reaction Microfluidics. IJEST, Mar. 2012; 4(3), pp. 1183-1189.
Non-final Office Action for U.S. Appl. No. 15/474,083, dated Aug. 24, 2017.
Office Action for U.S. Appl. No. 15/586,780, dated Feb. 6, 2018.
PCT Patent Application No. PCT/US2015/019497 International Search Report and Written Opinion dated Jun. 8, 2015.
PCT Patent Application No. PCT/US2015/049247 International Search Report and Written Opinion dated Jan. 12, 2016.
PCT/US2015/019497 International Preliminary Report on Patentability dated Sep. 13, 2016.
PCT/US2015/049247 International Preliminary Report on Patentability dated Mar. 14, 2017.
PCT/US2015/068101 International Preliminary Report on Patentability dated Jul. 13, 2017.
PCT/US2015/068101 International Search Report and Written Opinion dated May 5, 2016.
PCT/US2017/032035 International Search Report and Written Opinion dated Oct. 4, 2017.
PCT/US2017/040112 International Search Report and Written Opinion dated Nov. 9, 2017.
Schwerdt. Application of ferrofluid as a valve/pump for polycarbonate microfluidic devices. Johns Hopkins University. NSF Summer Undergraduate Fellowship in Sensor Technologies 2006, 17 pages.
Shafagati, et al., The Use of NanoTrap Particles as a Sample Enrichment Method to Enhance the Detection of Rift Valley Fever Virus. PLOS Negrlected Tropical Diseases, Jul. 4, 2013;7(7):e2296.
Tanriverdi, et al. A rapid and automated sample-to-result HIV load test for near-patient application. J Infect Dis., 201 Suppl 1:S52-S58, 2010. doi: 10.1086/650387.
Thiha, et al., A Colorimetric Enzyme-Linked Immunosorbent Assay (ELISA) Detection Platform for a Point-of-Care Dengue Detection System on a Lab-on-Compact-Disc. Sensors (Basel). May 18, 2015;15(5):11431-41. doi: 10.3390/s150511431.
U.S. Appl. No. 15/124,334 Notice of Allowance dated Sep. 26, 2018.
U.S. Appl. No. 14/984,573 First Action Interview Pilot Program Pre-Interview Communication dated Aug. 16, 2016.
U.S. Appl. No. 14/984,573 Notice of Allowance dated Feb. 10, 2017.
U.S. Appl. No. 14/984,573 Office Action dated Aug. 16, 2016.
Office Action for CN Application No. 201580076979.3, dated Feb. 22, 2021.
Ahrberg, Christian D. et al. "Polymerase chain reaction in microfluidic devices," © The Royal Society of Chemistry 2016, Lab Chip, 16, pp. 3866-3884, 20 pgs.
Bartlett, John G. "Diagnostic Tests for Agents of Community-Acquired Pneumonia," Clinical Infectious Diseases 2011;52 (Suppl 4) pp. S296-S304.
Poritz, Mark A. et al., "FilmArray, an Automated Nested Multiplex PCR System for Multi-Pathogen Detection: Development and Application to Respiratory Tract Infection," PLoS ONE www.plosone.org, Oct. 2011, vol. 6, Issue 10 (14 pgs.).
Suehiro, Noriko et al. "A simplified method for obtaining plant viral RNA for RT-PCR," Journal of Virological Methods 125 (2005) pp. 67-73.
Terhes et al. "Comparison of a Rapid Molecular Method, the BD GeneOhm Cdiff Assay, to the Most Frequently Used Laboratory Tests for Detection of Toxin-Producing Clostridium difficile in Diarrheal Feces," Journal of Clinical Microbiology, vol. 47, No. 11, Nov. 2009, pp. 3478-3481.
White, Adam K. et al. High-throughput microfluidic single-cell RT-qPCR, PNAS, Aug. 23, 2011, vol. 108, No. 34, pp. 13999-14004.
White, Adam K. et al. "High-throughput microfluidic single-cell RT-qPCR. Supporting Information White et al. 10.1073/pnas.1019446108" PNAS, Aug. 23, 2011, vol. 108, No. 34, pp. 1-9.
Wu, Jinbo et al. "Extraction, amplification and detection of DNA in microfluidic chip-based assays," © Springer-Verlag Wein 2013, pp. 1611-1631.
Zhang, Chunsun et al. "Survey and Summary—Miniaturized PCR chips for nucleic acid amplification and analysis: latest advances and future trends," Nucleic Acids Research, 2007, vol. 35, No. 13, pp. 4223-4237.
Zhang, Chunsun et al. "PCR microfluidic devices for DNA amplification," Biotechnology Advances 24, (2006) pp. 243-284.
Zumla, Alimuddin et al., "Emerging respiratory tract infections 4—Rapid point of care diagnostic tests for viral and bacterial respiratory tract infections—needs, advances, and future prospects," Lancet Infect. Dis. www.thelancet/infection, vol. 14, Nov. 2014, pp. 1123-1135.

FIG. 21
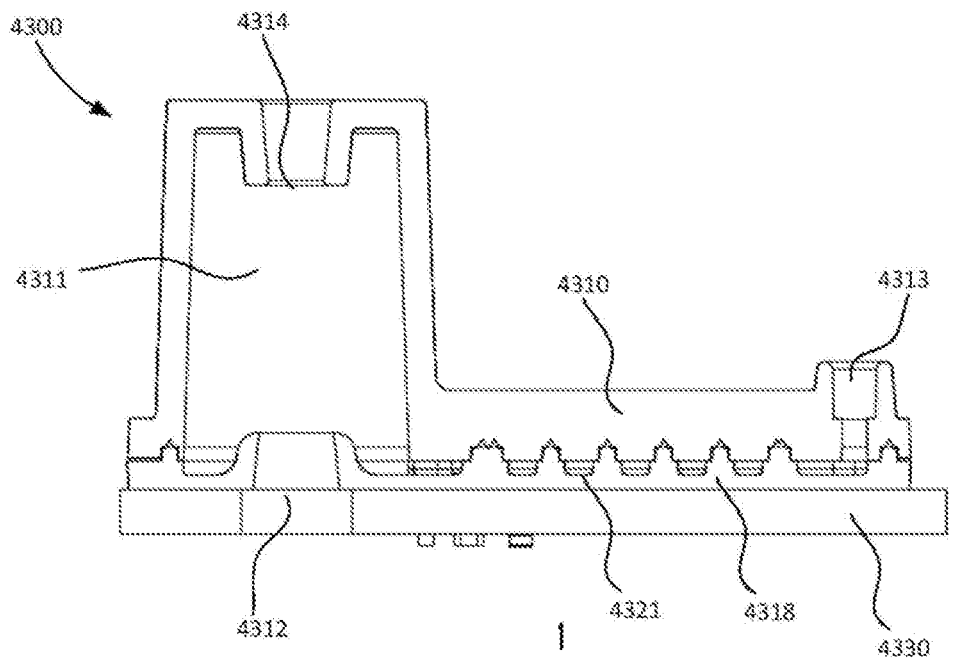
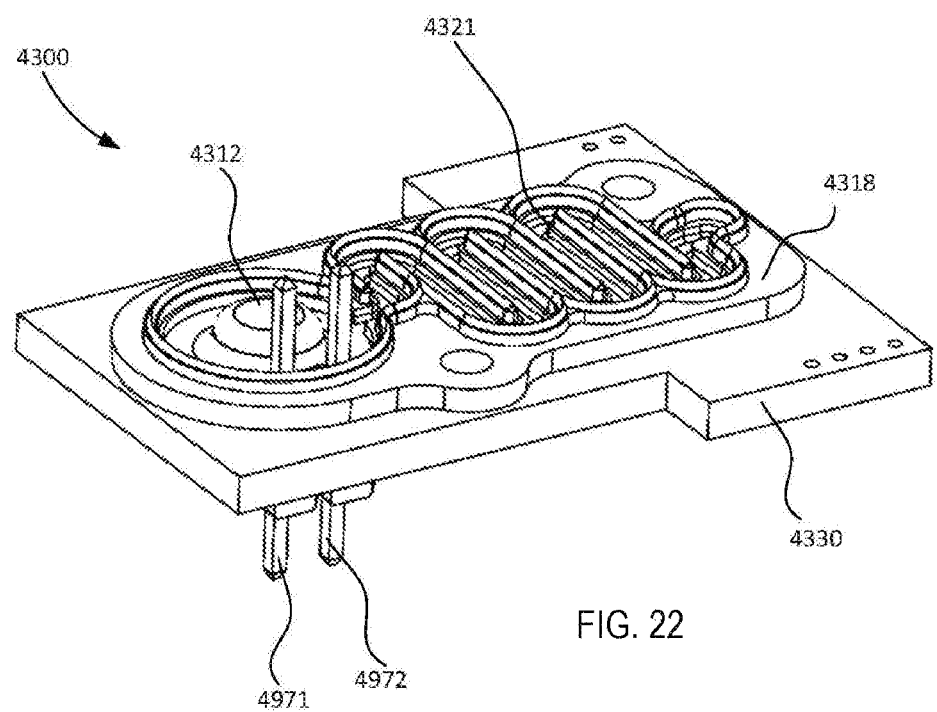
FIG. 22

FIG. 27

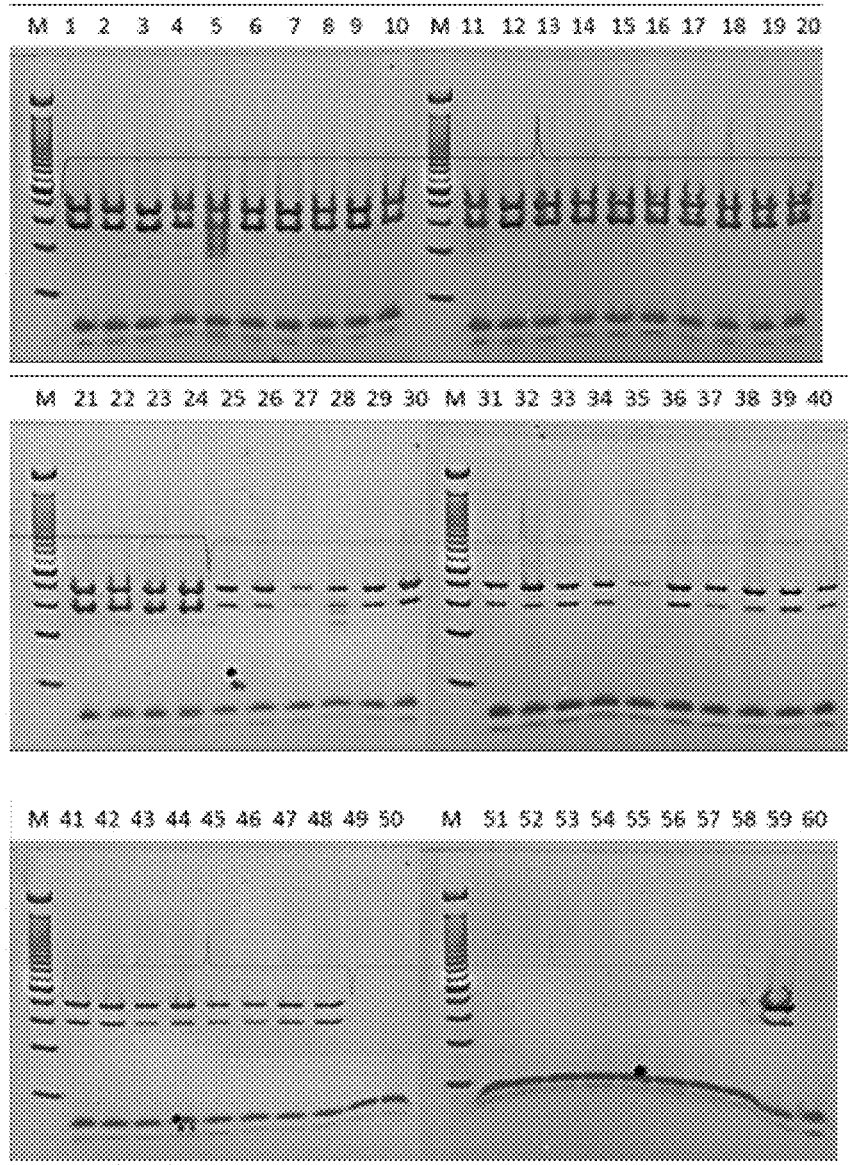

Samples in TT buffer
Samples in MSwab
Samples in L. Amies

M= 25 by DNA Ladder
1= TT Ctrl (neat)
2= 97 in TT (neat)
3= 99 in TT (neat)
4= 109 in TT (neat)
5= 111 in TT (neat)
6= 124 in TT (neat)
7= TT Ctrl (66.6%)
8= 97 in TT (66.6%)
9= 99 in TT (66.6%)
10= 109 in TT (66.6%)
11= 111 in TT (66.6%)
12= 124 in TT (66.6%)
13= TT Ctrl (50%)
14= 97 in TT (50%)
15= 99 in TT (50%)
16= 109 in TT (50%)
17= 111 in TT (50%)
18= 124 in TT (50%)
19= TT Ctrl (33.3%)
20= 97 in TT (33.3%)
21= 99 in TT (33.3%)
22= 109 in TT (33.3%)
23= 111 in TT (33.3%)
24= 124 in TT (33.3%)
25= MS Ctrl (neat)
26= 97 in MS (neat)
27= 99 in MS (neat)

28= 109 in MS (neat)
29= 111 in MS (neat)
30= 124 in MS (neat)
31= MS Ctrl (66.6%)
32= 97 in MS (66.6%)
33= 99 in MS (66.6%)
34= 109 in MS (66.6%)
35= 111 in MS (66.6%)
36= 124 in MS (66.6%)
37= MS Ctrl (50%)
38= 97 in MS (50%)

39= 99 in MS (50%)
40= 109 in MS (50%)
41= 111 in MS (50%)
42= 124 in MS (50%)
43= MS Ctrl (33.3%)
44= 97 in MS (33.3%)
45= 99 in MS (33.3%)
46= 109 in MS (33.3%)
47= 111 in MS (33.3%)
48= 124 in MS (33.3%)
49= LA Ctrl (neat)

50= 97 in LA (neat)
51= LA Ctrl (66.6%)
52= LA Ctrl (50%)
53= LA Ctrl (33.3%)
54= 97 in LA (33.3%)
55= 99 in LA (33.3%)
56= 109 in LA (33.3%)
57= 111 in LA (33.3%)
58= 124 in LA (33.3%)
59= PCR (+) Ctrl
60= NTC

DEVICES AND METHODS FOR NUCLEIC ACID EXTRACTION

CROSS-REFERENCE

This application is a continuation of International Patent Application No. PCT/US2017/032035, filed May 10, 2017, which claims priority to U.S. Provisional Patent Application Ser. No. 62/334,982, filed May 11, 2016, U.S. Provisional Patent Application Ser. No. 62/356,451, filed Jun. 29, 2016, and U.S. Provisional Patent Application Ser. No. 62/356,596, filed Jun. 30, 2016, which applications are incorporated herein by reference.

BACKGROUND OF THE INVENTION

Sample preparation methods involving the extraction of nucleic acid molecules from biological cells are widely used. Oftentimes, the nucleic acid molecules are to be used in downstream applications, for example, amplification (e.g., PCR) or sequencing methods. These methods, however, can be sensitive to additional components found in the sample mixture. These additional components may be residual components carried over from the sample preparation method. Thus, the sample preparation method should be able to generate a nucleic acid sample of sufficient quality to perform the intended downstream application. Furthermore, standard sample preparation methods may be time-consuming, ranging on the order of hours to be complete.

SUMMARY OF THE INVENTION

In one aspect, a method is provided for nucleic acid extraction, comprising: (a) obtaining a biological sample comprising one or more biological entities; (b) capturing the one or more biological entities on a filter; (c) washing the filter; (d) eluting the one or more biological entities from the filter; and (e) lysing the one or more biological entities, thereby releasing a plurality of nucleic acid molecules therefrom, wherein the method extracts the nucleic acid molecules from the one or more biological entities within 5 minutes or less at a quality sufficient to successfully perform a polymerase chain reaction (PCR). In some cases, the one or more biological entities comprise one or more biological cells. In some cases, the one or more biological cells comprise one or more bacterial cells, fungal cells, mammalian cells or a combination thereof. In some cases, the one or more biological entities comprise one or more viruses. In some cases, the nucleic acid molecules comprise RNA. In some cases, the nucleic acid molecules comprise DNA. In some cases, the lysing further comprises flowing a lysis solution over the one or more biological entities on the filter. In some cases, the lysis solution comprises a lysis enzyme. In some cases, the lysis enzyme is proteinase K. In some cases, the proteinase K is present in the lysis solution at a concentration of about 0.001 mg/mL to about 10 mg/mL. In some cases, about 10 µL to about 50 mL of lysis solution is flowed over the filter. In some cases, the washing further comprises, (i) pushing a wash solution through the filter; (ii) pushing air through the filter; (iii) or a combination of both. In some cases, the lysis solution is back-flushed over the filter. In some cases, the wash solution comprises bovine serum albumin and/or a detergent. In some cases, the wash solution comprises about 0.1% to 5% bovine serum albumin. In some cases, the wash solution comprises about 0.1%, 0.2%, 0.3%, 0.4%, 0.5%, 1%, 1.5%, 2%, 2.5%, 3%, 4%, or 5% bovine serum albumin. In some cases, the wash solution comprises about 0.1% to 20% detergent. In some cases, the wash solution comprises about 1%, 2%, 3%, 4%, 5%, 6%, 7%, 8%, 9%, or 10% detergent. In some cases, the detergent is Tween-20. In some cases, the biological sample comprises urine, a vaginal swab, a cervical swab, or blood. In some cases, the filter comprises cellulose, polyethersulfone (PES), nylon, polyvinylidene fluoride (PVDF), polycarbonate or borosilicate glass fiber. In some cases, the filter has a pore size of about 0.2 µm to about 20 µm. In some cases, the lysing further comprises incubating the biological sample in the lysis solution for a period of time at a specified temperature. In some cases, the period of time comprises from about 0.01 seconds to about 48 hours. In some cases, the specified temperature comprises from about 4° C. to about 75° C. In some cases, the method further comprises inactivating said lysis solution. In some cases, the inactivating comprises incubating said lysis solution at a temperature of about 57° C. to about 100° C. at a time period from about 0.01 seconds to about 48 hours. In some cases, the nucleic acid molecules comprise DNA and the DNA is extracted from the one or more biological entities with a A260/A280 ratio of at least 1.5. In some cases, the nucleic acid molecules comprise RNA and the RNA is extracted from the one or more biological entities with a A260/A280 ratio of at least 1.7. In some cases, the method further comprises performing a polymerase chain reaction on the extracted nucleic acid molecules. In some cases, the polymerase chain reaction successfully amplifies a target nucleic acid sequence present in the extracted nucleic acid molecules.

In another aspect, a device is provided. In some cases, the device is configured to perform a method of the disclosure. In some cases, the device comprises: (a) an input port, configured to receive the biological sample comprising one or more biological entities; (b) a filter assembly comprising a filter configured to capture the one or more biological entities, wherein the input port is configured to relay the biological sample to the filter assembly; (c) one or more reservoirs comprising a wash solution, a lysis solution, or both, operably coupled to the filter assembly; (d) a waste chamber, operably coupled to the filter assembly and configured to receive waste from the filter assembly; and (e) an elution chamber, operably coupled to the filter assembly and configured to receive an eluent from the filter assembly. In some cases, the elution chamber further comprises a heating element in contact with the elution chamber. In some cases, the device further comprises an inactivation chamber, operably coupled to the elution chamber. In some cases, the inactivation chamber further comprises a heating element. In some cases, the inactivation chamber comprises a serpentine flow path in contact with the heating element. In some cases, the input port, the filter assembly, the one or more reservoirs, the waste chamber, and the elution chamber are contained within a housing. In some cases, the device is handheld. In some cases, the device is configured for one-time use. In some cases, the device is configured to extract said nucleic acid molecules from the biological entities in 5 minutes or less at a quality sufficient to successfully perform a polymerase chain reaction. In some cases, the device further comprises one or more additional elements for performing a polymerase chain reaction.

In one aspect a method is provided for nucleic acid extraction, comprising: obtaining a biological sample comprising one or more biological entities; capturing said one or more biological entities on a filter; eluting said one or more biological entities from said filter; and lysing said one or more biological entities, thereby releasing a plurality of nucleic acid molecules therefrom, wherein said method extracts said nucleic acid molecules from said one or more biological entities within 5 minutes or less at a quality sufficient to successfully perform a polymerase chain reaction (PCR). In some cases the method further comprises that the filter consists of two filter membranes, a first filter membrane and a second filter membrane with a smaller pore size than the first filter membrane. In some cases the method further comprises a wash step, whereby once the biological entities are captured on the filter the filter and biological entities are washed with an air wash.

In one aspect a method is provided for nucleic acid extraction, comprising: obtaining a biological sample comprising one or more biological entities; and lysing said one or more biological entities, thereby releasing a plurality of nucleic acid molecules therefrom, wherein said method extracts said nucleic acid molecules from said one or more biological entities within 5 minutes or less at a quality sufficient to successfully perform a polymerase chain reaction (PCR). In some cases the method is performed by a handheld device. In some cases a quality sufficient to successfully perform a polymerase chain reaction comprises nucleic acid molecules which amplify with at least 70% efficiency as determined by a qPCR standard curve. In some cases the method produces at least 100 µL of a solution containing the nucleic acid molecules. In some cases the method produces at least 300 µL of a solution containing the nucleic acid molecules. In some cases the method produces at least 500 µL of a solution containing the nucleic acid molecules. In some cases the method further comprises catching biological entities on a filter and subjecting the biological entities and filter to an air wash. In some cases the biological entities are washed with a volume of air sufficient to dry the filter. In some cases the biological entities are washed with at least about 1.5 mL of air.

In another aspect a device is provided. In some cases the device comprises: an input port, configured to receive said biological sample comprising one or more biological entities; a holding tank, operably coupled to said input port, an inactivation section, and containing a heating element; and an output port. In some cases the device further comprises a permanent vent. In some cases the holding tank further comprises an electrical probe which can sense the presence of liquid in the holding tank. In some cases the inactivation chamber comprises a serpentine path.

In a further aspect a method of nucleic acid extraction comprises: conveying a biological sample into a sample input module of a molecular diagnostic test device; and actuating the molecular diagnostic test device to: convey the biological sample from the sample input module to a lysing module, the lysing module including a heater and defining a first reaction volume and a second reaction volume; maintain an input solution containing the biological sample and a lysis buffer within the first reaction module to lyse at least a portion of the biological sample thereby releasing a plurality of nucleic acid molecules; activate the heater to heat a portion of the lysing module to produce an inactivation temperature zone within the second reaction volume; and produce a flow of the input solution within the second reaction volume such that a volume of the input solution is heated within the inactivation temperature. In some cases the volume of the input solution is at least 10 microliters. In some cases the volume of the input solution is produced within five minutes or less. In some cases the second reaction volume is a serpentine flow path. In some cases a wall of the lysing module that defines the second reaction volume has a surface area, a ratio of the surface area to the second reaction volume being greater than about 10 cm$^{-1}$. In one example, a ratio of the surface area to the second reaction volume is about 20 cm$^{-1}$. In some cases the volume of the input solution is heated to an inactivation temperature of between about 57 degrees Celsius and about 100 degrees Celsius for a time period from about 15 seconds. In some cases the flow of the input solution is such that the volume of the input solution is heated to an inactivation temperature of between about 92 degrees Celsius and about 98 degrees Celsius for a time period of at least about 25 seconds. In some cases the first reaction volume is in fluid communication with the second reaction volume; and the lysing module defines a vent opening into the first reaction volume. In some cases the volume of the input solution is heated to an inactivation temperature of at least about 95 degrees Celsius; and the input solution within the first reaction module contains at least one of a salt or a sugar formulated to raise a boiling temperature of the input solution. In some cases the portion of the lysing module is a second portion, the actuating the molecular diagnostic test device further causes the molecular diagnostic test device to: heat a first portion of the lysing module to produce a lysing temperature zone within the second reaction volume, the flow of the input solution within the second reaction volume being such that the volume of the input solution is heated within the lysing temperature zone to lyse a biological entity within the volume of the input solution.

In some cases the plurality of nucleic acid molecules includes DNA, the DNA being extracted from said one or more biological entities with a A260/A280 ratio of at least 1.5.

In some cases the actuating the molecular diagnostic test device causes the molecular diagnostic test device to: convey the biological sample from the sample input module through a filter to retain a biological entity with the biological sample on the filter; and produce a flow of an elution buffer through the filter to produce the input solution and convey the input solution to the lysing module. In some cases the actuating the molecular diagnostic test device includes moving a sample actuator to produce a pressure within the sample input module to convey the biological sample from the sample input module towards the lysing module. In some cases the sample actuator is a non-electronic actuator. In some cases the actuating the molecular diagnostic test device further causes the molecular diagnostic test device to: receive an electronic signal from a sensor within the lysing module, the electronic signal indicating the presence of the input solution within the first reaction module; and activate the heater in response to the electronic signal.

In some cases the actuating the molecular diagnostic test device further causes the molecular diagnostic test device to: heat a portion of an amplification module within the molecular diagnostic test device to amplify a nucleic acid from the plurality of nucleic acid molecules to produce an output containing a target amplicon; and convey the output to a detection module of the molecular diagnostic test device.

In some cases a method described herein further comprises viewing a visible signal indicating a presence of the target amplicon; and discarding, after the viewing, the molecular diagnostic test device.

In an aspect an apparatus is provided. The apparatus comprises a housing; a sample input module defining an input reservoir configured to receive a biological sample, the biological sample containing a biological entity; a lysing module disposed within the housing, the lysing module including a heater and first flow member, the first flow member defining a first volume and a second volume, the first volume configured to receive an input solution containing at least the biological sample and a lysis buffer, the heater coupled to the first flow member and configured to convey thermal energy into the second volume to A) lyse at least a portion of the biological sample thereby releasing a plurality of nucleic acid molecules and B) inactivate an enzyme within the input solution when a volume of the input solution flows through the second volume; and an amplification module disposed within the housing, the amplification module including a second flow member configured to receive the volume of the input solution from the lysing module, the amplification module configured to amplify a nucleic acid molecule from the plurality of nucleic acid molecules within the volume of the input solution to produce an output containing a target amplicon. In some cases the second volume is a serpentine flow path. In some cases a wall of the lysing module that defines the second volume has a surface area, a ratio of the surface area to the second reaction volume being greater than about 20 $cm^{-1}$. In one example, a ratio of the surface area to the second reaction volume is about 20 $cm^{-1}$.

In some cases the first volume is in fluid communication with the second reaction volume; and the lysing module defines a vent opening into the first volume. In some cases the lysing module includes a sensor disposed within the first volume, the sensor configured to produce an electronic signal indicating the presence of the input solution within the first module, the heater activated in response to the electronic signal. In some cases the heater is a first heater; the second flow member defines an amplification flow path; and the amplification module includes a second heater different from the first heater, the second heater coupled to the second flow member and configured to convey thermal energy into the amplification flow path to amplify the nucleic acid molecule from the plurality of nucleic acid molecules.

In some cases an apparatus further comprises a non-electronic sample actuator to produce a pressure within the sample input module to convey the biological sample from the sample input module towards the lysing module; and a fluid pump disposed within the housing, the fluid pump configured to produce a flow of the input solution from the lysing module to the amplification module. In some cases the flow of the input solution from the lysing module to the amplification module is in a first direction; and the lysing module includes a check valve to configured to prevent a flow of the input solution in a second direction.

In an aspect a device is provided. The device comprises a holding tank which contains two electrical probes which may be used to determine the electrical resistance of the fluid within the holding tank, thus determining whether liquid has entered the holding tank.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 21 is a cross-sectional view of the lysing module shown in FIGS. 17 and 18 taken along line $X_2$-$X_2$ in FIG. 19.

FIG. 22 is a perspective view of a portion of the lysing module shown in FIGS. 17 and 18.

FIG. 27 illustrates the results of a PCR reaction performed upon DNA extracted using the methods of this disclosure.

DETAILED DESCRIPTION OF THE INVENTION

Figure 1:
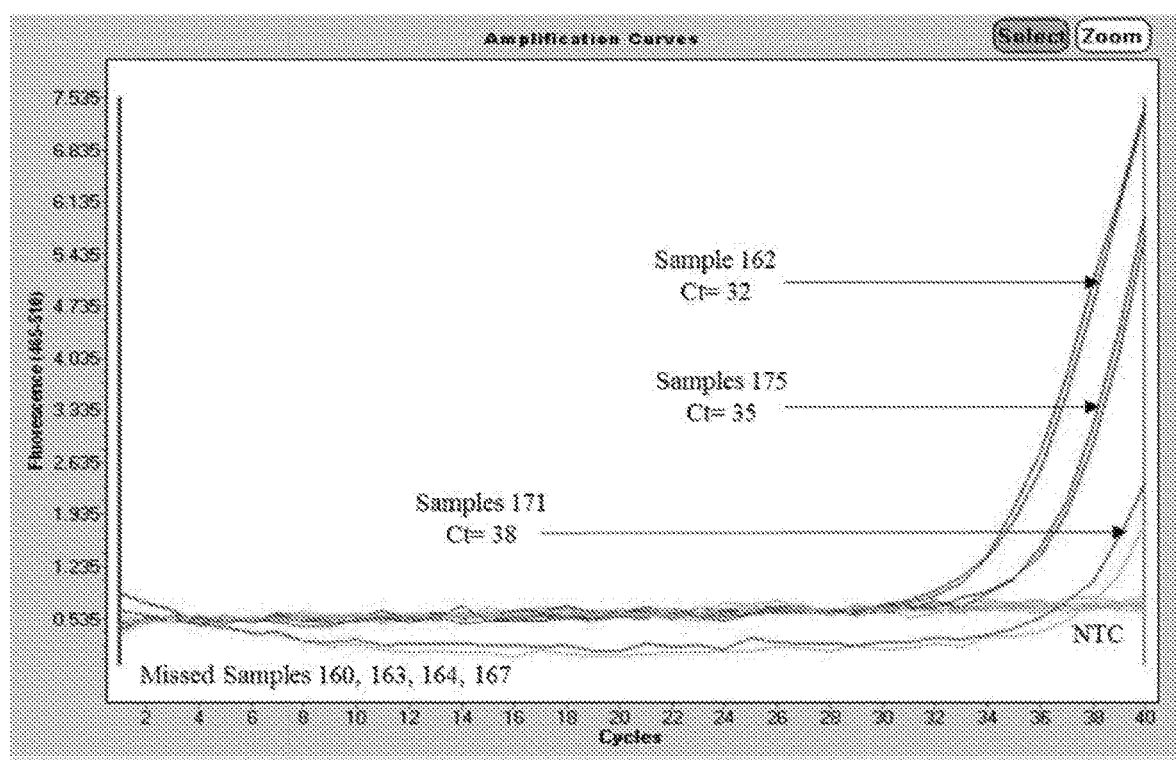
FIG. 1 depicts data generated from a real-time PCR reaction performed on DNA extracted from clinical samples utilizing the methods provided herein.
Figure 2:
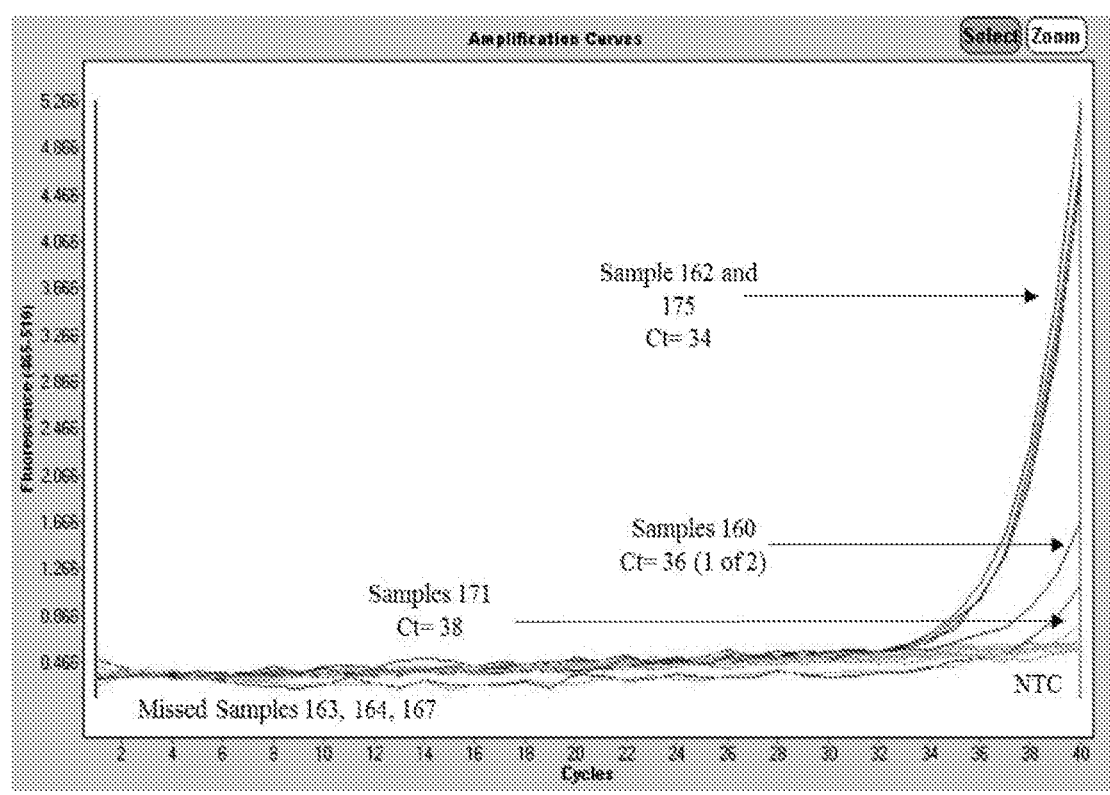
FIG. 2 depicts data generated from a real-time PCR reaction performed on DNA extracted from clinical samples utilizing standard DNA extraction methods.

Disclosed herein are devices and methods for the preparation of nucleic acid molecules for downstream applications. In some cases, the devices and methods are utilized for the extraction of nucleic acid molecules from a biological sample. In some cases, the devices and methods are utilized for the purification of nucleic acid molecules from a biological sample. The devices described herein may include self-contained, handheld devices. The devices described herein may include one or more components that aid in the extraction, purification, and/or processing of a biological sample and the nucleic acids contained therein. In some cases, the methods include the use of a device that includes one or more components that aid in the extraction, purification, and/or processing of a biological sample and the nucleic acids contained therein.

In one aspect, a method is provided for nucleic acid extraction. The method may include one or more steps including: (a) obtaining a biological sample comprising one or more biological entities; (b) capturing the one or more biological entities on a filter; (b) washing the filter with a wash solution and/or air; (c) eluting the one or more biological entities from the filter; and (d) lysing the one or more biological entities, thereby releasing a plurality of nucleic acid molecules therefrom. In some cases, the wash solution comprises bovine serum albumin and/or a detergent. In some cases, the wash solution comprises about 0.1% to 5% bovine serum albumin. In some cases, the wash solution comprises about 0.1%, 0.2%, 0.3%, 0.4%, 0.5%, 1%, 1.5%, 2%, 2.5%, 3%, 4%, or 5% bovine serum albumin. In some cases, the wash solution comprises about 0.1% to 20% detergent. In some cases, the wash solution comprises about 1%, 2%, 3%, 4%, 5%, 6%, 7%, 8%, 9%, or 10% detergent. In some cases, the detergent is Tween-20. In some embodiments the method may not require use of a filter. In other embodiments the method may use a filter but not require a wash solution.

In some cases, the method involves obtaining or providing a biological sample. The biological sample can be derived from a non-cellular entity comprising polynucleotides (e.g., a virus) or from a cell-based organism (e.g., member of archaea, bacteria, or eukarya domains).

Generally, the biological sample will contain one or more biological entities that comprise one or more polynucleotides or nucleic acid molecules. A "nucleic acid molecule", "nucleic acid" or "polynucleotide" may be used interchangeably throughout and may refer to deoxyribonucleic acid (DNA) or ribonucleic acid (RNA) including known analogs or a combination thereof unless otherwise indicated. Nucleic acid molecules to be profiled herein can be obtained from any source of nucleic acid. The nucleic acid molecule can be single-stranded or double-stranded. In some cases, the nucleic acid molecules are DNA. The DNA can be mitochondrial DNA, complementary DNA (cDNA), or genomic DNA. In some cases, the nucleic acid molecules are genomic DNA (gDNA). The DNA can be plasmid DNA, cosmid DNA, bacterial artificial chromosome (BAC), or yeast artificial chromosome (YAC). The DNA can be derived from one or more chromosomes. For example, if the DNA is from a human, the DNA can derived from one or more of chromosomes 1, 2, 3, 4, 5, 6, 7, 8, 9, 10, 11, 12, 13, 14, 15, 16, 17, 18, 19, 20, 21, 22, X, or Y. In some cases, the nucleic acid molecules are RNA. RNA can include, but is not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoRNAs, microRNAs, siRNAs, piRNAs and long nc RNAs. The source of nucleic acid for use in the methods and compositions described herein can be a sample comprising the nucleic acid.

In some aspects, the methods involve capturing one or more biological cells or biological entities (e.g., a virus) present in the biological sample on a filter membrane. The filter membrane may be of any suitable material, non-limiting examples including nylon, cellulose, polyethersulfone (PES), polyvinylidene difluoride (PVDF), polycarbonate, borosilicate glass fiber and the like. In some examples, the filter membrane is nylon. In some cases, the filter membrane has an average pore size of about 0.2 µm to about 20 µm. For example, the filter membrane may have an average pore size of about 0.2 µm, about 0.5 µm, about 1 µm, about 2 µm, about 3 µm, about 4 µm, about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, about 20 µm, or greater than 20 µm. In some examples, the surface of the filter membrane may be chemically treated or coated in such a way as to improve the binding of a biological cell or entity to the membrane. For example, without limitation, the filter membrane may be treated with sodium polyphosphate.

Clinical swab samples may contain mucus (or other substances) which can lead to clogging of the filter used in sample prep. If the filter is clogged then pressures may build up which may lead to leaks in the fluidic path of the sample prep device and/or tears or breaks in the capture filter itself. In some examples a second filter may be provided which sits next to a first filter. For example, a mesh screen may be placed on the input side of the 5 micron nylon filter. This may reduce pressure from mucus samples and also prevent the 5 micron nylon filter from breaking. A mesh screen could also be placed on the exit side of the 5 micron nylon filter which would also prevent the 5 micron nylon filter from breaking, however this likely would not reduce the pressure required to push a sample (mucus) through.

The mesh screen may be made from any plastic materials and may contain pore sizes from 1 micron to 1000 microns. In some embodiments the mesh screen may be a woven nylon mesh with 100 micron pores. The mesh screen is assembled into the housing that also contains the 5 micron nylon filter. The second filter may have a much larger pore size than the first filter and prevent clogging of the first filter. For example the first filter may have a pore size of about 0.1-20, 1-15, 1-10, 5-10, 1-5 or 0.1-1 µm while the second filter has a pore size of about 10-1000, 50-500, 100-500, 50-100, or 100-200 µm. In one example the first filter has a pore size of 5 µm and the second filter has a pore size of 100 µm. The mesh filter may also be made from non-woven polypropylene. The mesh screen may have a thickness of about 150 µm, 200 µm or greater than 200 µm. After the biological cells or biological entities are captured on the filter membrane, the filter membrane may be optionally washed with one or more wash steps. The wash step may be utilized to, for example, remove any undesired material from the membrane. In some cases, the wash step may involve pushing or forcing a fluid solution over or through the membrane (e.g., a buffer). The volume of wash solution may be from about 10 µL to about 50 mL. For example, the volume of wash solution may be about 10 µL, about 50 µL, about 100 µL, about 200 µL, about 300 µL, about 400 µL, about 500 µL, about 600 µL, about 700 µL, about 800 µL, about 900 µL, about 1 mL, about 5 mL, about 10 mL, about 15 mL, about 20 mL, about 25 mL, about 30 mL, about 35 mL, about 40 mL, about 45 mL, about 50 mL or greater than 50 mL. In other cases, the wash step may involve pushing or forcing air over or through the membrane. This step may be advantageous in decreasing the volume of sample buffer that is carried over into the lysis buffer. The volume of air wash may be from about 0.1 µL to about 100 L, or about 10 µL to about 50 mL. For example, the volume of air wash may be about 10 µL, about 50 µL, about 100 µL, about 200 µL, about 300 µL, about 400 µL, about 500 µL, about 600 µL, about 700 µL, about 800 µL, about 900 µL, about 1 mL, about 5 mL, about 10 mL, about 15 mL, about 20 mL, about 25 mL, about 30 mL, about 35 mL, about 40 mL, about 45 mL, about 50 mL or greater than 50 mL. In some cases, an air wash volume of about 1-5 mL may be preferred. For example an air wash may be have a volume of about 1.5 mL. In cases where an air wash is used the subsequent liquid wash may be more effective and/or the final eluted sample may be cleaner than if no air wash were used. In some cases, the wash step involves both a fluid wash step and an air wash step, performed in any order. In some cases, the wash solution comprises bovine serum albumin and/or a detergent. In some cases, the wash solution comprises about 0.1% to 5% bovine serum albumin. In some cases, the wash solution comprises about 0.1%, 0.2%, 0.3%, 0.4%, 0.5%, 1%, 1.5%, 2%, 2.5%, 3%, 4%, or 5% bovine serum albumin. In some cases, the wash solution comprises about 0.1% to 20% detergent. In some cases, the wash solution comprises about 1%, 2%, 3%, 4%, 5%, 6%, 7%, 8%, 9%, or 10% detergent. In some cases, the detergent is Tween-20. In some embodiments, the bovine serum albumin and/or detergent increase the viscosity of the wash solution in manner which increases the surface area of the filter contacted with the wash solution during a wash step as compared to a wash solution lacking one or both of bovine serum albumin and detergent.

After the membrane is washed, the biological cells or entities captured on the membrane may be lysed or otherwise disrupted so as to release a plurality of nucleic acid molecules contained therein. The methods and devices of this disclosure may use chemical, enzymatic and/or thermal methods to lyse the sample. In some embodiments the methods and devices of this disclosure do not use ultrasound to lyse the sample. In some cases, the cells may be lysed be heating the sample. For example the sample may be heated to greater than about 90° C. for longer than about 10 seconds. In some examples heating the sample to about 95° C. for about 20 seconds is seen to be sufficient to lyse the sample.

In some cases, lysis involves flowing a lysis buffer over the biological cells or entities captured on the membrane. In some cases, the lysis buffer is flowed through the filter membrane. In other cases, the lysis buffer is back-flowed through the filter membrane. The lysis buffer may be osmotically imbalanced so as to force fluid into the cells to rupture the cell membranes. In some cases, the lysis buffer may include one or more surfactants or detergents. Non-limiting examples of surfactants or detergents that may be used include: nonionic sufactants including polyoxyethylene glycol alkyl ethers (sold as Brij® series detergents including Brij® 58, Brij® 52, Brij® L4 and Brij® L23), octaethylene glycol monododecyl ether, pentaethylene glycol monododecyl ether, polyoxypropylene glycol alkyl ethers, glucoside alkyl ethers (e.g., decyl glucoside, lauryl glucoside, octyl glucoside), polyoxyethylene glycol octylphenol ethers (e.g., Triton X-100), polyoxyethylene glycol alkylphenol ethers (e.g., nonoxynol-9), glycerol alkyl esters (e.g., glyceryl laurate), polyoxyethylene glycol sorbitan alkyl esters (e.g., polyoxyethylene glycol (20) sorbitan monolaurate, polyoxyethylene glycol (40) sorbitan monolaurate, polyoxyethylene glycol (20) sorbitan monopalmitate, polyoxyethylene glycol (20) sorbitan monostearate, polyoxyethylene glycol (4) sorbitan monostearate, polyoxyethylene glycol (20) sorbitan tristearate, polyoxyethylene glycol (20) sorbitan monooleate)), sorbitan alkyl esters (e.g., sorbitan monolaurate, sorbitan monopalmitate, sorbitan monostearate, sorbitan monooleate, sorbitan sesquioleate, sorbitan trioleate, sorbitan isostearate), cocamide monoethanolamine, cocamide diethanolamine, dodecyldimethylamine oxide, poloxamers including those sold under the Pluronic®, Synperonic® and Kolliphor® tradenames, and polyethoxylated tallow amine (POEA); anionic surfactants including ammonium lauryl sulfate, ammonium perfluorononanoate, docusate, perfluorobutanesulfonic acid, perfluorononanoic acid, perfluorooctanesulfonic acid, perfluorooctanoic acid, potassium lauryl sulfate, sodium alkyl sulfate, sodium dodecyl sulfate, sodium dodecylbenzenesulfonate, sodium laurate, sodium lauryl ether sulfate, sodium lauroyl sarcosinate, sodium myreth sulfate, sodium pareth sulfate, sodium stearate; cationic surfactants including benzalkonium chloride, benzethonium chloride, bronidox, cetrimonium bromide, cetrimonium chloride, distearyldimethylammonium chloride, lauryl methyl gluceth-10 hydroxypropyl dimonium chloride, octenidine dihydrochloride, olaflur, and tetramethylammonium hydroxide; and Zwitterionic surfactants including CHAPS detergent, cocamidopropyl betaine, cocamidopropyl hydroxysultaine, dipalmitoylphosphatidylcholine, lecithin, hydroxysultaine, and sodium lauroamphoacetate.

In some cases, the lysis buffer may contain an antifoaming agent for preventing or minimizing foaming. Non-limiting examples of antifoaming agents include Antifoam SE-15, Antifoam 204, Antifoam Y-30. In some cases, the lysis buffer may contain a preservative, for example an antimicrobial agent. Non-limiting examples of antimicrobials may include preservatives like ProClin™ 150, ProClin™ 200, ProClin™ 300, and ProClin™ 950.

In cases where the desired nucleic acid molecules are RNA, the lysis buffer may include one or more agents that prevent degradation of the RNA, such as, for example, an RNAse inhibitor. The volume of lysis buffer flowed over the membrane can be from about 10 µL to about 50 mL. For example, the volume of lysis buffer may be about 10 about 50 about 100 about 200 about 300 about 400 about 500 about 600 about 700 about 800 about 900 about 1 mL, about 5 mL, about 10 mL, about 15 mL, about 20 mL, about 25 mL, about 30 mL, about 35 mL, about 40 mL, about 45 mL, about 50 mL or greater than 50 mL.

In some cases, the lysis buffer contains one or more enzymes. In some cases, the one or more enzymes comprise Proteinase K. Proteinase K may be present in the lysis buffer at a concentration of about 0.001 mg/mL to about 10 mg/mL. For example, the concentration of proteinase K in the lysis buffer may be about 0.001 mg/mL, about 0.005 mg/mL, about 0.01 mg/mL, about 0.05 mg/mL, about 0.1 mg/mL, about 0.5 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL or greater than about 10 mg/mL. In some cases, the one or more enzymes comprise lysozyme to process gram-positive organisms. Lysozyme may be present in the lysis buffer at a concentration of about 0.001 mg/mL to about 10 mg/mL. For example, the concentration of lysozyme in the lysis buffer may be about 0.001 mg/mL, about 0.005 mg/mL, about 0.01 mg/mL, about 0.05 mg/mL, about 0.1 mg/mL, about 0.5 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL or greater than about 10 mg/mL. In some cases, the one or more enzymes comprise zymolyase to process yeast. Zymolase may be present in the lysis buffer at a concentration of about 0.001 mg/mL to about 10 mg/mL. For example, the concentration of zymolase in the lysis buffer may be about 0.001 mg/mL, about 0.005 mg/mL, about 0.01 mg/mL, about 0.05 mg/mL, about 0.1 mg/mL, about 0.5 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL or greater than about 10 mg/mL. Additional enzymes that may be used include, without limitation, lyticase, chitinase or gluculase, for e.g., the extraction of nucleic acids from yeast. In some examples, if more than one lysis enzyme is used, the enzymes may be added in sequence. For example, lysozyme may be added first, followed by an incubation period, and subsequently followed by addition of proteinase K and an additional incubation period. In some cases, the lysis buffer does not contain any enzymes.

In some aspects, the methods may involve one or more incubation steps. The one or more incubation steps may be performed in the lysis buffer in order to ensure complete lysis or disruption of the biological cell or entity and/or to destroy any inhibitory protein that may be present. The incubation step may involve holding the biological cell or entity in the lysis buffer for a period of time. In some cases, the incubation step involves holding the biological cell or entity in the lysis buffer for a period of time at a specified temperature. In a non-limiting example, the biological cell or entity is incubated in the lysis buffer from about 0.01 seconds to about 48 hours. For example, the biological cell or entity is incubated in the lysis buffer from about 0.01 seconds, about 0.05 seconds, about 1 second, about 10 seconds, about 30 seconds, about 1 minute, about 5 minutes, about 10 minutes, about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 48 hours, or greater than 48 hours. In some examples, the biological cell or entity is incubated in the lysis buffer at a specified temperature, for example, from about 4° C. to about 75° C. For example, the biological cell or entity is incubated in the lysis buffer at a temperature of about 4° C., about 10° C., about 15° C., about 20° C., about 25° C., about 30° C., about 40° C., about 45° C., about 50° C., about 55° C., about 60° C., about 65° C., about 70° C., about 75° C. or greater than 75° C. Generally, the temperature conditions will be selected so as to promote disruption of the biological cell or entity. For example, if the lysis buffer contains an enzyme (e.g., Proteinase K), the temperature may be selected such that the enzyme retains catalytic activity. In some cases, the temperature may be selected for optimal catalytic activity of the lysis enzyme. The temperature may also be selected to neutralize any inhibitory proteins within the sample, but should not destroy or disrupt the integrity of the nucleic acid molecules released therefrom. In some cases, the lysis buffer does not contain any enzymes.

The presence of one or more components (e.g., Proteinase K) in the lysis buffer may affect or interfere with downstream applications. In some cases, an additional incubation step may be performed to, for example, destroy or inactivate the one or more interfering components (e.g., Proteinase K) used in the lysis step. The subsequent incubation step may be from about 0.01 seconds to about 48 hours. For example, the biological cell or entity is incubated in the lysis buffer from about 0.01 seconds, about 0.05 seconds, about 1 second, about 10 seconds, about 30 seconds, about 1 minute, about 5 minutes, about 10 minutes, about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 48 hours, or greater than 48 hours. In some examples, the additional incubation step may occur at a temperature between about 57° C. and about 100° C. For example, the additional incubation step may occur at a temperature of about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C. or greater than 100° C.

In some aspects, the extracted nucleic acids may be utilized at this stage for any downstream processes, without any purification steps. In some cases, the extracted nucleic acid molecules may be used in one or more amplification reactions. For example, the extracted nucleic acid molecules may be used in one or more polymerase chain reactions (PCR). In the case where RNA is extracted, the RNA may be reverse transcribed (i.e., using a reverse transcriptase) prior to performing the downstream application. Any known method of PCR may be performed using the extracted nucleic acid molecules provided herein.

Biological Samples

In some cases, the biological sample can be a tissue sample. In some cases, the tissue sample is a blood sample. In some cases, the biological sample comprises a bodily fluid taken from a subject. In some cases, the bodily fluid comprises one or more cells comprising nucleic acids. In some cases, the one or more cells comprise one or more microbial cells, including, but not limited to, bacteria, archaebacteria, protists, and fungi. In some cases, the biological sample includes one or more virus particles. In some cases, the biological sample comprises one or more microbes that causes a sexually-transmitted disease. A sample may comprise a sample from a subject, such as whole blood; blood products; red blood cells; white blood cells; buffy coat; swabs; urine; sputum; saliva; semen; lymphatic fluid; endolymph; perilymph; gastric juice; bile; mucus; sebum; sweat; tears; vaginal secretion; vomit; feces; breast milk; cerumen; amniotic fluid; cerebrospinal fluid; peritoneal effusions; pleural effusions; biopsy samples; fluid from cysts; synovial fluid; vitreous humor; aqueous humor; bursa fluid; eye washes; eye aspirates; plasma; serum; pulmonary lavage; lung aspirates; animal, including human, tissues, including but not limited to, liver, spleen, kidney, lung, intestine, brain, heart, muscle, pancreas, cell cultures, as well as lysates, extracts, or materials and fractions obtained from the samples described above or any cells and microorganisms and viruses that may be present on or in a sample. A sample may comprise cells of a primary culture or a cell line. Examples of cell lines include, but are not limited to 293-T human kidney cells, A2870 human ovary cells, A431 human epithelium, B35 rat neuroblastoma cells, BHK-21 hamster kidney cells, BR293 human breast cells, CHO chinese hamster ovary cells, CORL23 human lung cells, HeLa cells, or Jurkat cells. The sample may comprise a homogeneous or mixed population of microbes, including one or more of viruses, bacteria, protists, monerans, chromalveolata, archaea, or fungi. The biological sample can be a urine sample, a vaginal swab, a cervical swab, an anal swab, or a cheek swab. The biological sample can be obtained from a hospital, laboratory, clinical or medical laboratory. The sample can be obtained from a subject.

Non-limiting examples of sample sources include environmental sources, industrial sources, one or more subjects, and one or more populations of microbes. Examples of environmental sources include, but are not limited to agricultural fields, lakes, rivers, water reservoirs, air vents, walls, roofs, soil samples, plants, and swimming pools. Examples of industrial sources include, but are not limited to clean rooms, hospitals, food processing areas, food production areas, food stuffs, medical laboratories, pharmacies, and pharmaceutical compounding centers. Examples of subjects from which polynucleotides may be isolated include multicellular organisms, such as fish, amphibians, reptiles, birds, and mammals. Examples of mammals include primates (e.g., apes, monkeys, gorillas), rodents (e.g., mice, rats), cows, pigs, sheep, horses, dogs, cats, or rabbits. In some examples, the mammal is a human. In some cases, the sample is from an individual subject.

In some cases, the biological sample is provided in a sample buffer. In some cases, the sample buffer comprises bovine serum albumin and/or a detergent. In some cases, the sample buffer comprises about 0.1% to 5% bovine serum albumin. In some cases, the sample buffer comprises about 0.1%, 0.2%, 0.3%, 0.4%, 0.5%, 1%, 1.5%, 2%, 2.5%, 3%, 4%, or 5% bovine serum albumin. In some cases, the sample buffer comprises about 0.1% to 20% detergent. In some cases, the sample buffer comprises about 1%, 2%, 3%, 4%, 5%, 6%, 7%, 8%, 9%, or 10% detergent. In some cases, the detergent is Tween-20. The choice of sample buffer to be used may depend on the intended method. For example the choice of sample buffer may different when a wash step will be used to when a wash step is not used. If a wash step will not be used then the sample buffer may be a buffer suitable for lysis and subsequent PCR reactions.

Some commercial collection mediums or sample buffers contain chemicals for the preservation of microorganisms for future growth, or chemicals that lyse target organisms such as guanidinium thiocyanate. As such, these collection media are inhibitory to DNA polymerase and must be washed from a sample before PCR via filtration or similar process. The methods described herein may not require the target organism to be kept in a viable state, or for the sample buffer to be able to lyse the cells. Some components which may be found in a sample buffer suitable for use with the methods and devices of this disclosure include: Tris HCL, Tween-80, BSA, Proclin and Antifoam SE-15. In one embodiment a sample buffer may have a composition of: 50 mM Tris pH 8.4, Tween-80, 2% (w/v), BSA, 0.25% (w/v), Proclin 300 0.03% (w/v), and Antifoam SE-15, 0.002% (v/v) made up in purified water.

Tris HCL is a common buffer for PCR. When it is heated during thermocycling, the pH may drop, for example a Tris buffer with pH of 8.4 at a temperature of 25° C. may drop to a pH of about ~7.4 when heated to about 95° C. The range of concentrations could be from 0.1 mM to 1 M. The pH range could be from 6 to 10. Any other PCR compatible buffer could be used, for example HEPES.

Tween-80 is a nonionic surfactant and emulsifier that may help to elute target organisms off of a swab. The range of concentrations could be from 0.01% (w/v) to 20% (w/v). Any other PCR compatible surfactant and/or emulsifier could be used.

Proclin 300 is a broad spectrum antimicrobial used as a preservative to ensure a long shelf life of the collection media. It could be used from 0.01% (w/v) to 0.1% (w/v). Many other antimicrobials are known in the art and could be used in a sample buffer.

Antifoam SE-15 is present to reduce foaming during manufacturing and fluidic movement through the device. It could be used from 0.001% (v/v) to 1% (v/v). Any other antifoam agent could also be used, for example Antifoam 204, Antifoam A, Antifoam B, Antifoam C, or Antifoam Y-30.

The devices and methods provided herein may be utilized to prepare nucleic acids for downstream applications. The downstream applications may be utilized to, e.g., detect the presence or absence of a nucleic acid sequence present in the sample. In some instances, the devices and methods can be utilized to detect the presence or absence of one or more microbes in a biological sample. In some cases, the one or more microbes are pathogens (i.e., disease-causative). In some cases, the one or more microbes are infectious. In some cases, the one or more microbes cause disease in a subject. In some cases, the disease is a sexually transmitted disease.

In some aspects, the devices and methods can be utilized to detect the presence or absence of nucleic acids associated with one or more bacterial cells in the biological sample. In some cases, one or more bacterial cells are pathogens. In some cases, the one or more bacterial cells are infectious. Non-limiting examples of bacterial pathogens that can be detected include Mycobacteria (e.g. *M. tuberculosis, M. bovis, M. avium, M. leprae*, and *M. africanum*), rickettsia, mycoplasma, chlamydia, and *legionella*. Some examples of bacterial infections include, but are not limited to, infections caused by Gram positive *bacillus* (e.g., *Listeria, Bacillus* such as *Bacillus anthracis, Erysipelothrix* species), Gram negative *bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio* and *Yersinia*

*species*), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, and *Neisseria* species. Specific examples of infectious bacteria include, but are not limited to: *Helicobacter pyloris, Legionella pneumophilia, Mycobacterium tuberculosis, Mycobacterium avium, Mycobacterium intracellulare, Mycobacterium kansaii, Mycobacterium gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, Erysipelothrix rhusiopathiae, Clostridium tetani, Enterobacter aerogenes, Klebsiella pneumoniae, Pasturella multocida, Fusobacterium nucleatum, Streptobacillus moniliformis, Treponema pallidium, Treponema pertenue, Leptospira, Rickettsia,* and *Actinomyces israelii, Acinetobacter, Bacillus, Bordetella, Borrelia, Brucella, Campylobacter, Chlamydia, Chlamydophila, Clostridium, Corynebacterium, Enterococcus, Haemophilus, Helicobacter, Mycobacterium, Mycoplasma, Stenotrophomonas, Treponema, Vibrio, Yersinia, Acinetobacter baumanii, Bordetella pertussis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Corynebacterium diphtheriae, Enterobacter sazakii, Enterobacter agglomerans, Enterobacter cloacae, Enterococcus faecalis, Enterococcus faecium, Escherichia coli, Francisella tularensis, Helicobacter pylori, Legionella pneumophila, Leptospira interrogans, Mycobacterium leprae, Mycobacterium tuberculosis, Mycobacterium ulcerans, Mycoplasma pneumoniae, Pseudomonas aeruginosa, Rickettsia rickettsii, Salmonella typhi, Salmonella typhimurium, Salmonella enterica, Shigella sonnei, Staphylococcus epidermidis, Staphylococcus saprophyticus, Stenotrophomonas maltophilia, Vibrio cholerae, Yersinia pestis,* and the like. In some instances, the infectious bacteria is *Neisseria gonorrhoeae* or *Chlamydia trachomatis*.

In some aspects, the devices and methods can be utilized to detect the presence or absence of nucleic acids associated with one or more viruses in the biological sample. Non-limiting examples of viruses include the herpes virus (e.g., human cytomegalomous virus (HCMV), herpes simplex virus 1 (HSV-1), herpes simplex virus 2 (HSV-2), varicella zoster virus (VZV), Epstein-Barr virus), influenza A virus and Hepatitis C virus (HCV) or a picornavirus such as Coxsackievirus B3 (CVB3). Other viruses may include, but are not limited to, the hepatitis B virus, HIV, poxvirus, hepadavirus, retrovirus, and RNA viruses such as flavivirus, togavirus, coronavirus, Hepatitis D virus, orthomyxovirus, paramyxovirus, rhabdovirus, bunyavirus, filo virus, Adenovirus, Human herpesvirus, type 8, Human papillomavirus, BK virus, JC virus, Smallpox, Hepatitis B virus, Human bocavirus, Parvovirus B19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, and Human immunodeficiency virus (HIV). In some cases, the virus is an enveloped virus. Examples include, but are not limited to, viruses that are members of the hepadnavirus family, herpesvirus family, iridovirus family, poxvirus family, flavivirus family, togavirus family, retrovirus family, coronavirus family, Filovirus family, rhabdovirus family, bunyavirus family, orthomyxovirus family, paramyxovirus family, and arenavirus family. Other examples include, but are not limited to, Hepadnavirus hepatitis B virus (HBV), woodchuck hepatitis virus, ground squirrel (Hepadnaviridae) hepatitis virus, duck hepatitis B virus, heron hepatitis B virus, Herpesvirus herpes simplex virus (HSV) types 1 and 2, varicella-zoster virus, cytomegalovirus (CMV), human cytomegalovirus (HCMV), mouse cytomegalovirus (MCMV), guinea pig cytomegalovirus (GPCMV), Epstein-Barr virus (EBV), human herpes virus 6 (HHV variants A and B), human herpes virus 7 (HHV-7), human herpes virus 8 (HHV-8), Kaposi's sarcoma—associated herpes virus (KSHV), B virus Poxvirus vaccinia virus, variola virus, smallpox virus, monkeypox virus, cowpox virus, camelpox virus, ectromelia virus, mousepox virus, rabbitpox viruses, raccoonpox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, Yabapox virus, Flavivirus dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus, Togavirus, Venezuelan equine encephalitis (VEE) virus, chikungunya virus, Ross River virus, Mayaro virus, Sindbis virus, rubella virus, Retrovirus human immunodeficiency virus (HIV) types 1 and 2, human T cell leukemia virus (HTLV) types 1, 2, and 5, mouse mammary tumor virus (MMTV), Rous sarcoma virus (RSV), lentiviruses, Coronavirus, severe acute respiratory syndrome (SARS) virus, Filovirus Ebola virus, Marburg virus, Metapneumoviruses (MPV) such as human metapneumovirus (HMPV), Rhabdovirus rabies virus, vesicular stomatitis virus, Bunyavirus, Crimean-Congo hemorrhagic fever virus, Rift Valley fever virus, La Crosse virus, Hantaan virus, Orthomyxovirus, influenza virus (types A, B, and C), Paramyxovirus, parainfluenza virus (PIV types 1, 2 and 3), respiratory syncytial virus (types A and B), measles virus, mumps virus, Arenavirus, lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Punta toro virus (PTV), Tacaribe virus and Tamiami virus. In some embodiments, the virus is a non-enveloped virus, examples of which include, but are not limited to, viruses that are members of the parvovirus family, circovirus family, polyoma virus family, papillomavirus family, adenovirus family, iridovirus family, reovirus family, birnavirus family, calicivirus family, and picornavirus family. Specific examples include, but are not limited to, canine parvovirus, parvovirus B19, porcine circovirus type 1 and 2, BFDV (Beak and Feather Disease virus, chicken anaemia virus, Polyomavirus, simian virus 40 (SV40), JC virus, BK virus, Budgerigar fledgling disease virus, human papillomavirus, bovine papillomavirus (BPV) type 1, cotton tail rabbit papillomavirus, human adenovirus (HAdV-A, HAdV-B, HAdV-C, HAdV-D, HAdV-E, and HAdV-F), fowl adenovirus A, bovine adenovirus D, frog adenovirus, Reovirus, human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, idnoreovirus 1, mycoreovirus 1, Birnavirus, bursal disease virus, pancreatic necrosis virus, Calicivirus, swine vesicular exanthema virus, rabbit hemorrhagic disease virus, Norwalk virus, Sapporo virus, Picornavirus, human polioviruses (1-3), human coxsackieviruses A1-22, 24 (CA1-22 and CA24, CA23 (echovirus 9)), human coxsackieviruses (Bl-6 (CB1-6)), human echoviruses 1-7, 9, 11-27, 29-33, vilyuish virus, simian enteroviruses 1-18 (SEV1-18), porcine enteroviruses 1-11 (PEV1-11), bovine enteroviruses 1-2 (BEV1-2), hepatitis A virus, rhinoviruses, hepatoviruses, cardio viruses, aphthoviruses and echoviruses. The virus may be phage. Examples of phages include, but are not limited to T4, T5, λphage, T7 phage, G4, P1, φ6, *Thermoproteus tenax* virus 1, M13, MS2, Qβ, φX174, Φ29, PZA, Φ15, BS32, B103, M2Y (M2), Nf, GA-1, FWLBc1, FWLBc2, FWLLm3, B4. The reference database may comprise sequences for phage that are pathogenic, protective, or both. In some cases, the virus is selected from a member of the Flaviviridae family (e.g., a member of the Flavivirus, Pestivirus, and Hepacivirus genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, and the Cell fusing agent virus. In some cases, the virus is selected from a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Whitewater Arroyo virus, Chapare virus, and Lujo virus. In some cases, the virus is selected from a member of the Bunyaviridae family (e.g., a member of the *Hantavirus, Nairovirus, Orthobunyavirus*, and *Phlebovirus* genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus. In some cases, the virus is selected from a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the Alphavirus genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O'nyong'nyong virus, and the chikungunya virus; a member of the Poxyiridae family (e.g., a member of the *Orthopoxvirus* genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively).

In some aspects, the devices and methods can be utilized to detect the presence or absence of nucleic acids associated with one or more fungi in the biological sample. Examples of infectious fungal agents include, without limitation *Aspergillus, Blastomyces, Coccidioides, Cryptococcus, Histoplasma, Paracoccidioides, Sporothrix*, and at least three genera of *Zygomycetes*. The above fungi, as well as many other fungi, can cause disease in pets and companion animals. The present teaching is inclusive of substrates that contact animals directly or indirectly. Examples of organisms that cause disease in animals include *Malassezia furfur, Epidermophyton floccosur, Trichophyton mentagrophytes, Trichophyton rubrum, Trichophyton tonsurans, Trichophyton equinum, Dermatophilus congolensis, Microsporum canis, Microsporu audouinii, Microsporum gypseum, Malassezia ovale, Pseudallescheria, Scopulariopsis, Scedosporium*, and *Candida albicans*. Further examples of fungal infectious agent include, but are not limited to, *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus*, or *Rhizopus arrhizus*.

In some aspects, the devices and methods can be utilized to detect the presence or absence of nucleic acids associated with one or more parasites in the biological sample. Non-limiting examples of parasites include *Plasmodium, Leishmania, Babesia, Treponema, Borrelia, Trypanosoma, Toxoplasma gondii, Plasmodium falciparum, P. vivax, P. ovale, P. malariae, Trypanosoma* spp., or *Legionella* spp. In some cases, the parasite is *Trichomonas vaginalis*.

In some cases, the biological sample can be an environmental sample comprising medium such as water, soil, air, and the like. In some cases, the biological sample can be a forensic sample (e.g., hair, blood, semen, saliva, etc.). In some cases, the biological sample can comprise an agent used in a bioterrorist attack (e.g., influenza, anthrax, smallpox).

In some aspects, the biological sample comprises an infectious agent associated with a sexually-transmitted disease (STD) or a sexually-transmitted infection (STI). Non-limiting examples of STDs or STIs and associated infectious agents that may be detected with the devices and methods provided herein may include, Bacterial Vaginosis; Chlamydia (*Chlamydia trachomatis*); Genital herpes (herpes virus); Gonorrhea (*Neisseria gonorrhoeae*); Hepatitis B (Hepatitis B virus); Hepatitis C (Hepatitis C virus); Genital Warts, Anal Warts, Cervical Cancer (Human Papillomavirus); Lymphogranuloma venereum (*Chlamydia trachomatis*); Syphilis (*Treponema pallidum*); Trichomoniasis (*Trichomonas vaginalis*); Yeast infection (*Candida*); and Acquired Immunodeficiency Syndrome (Human Immunodeficiency Virus).

Performance

In some cases, the devices and methods described herein may demonstrate improved performance when compared with traditional methods. For example, in some cases, the devices and methods may result in the extraction and preparation of nucleic acid molecules suitable for use in a polymerase chain reaction (PCR) in a shorter period of time when compared with other methods. In some cases, the devices and methods may result in the extraction and preparation of nucleic acid molecules suitable for use in a PCR reaction in 20 minutes or less. For example, the extraction and preparation of nucleic acid molecules as described herein may be achieved in about 20 minutes, 19 minutes, 18 minutes, 17 minutes, 16 minutes, 15 minutes, 14 minutes, 13 minutes, 12 minutes, 11 minutes, 10 minutes, 9 minutes, 8 minutes, 7 minutes, 6 minutes, 5 minutes, 4 minutes, 3 minutes, 2 minutes, 1 minute or less than 1 minute. In some cases, the extraction and preparation of nucleic acid molecules as described herein is achieved in about 5 minutes or less. In some cases, the method extracts nucleic acid molecules in about 5 minutes or less at a quality sufficient to successfully run a polymerase chain reaction (PCR).

A quality of extracted nucleic acid sufficient to run a polymerase chain reaction refers to the quantity of extracted nucleic acid, the purity of the nucleic acid and the shearing of the nucleic acid (average length of nucleic acid molecules). A sufficient quantity of nucleic acid may refer to about 0.001, 0.01, 0.05, 0.1, 0.2, 0.3, 0.4, 0.5, 0.6, 0.7, 0.8, 0.9, or 1 µg. A sufficient quantity may also refer to the concentration of the nucleic acid in the eluted liquid. The concentration of the eluted nucleic acid may be about 0.001, 0.01, 0.05, 0.1, 0.2, 0.3, 0.4, 0.5, 0.6, 0.7, 0.8, 0.9 or 1 µg/µL. The nucleic acid produced may comprise nucleic acid fragments with an average length of at least about 100, 200, 300, 400, 500, 600, 700, 800, 900, 1000 or more than 1000 base pairs.

A quality of extracted nucleic acid sufficient to run a polymerase chain reaction may be a sample that produces at least 70% efficiency as determined by a qPCR standard curve. The efficiency of the PCR may be between 90-100% ($-3.6 \geq \text{slope} \geq -3.3$). Efficiency of qPCR may be quantified by calculating the cycle difference between a sample and 10-fold dilution of the sample. For example if the efficiency is 100%, the Ct values of a 10 fold dilution of input DNA will be 3.3 cycles apart (there is a 2-fold change for each change in Ct).

In some cases, the nucleic acid sample prepared using the devices and methods described herein have similar or improved purity as compared to nucleic acid samples prepared using other methods. The purity may be measured, for example, as a ratio of the absorbance at 260 nm and 280 nm (e.g., A260/A280). For example, a nucleic acid samples comprising DNA prepared using the devices and methods may have a A260/A280 ratio of about 1.5, about 1.6, about 1.7, about 1.8, about 1.9, or about 2.0. In some cases, the extracted nucleic acid molecules comprise DNA and the DNA has an A260/A280 ratio of at least 1.5. In another example, a nucleic acid sample comprising RNA prepared using the devices and methods may have an A260/A280 ratio of about 1.7, about 1.8, about 1.9, about 2.0, about 2.1, or about 2.2. In some cases, the extracted nucleic acid molecules comprise RNA and the RNA has an A260/A280 ratio of at least 1.7.

Downstream processes such as polymerase chain reaction (PCR) may be sensitive to certain molecules present in a sample. For example, the presence of one or more lysis reagents (e.g., Proteinase K) may hinder or inhibit downstream processes. In some cases, the nucleic acid molecules described herein are extracted from the one or more biological cells or entities with a quality that is sufficient to successfully perform one or more downstream processes. In some cases, the extracted nucleic acid molecules may be of a quality sufficient to successfully perform a PCR. For example, the extracted nucleic acid molecules may be of a quality sufficient to perform an amplification reaction on a target nucleic acid molecule present in the extracted nucleic acid molecules to generate amplified target nucleic molecules. In some cases, a positive control may be used (e.g., a biological cell that is known to be positive for the target molecule) to confirm that the extraction process is performed successfully. The extracted nucleic acid molecules described herein are generally substantially free of molecules that inhibit downstream processes (e.g., Proteinase K).

In some cases, the nucleic acid samples may have similar or improved yields as compared to nucleic acid samples prepared using other methods from the same amount of starting material. For example, nucleic acid samples prepared using the methods and devices described herein may have about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or greater yields than using other nucleic acid extraction methods from the same amount of starting material.

Standard nucleic acid extraction methods may involve the use of centrifuges and vacuums. In some cases, the methods and devices herein do not involve the use of centrifuges or vacuums.

Devices

Figure 10:
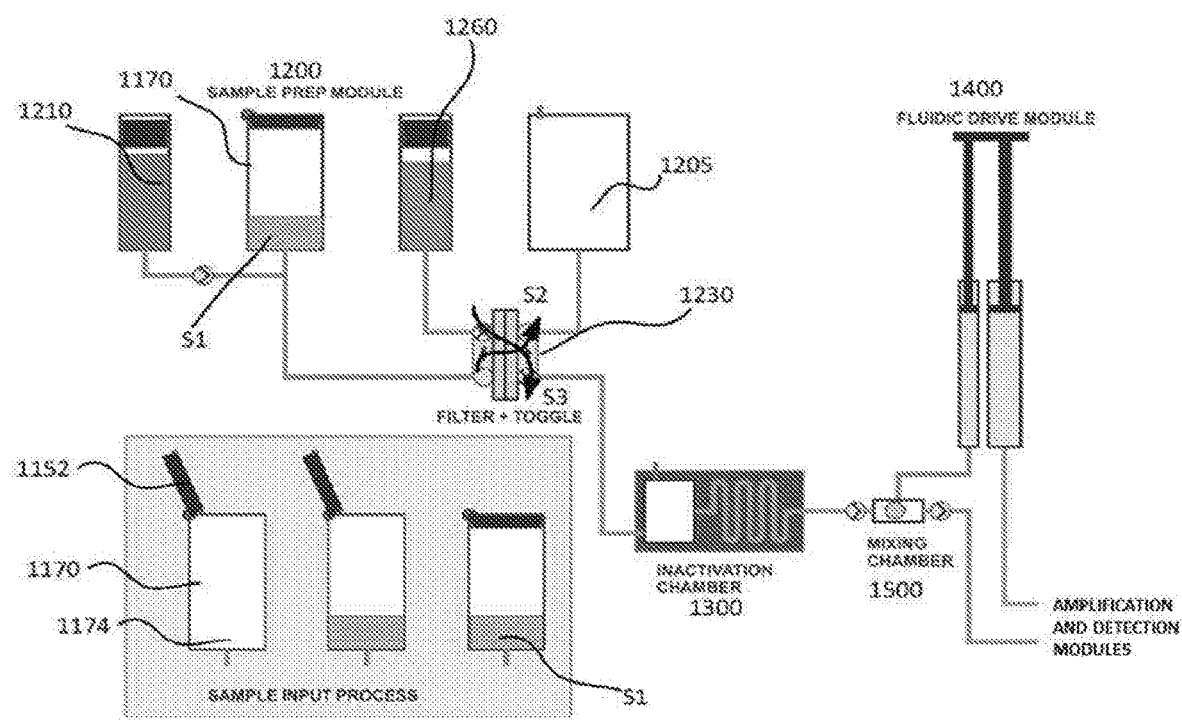
FIG. 10 is a schematic illustration of a molecular diagnostic test device, according to an embodiment, which can perform the methods described herein.
Figure 11:
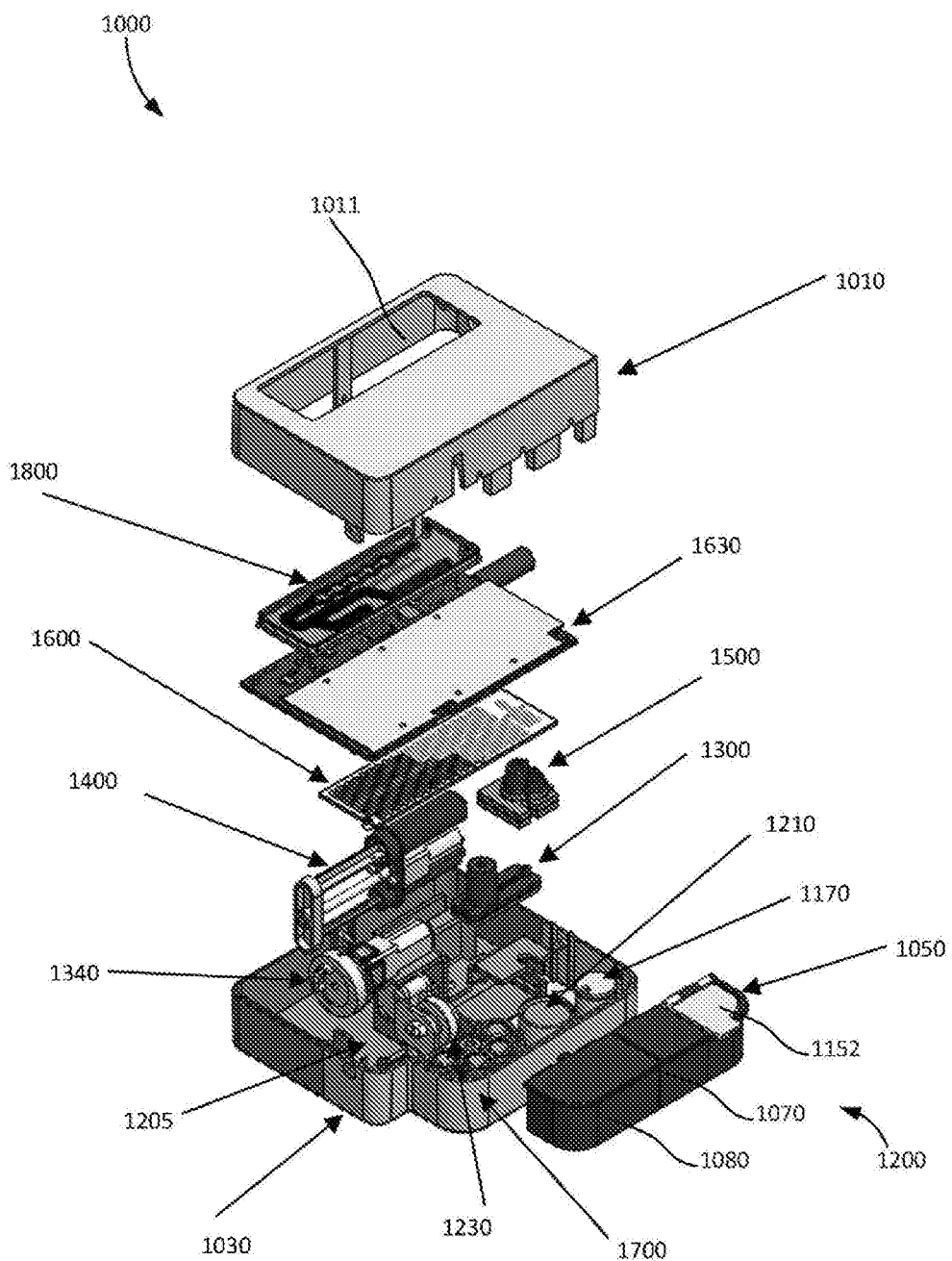
FIG. 11 is an exploded view of the molecular diagnostic test device shown schematically in FIG. 10.

In some aspects, devices are provided for performing any of the methods described herein. For example, FIG. 10 is a schematic illustration of a molecular diagnostic test device 1000 (also referred to as a "test device" or "device"), according to an embodiment. The schematic illustration describes the primary components of the test device 1000 as shown in FIG. 11. The test device 1000 is an integrated device (i.e., the modules are contained within a single housing) that is suitable for use within a point-of-care setting (e.g., doctor's office, pharmacy or the like), decentralized test facility, or at the user's home. In some embodiments, the device 1000 can have a size, shape and/or weight such that the device 1000 can be carried, held, used and/or manipulated in a user's hands (i.e., it can be a "handheld" device). A handheld device may have dimensions less than 15 cm×15 cm×15 cm, or less than 15 cm×15 cm×10 cm, or less than 12 cm×12 cm×6 cm. In other embodiments, the test device 1000 can be a self-contained, single-use device. In some embodiments, the test device 1000 can be configured with lock-outs or other mechanisms to prevent re-use or attempts to re-use the device.

Further, in some embodiments, the device 1000 can be a CLIA-waived device and/or can operate in accordance with methods that are CLIA waived. Similarly stated, in some embodiments, the device 1000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 1000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 1000 can be configured for long term storage in a manner that poses a limited likelihood of misuse (spoilage of the reagent(s), expiration of the reagents(s), leakage of the reagent(s), or the like). In some embodiments, the molecular diagnostic test device 1000 is configured to be stored for up to about 36 months, up to about 32 months, up to about 26 months, up to about 24 months, up to about 20 months, up to about 18 months, or any values there between.

The test device 1000 is configured to manipulate a biological sample S1 to produce one or more output signals associated with a target cell. Specifically, the device 1000 includes a sample preparation module 1200, an inactivation module 1300 (also referred to as a lysing module), a fluidic drive (or fluid transfer) module 1400, a mixing chamber 1500, an amplification module, a detection module and a power and control module (not shown). The test device and certain components therein can be similar to any of the molecular test devices shown and described herein or in International Patent Publication No. WO2016/109691, entitled "Devices and Methods for Molecular Diagnostic Testing," which is incorporated herein by reference in its entirety. Accordingly, a detailed description of certain modules (e.g., the fluidic drive module 1400) is not provided herein. A description of each of the modules is provided below.

FIG. 11 shows a perspective exploded view of the molecular diagnostic test device 1000. The diagnostic test device 1000 includes a housing (including a top portion 1010 and a bottom portion 1030), within which the modules described herein are contained. Similarly stated, the housing (including the top portion 1010 and/or the bottom portion 1030) surround and/or enclose the modules. As shown, the top housing 1010 defines a detection opening 1011 that is aligned with the detection module 1800 such that the signal produced by and/or on each detection surface of the detection module 1800 is visible through the detection opening 1011. In some embodiments, the top housing 1010 and/or the portion of the top housing 1010 surrounding the detection opening 1011 is opaque (or semi-opaque), thereby "framing" or accentuating the detection openings. In some embodiments, for example, the top housing 1010 can include markings (e.g., thick lines, colors or the like) to highlight the detection opening 1011. For example, in some embodiments, the top housing 1010 can include indicia identifying the detection opening to a specific disease (e.g., *Chlamydia trachomatis* (CT), *Neisseria gonorrhea* (NG) and *Trichomonas vaginalis* (TV)) or control. In other embodiments, the top housing 1010 can include a series of color spots having a range of colors associated with a range of colors that is likely produced by the signals produced during the test. In this manner, the housing design can contribute to reducing the amount of user judgment required to accurately read the test.

Referring to FIG. 11, the sample preparation module 1200 includes a sample input module 1170, a wash module 1210, an elution module 1260, a filter assembly 1230, and various fluidic conduits (e.g., tubes, lines, valves, etc.) connecting the various components. The device 1000 also includes the lysing module 1300 (see e.g., the lysing module 2300 shown in FIGS. 13-16), which, together with the sample preparation module 1200, performs the nucleic acid extraction according to any of the methods described herein. Thus, although the sample preparation module 1200 and the inactivation module 1300 are described as two separate modules, in other embodiments, the structure and function of the sample preparation module 1200 can be included within or performed by the inactivation module 1300 and vice-versa. Similarly stated, any of the sample preparation modules, inactivation modules and/or lysing modules described herein can include any of the structure and/or perform any of the functions of the other modules to perform any of the methods of sample preparation or nucleic acid extraction described herein. By eliminating the need for external sample preparation and a cumbersome instrument, the device 1000 is suitable for use within a point-of-care setting (e.g., doctor's office, pharmacy or the like) or at the user's home, and can receive any suitable biological sample S1. The biological sample S1 (and any of the input samples described herein) can be, for example, blood, urine, male urethral specimens, vaginal specimens, cervical swab specimens, and/or nasal swab specimens gathered using a commercially available sample collection kit.

The sample input module 1170 is disposed within the housing 1010, and is configured receive a biological sample S1 containing a biological entity. The biological sample S1 can be any of the sample types described herein, and the biological entity can be any of the entities described herein. The sample input module 1170 defines a sample volume 1174 that can be selectively covered by the cap 1152. The cap 1152 can include seals or other locking members such that it can be securely fastened to the lower housing 1030 (or other portions of the device 1000) and/or can be closed during shipping, after delivery of a sample thereto, or the like. In some embodiments, the input port cap 1152 can include an irreversible lock to prevent reuse of the device 1000 and/or the addition of supplemental sample fluids. In this manner, the device 1000 can be suitably used by untrained individuals.

The wash module 1210 includes a housing that defines a wash volume containing any suitable wash composition. For example, in some embodiments, the wash module 1210 can include a gaseous first wash composition (e.g., nitrogen, air, or another inert gas) and a liquid second wash composition. In this manner, the wash operation can include an "air purge" of the filter assembly 1230. Specifically, when the sample input module 1170 and/or the wash module 1210 is actuated, a serial flow of the first wash composition (gas) followed by the second wash composition (liquid). By first including a gas (or air) wash (i.e., the first wash composition), the amount of liquid constituents from the input sample conveyed to the filter assembly 1230 (indicated by the flow S2 in FIG. 10) can be reduced. Said another way, after delivery of the input sample, the filter assembly 1230 will retain the desired sample cells (or organisms) and some amount of residual liquid. By forcing the first, gaseous wash composition through the filter (i.e., an "air wash"), the amount of residual liquid can be minimized. This arrangement can reduce the amount of liquid wash (e.g., the second wash composition) needed to sufficiently prepare the sample particles. Reducing the liquid volume contributes to the reduction size of the device 1000, and also reduces the likelihood of potentially harmful shearing stress when the liquid wash is flowed through the filter assembly 1230.

The sample input module 1170 (and any of the sample input modules described herein) and the wash module 1210 (and any of the wash modules described herein) can be actuated by any suitable mechanism to convey the biological sample S1 towards the filter assembly 1230 and/or the lysing module 1300 to enable the nucleic acid extraction methods described herein. For example, in the embodiment shown, the sample input module 1170 and the wash module 1210 are actuated by the sample actuator (or button) 1050. The sample actuator 1050 is movably coupled to the housing, and is aligned with and can move a piston or plunger (not shown) within the sample volume 1174 when the sample input module 1170 is actuated. Thus, the sample actuator 1050 is a non-electronic actuator that is manually depressed by a user to actuate the sample input module 1170. In other embodiments, however, the sample actuator 1050 can be an electronic actuator. In some embodiments, the sample actuator 1050 can include a lock tab (not shown) that is fixedly received within the notch or opening of the housing 1010 to fix the sample actuator 1050 in its second or "actuated" position, as described above. In this manner, the device 1000 cannot be reused after the initial actuation.

When actuated, the sample within the sample volume 1174 is conveyed along with the wash solution(s) from the wash module 1210 towards the filter assembly 1230. The flow of the biological sample S1 towards the filter assembly 1230 is shown by the arrow S2 in FIG. 10. The filter assembly 1230 is configured to filter and prepare the biological sample S1 (via the sample input operation and the sample wash operation), and to allow a back-flow elution operation to deliver captured particles from the filter membrane and deliver the eluted volume to lysing module 1300. The filter assembly 1230 can be toggled between two configurations to allow the flow of the biological sample S1 and wash solution in a first direction (towards the waste reservoir 1205), followed by a backflush of the elution reagent and the captured organisms (or cells) in a second direction (as indicated by the arrow S3 towards the lysing/inactivation module 1300). The toggling mechanism can be any suitable mechanism, such as those shown and described in International Patent Publication No. WO2016/109691, entitled "Devices and Methods for Molecular Diagnostic Testing," which is incorporated herein by reference in its entirety.

The filter assembly 1230 can include any suitable filter membrane that captures the target organism/entity while allowing the bulk of the liquid within the biological sample S1, the first wash composition, and the second wash composition to flow therethrough and into the waste tank 1205. The filter membrane 1254 (and any of the filter membranes described herein) can be any suitable membrane and or combination of membranes as described herein. For example, in some embodiments, the filter membrane 1254 is a woven nylon filter membrane with a pore size of about 1 µm (e.g., 0.8 µm, 1.0 µm, 1.2 µm) enclosed between various plates of the filter assembly 1230 such that there is minimal dead volume.

The elution module (or assembly) 1260 of the sample preparation module 1200 is contained within the housing, and defines an elution volume within which an elution composition is stored. The elution composition can be any of the elution compositions described herein. In some embodiments, the elution composition can include proteinase K, which allows for the release of any bound cells and/or nucleic acid molecules (e.g., DNA) from the filter membrane. The output from the elution module 1260 can be selectively placed in fluid communication with the filter assembly 1230, when the filter assembly is toggled into its second (or backflow) configuration. Thus, the elution module 1230 can include any suitable flow control devices, such as check valves, duck-bill valves, or the like to prevent flow back towards and/or into the elution volume.

The elution module 1210 is actuated by the elution actuator (or button) 1070 (see FIG. 11). The reagent actuator 1070 is movably coupled to the lower housing 1030, and can exert force on a piston or other portion of the elution module 1210 to convey the elution composition back through the filter and towards the lysing module 1300, as shown by the arrow S3. In some embodiments, the elution actuator 1070 further includes a lock tab or other structure that is fixedly received within the notch or opening of the housing to fix the elution actuator 1070 in its second or "actuated" position. In this manner, the device 1000 cannot be reused after the actuation of the elution actuator.

In use, the filter assembly 1230 recovers the target organisms with a certain efficiency, from a given starting volume. The wash operation then removes undesired material, without removing the target organisms (which stay present on the filter membrane). The elution operation then removes the target organism from the filter membrane, diluting the total amount of captured organisms in the volume of the elution solution, thus comprising the eluent. By modifying the total output volume of eluent, a higher or lower concentration of both target organism and any potential inhibiting matter can be achieved. In some embodiments, a further dilution can be achieved, if desired, by mixing the eluent solution with another reagent after the initial sample preparation. Given a known volume of eluent, and a known volume of diluent, a correct dilution factor can be achieved, through to maintain the reliability of the system very high dilution factors are avoided.

As shown by the arrow S3 in FIG. 10, the elution solution and the captured cells and/or organisms are conveyed during the elution operation back through the filter assembly 1230, and to the inactivation module (or lysing module) 1300. The inactivation module 1300 is configured to be fluidically coupled to and receive the eluted sample S3 from the sample preparation module 1200. In some embodiments, the inactivation module 1300 is configured for lysis of the received input fluid. In some embodiments, the inactivation module 1300 is configured for de-activating the enzymes present in input fluid after lysis occurs. In some embodiments, the inactivation module 1300 is configured for preventing cross-contamination between the output fluid and the input fluid. The inactivation module 1300 can include any of the inactivation (or lysing) modules as described herein, including the lysing module 3300 and the lysing module 4300 described herein.

The mixing module (also referred to as simply the mixing chamber) 1500 mixes the output of inactivation module 1300 with the reagents to conduct a successful amplification reaction. Similarly stated, the mixing module 1500 is configured to reconstitute the reagent in a predetermined input volume, while ensuring even local concentrations of reagents in the entirety of the volume. In some embodiments, the mixing chamber module 1500 is configured to produce and/or convey a sufficient volume of liquid for the amplification module 1600 to provide sufficient volume output to the detection module 1800. The mixing module 1500 can be any suitable mixing module, such as those shown and described in International Patent Publication No. WO2016/109691, entitled "Devices and Methods for Molecular Diagnostic Testing," which is incorporated herein by reference in its entirety.

The fluidic drive (or transfer) module 1400 can be a pump or series of pumps configured to produce a pressure differential and/or flow of the solutions within the diagnostic test device 1000. Similarly stated, the fluid transfer module 1400 is configured to generate fluid pressure, fluid flow and/or otherwise convey the biological sample S1, and the reagents through the various modules of the device 1000. The fluid transfer module 1400 is configured to contact and/or receive the sample flow therein. Thus, in some embodiments, the device 1000 is specifically configured for a single-use to eliminate the likelihood that contamination of the fluid transfer module 1400 and/or the sample preparation module 1200 will become contaminated from previous runs, thereby negatively impacting the accuracy of the results. The fluid transfer module 1500 can be any suitable fluid transfer module, such as those shown and described in International Patent Publication No. WO2016/109691, entitled "Devices and Methods for Molecular Diagnostic Testing," which is incorporated herein by reference in its entirety.

After being mixed within the mixing module 1500, the prepared sample is then conveyed to the amplification module 1600 (as shown by the arrow CC in FIG. 10). The amplification module 1600 includes a flow member 1610 and a heater 1630. The flow member 1610 can be any suitable flow member that defines a volume or a series of volumes within which the that prepared solution S3 can flow and/or be maintained to amplify the target nucleic acid molecules within the solution S3. The heater 1630 can be any suitable heater or group of heaters coupled to the flow member 1610 that can heat the prepared solution within the flow member 1610 to perform any of the amplification operations as described herein. For example, in some embodiments, the amplification module 1600 (or any of the amplification modules described herein) can be similar to the amplification modules shown and described in U.S. patent application Ser. No. 15/494,145, entitled "Printed Circuit Board Heater for an Amplification Module," which is incorporated herein by reference in its entirety. In other embodiments, the amplification module 1600 (or any of the amplification modules described herein) can be similar to the amplification modules shown and described in International Patent Publication No. WO2016/109691, entitled "Devices and Methods for Molecular Diagnostic Testing," which is incorporated herein by reference in its entirety.

In some embodiments, the flow member 1610 defines a single volume within which the prepared solution is maintained and heated to amplify the nucleic acid molecules within the prepared solution. In other embodiments, the flow member 1610 can define a "switchback" or serpentine flow path through which the prepared solution flows. Similarly stated, the flow member 1610 defines a flow path that is curved such that the flow path intersects the heater 1630 at multiple locations. In this manner, the amplification module 1600 can perform a "flow through" amplification reaction where the prepared solution flows through multiple different temperature regions.

The flow member 1610 (and any of the flow members described herein) can be constructed from any suitable material and can have any suitable dimensions to facilitate the desired amplification performance for the desired volume of sample. For example, in some embodiments, the amplification module 1600 (and any of the amplification modules described herein) can perform 1000× or greater amplification in a time of less than 15 minutes. For example, in some embodiments, the flow member 1610 (and any of the flow members described herein) is constructed from at least one of a cyclic olefin copolymer or a graphite-based material. Such materials facilitate the desired heat transfer properties into the flow path. Moreover, in some embodiments, the flow member 1610 (and any of the flow members described herein) can have a thickness of less than about 0.5 mm. In some embodiments, the flow member 1610 (and any of the flow members described herein) can have a volume about 150 microliters or greater, and the flow can be such that at least 10 microliters of sample is amplified. In other embodiments, at least 20 microliters of sample are amplified by the methods and devices described herein. In other embodiments, at least 30 microliters of sample are amplified by the methods and devices described herein. In yet other embodiments, at least 50 microliters of sample are amplified by the methods and devices described herein.

The heater 1630 can be any suitable heater or collection of heaters that can perform the functions described herein to amplify the prepared solution. In some embodiments, the heater 1630 can establish multiple temperature zones through which the prepared solution flows and/or can define a desired number of amplification cycles to ensure the desired test sensitivity (e.g., at least 30 cycles, at least 34 cycles, at least 36 cycles, at least 38 cycles, or at least 40 cycles). The heater 1630 (and any of the heaters described herein) can be of any suitable design. For example, in some embodiments, the heater 1630 can be a resistance heater, a thermoelectric device (e.g. a Peltier device), or the like. In some embodiments, the heater 1630 can be one or more linear "strip heaters" arranged such that the flow path crosses the heaters at multiple different points. In other embodiments, the heater 1630 can be one or more curved heaters having a geometry that corresponds to that of the flow member 1610 to produce multiple different temperature zones in the flow path.

Although the amplification module 1600 is generally described as performing a thermal cycling operation on the prepared solution, in other embodiment, the amplification module 1600 can perform any suitable thermal reaction to amplify nucleic acids within the solution. In some embodiments, the amplification module 1600 (and any of the amplification modules described herein) can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process The detection methods enabled by the device 1000 include sequential delivery of the detection reagents and other substances within the device 1000. Further, the device 1000 is configured to be an "off-the-shelf" product for use in a point-of-care location (or other decentralized location), and is thus configured for long-term storage. Accordingly, the reagent storage module 1700 is configured for simple, non-empirical steps for the user to remove the reagents from their long-term storage containers, and for removing all the reagents from their storage containers using a single user action. In some embodiments, the reagent storage module 1700 and the rotary selection valve 1340 are configured for allowing the reagents to be used in the detection module 1800, one at a time, without user intervention.

Specifically, the device 1000 is configured such that the last step of the initial user operation (i.e., the depressing of the reagent actuator 1080) results in dispensing the stored reagents. This action crushes and/or opens the sealed reagent containers present in the assembly and relocates the liquid for delivery. The rotary venting selector valve 1340 allows the reagent module 1700 to be vented for this step, and thus allows for opening of the reagent containers, but closes the vents to the tanks once this process is concluded. Thus, the reagents remain in the reagent module 1700 until needed in the detection module 1800. When a desired reagent is needed, the rotary valve 1340 opens the appropriate vent path to the reagent module 1700, and the fluidic drive module 1400 applies vacuum to the output port of the reagent module 1700 (via the detection module 1800), thus conveying the reagents from the reagent module 1700. The reagent module 1700 and the valve 1340 can be similar to the reagent modules and valves shown and described in International Patent Publication No. WO2016/109691, entitled "Devices and Methods for Molecular Diagnostic Testing," which is incorporated herein by reference in its entirety.

The detection module 1800 is configured to receive output from the amplification module 1600 and reagents from the reagent module 1700 to produce a colorimetric change to indicate presence or absence of target organism in the initial input sample. The detection module 1800 also produces a colorimetric signal to indicate the general correct operation of the test (positive control and negative control). In some embodiments, color change induced by the reaction is easy to read and binary, with no requirement to interpret shade or hue. The detection module 1800 can be similar to the detection modules shown and described in International Patent Publication No. WO2016/109691, entitled "Devices and Methods for Molecular Diagnostic Testing," which is incorporated herein by reference in its entirety.

In one aspect, a device is provided comprising: (a) an input port, configured to receive the biological sample comprising one or more biological cells or biological entities; (b) a filter assembly comprising a filter configured to capture the one or more biological cells or biological entities, wherein the input port is configured to relay the biological sample to the filter assembly; (c) one or more reservoirs comprising a wash solution, a lysis solution, or both, operably coupled to the filter assembly; (d) a waste chamber, operably coupled to the filter assembly and configured to receive waste from the filter assembly; and (e) an elution chamber, operably coupled to the filter assembly and configured to receive an eluent from the filter assembly.

Figure 12:
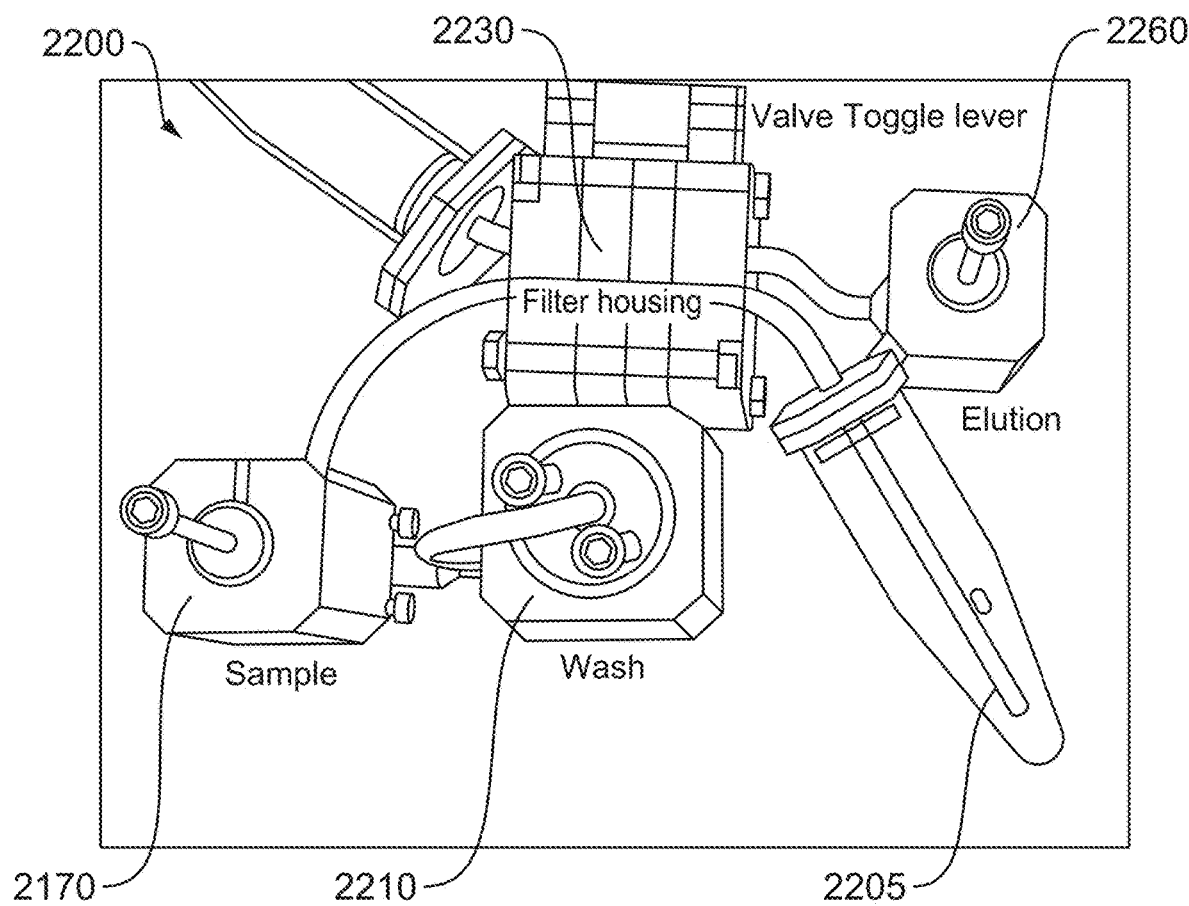
FIG. 12 depicts an example of a sample preparation device amenable to performing the methods as described herein.
Figure 13:
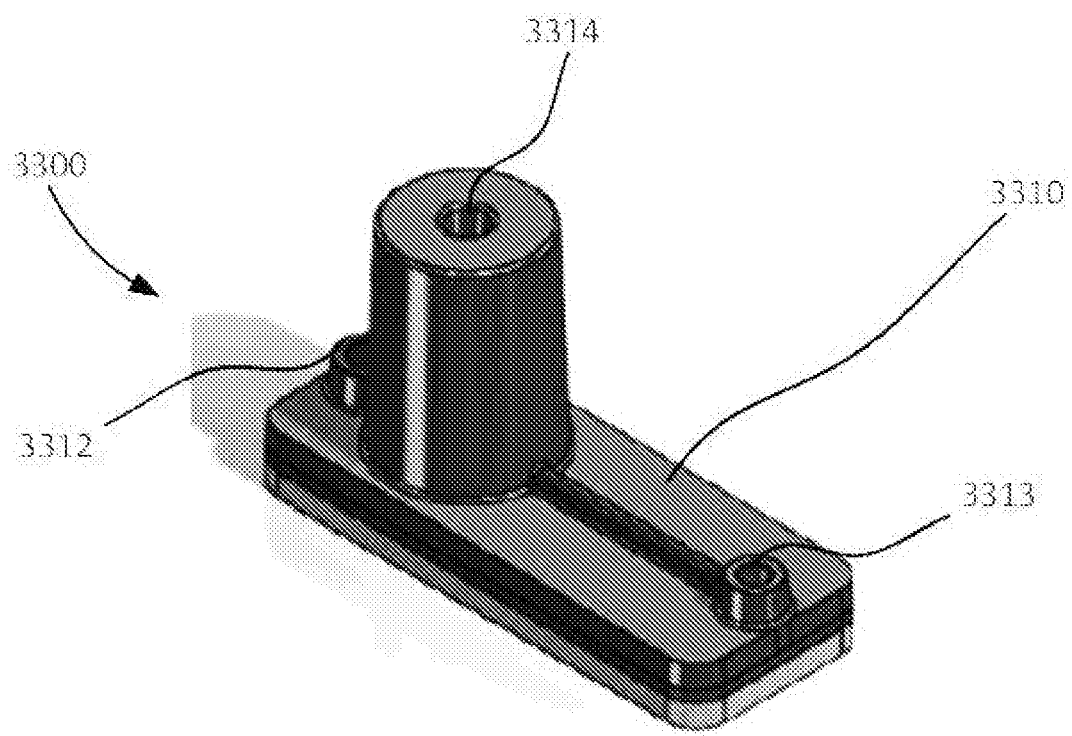
FIG. 13 is a perspective view of a lysing module according to an embodiment, which is amenable to performing the methods as described herein.
Figure 14:
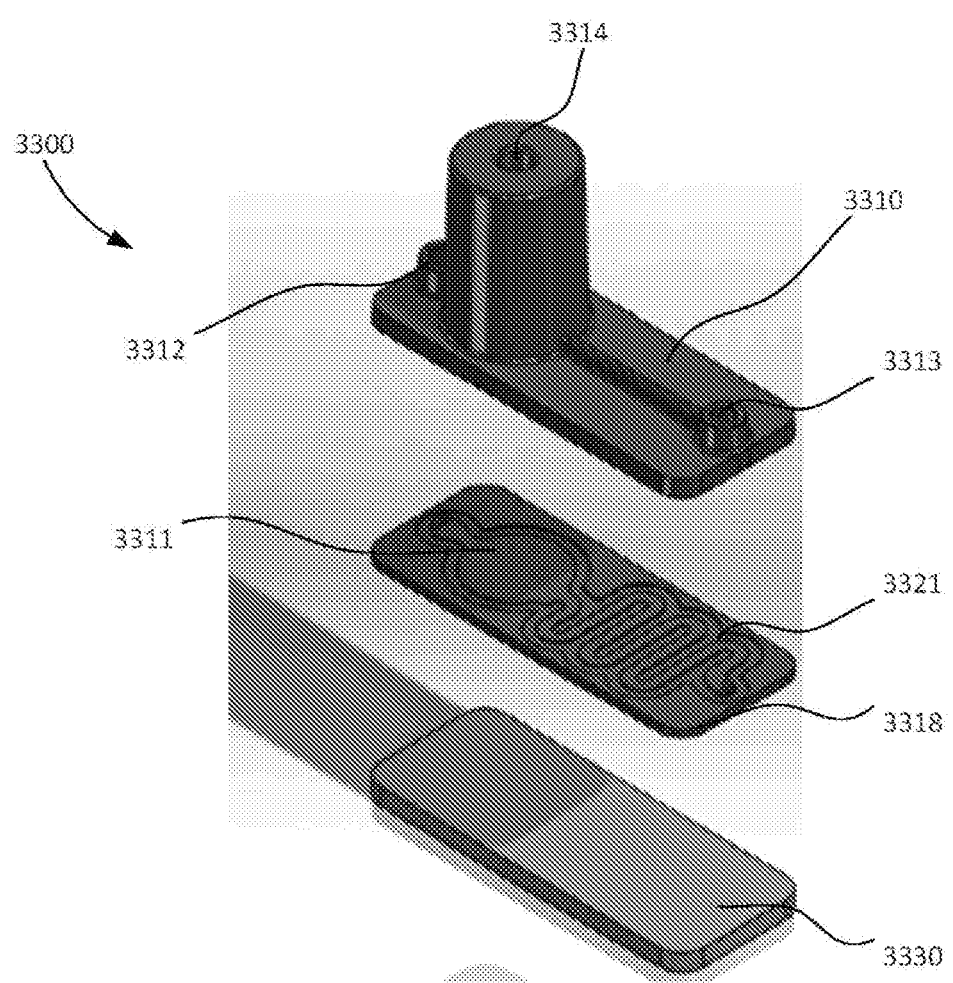
FIG. 14 is an exploded view of the lysing module shown in FIG. 13.
Figure 15:
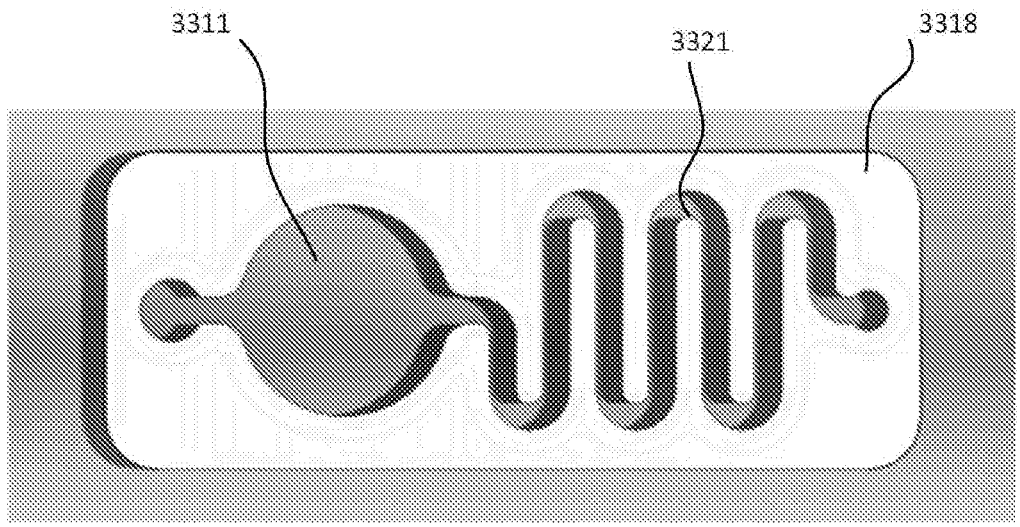
FIG. 15 is a top view of a portion of the lysing module shown in FIG. 13.
Figure 16:
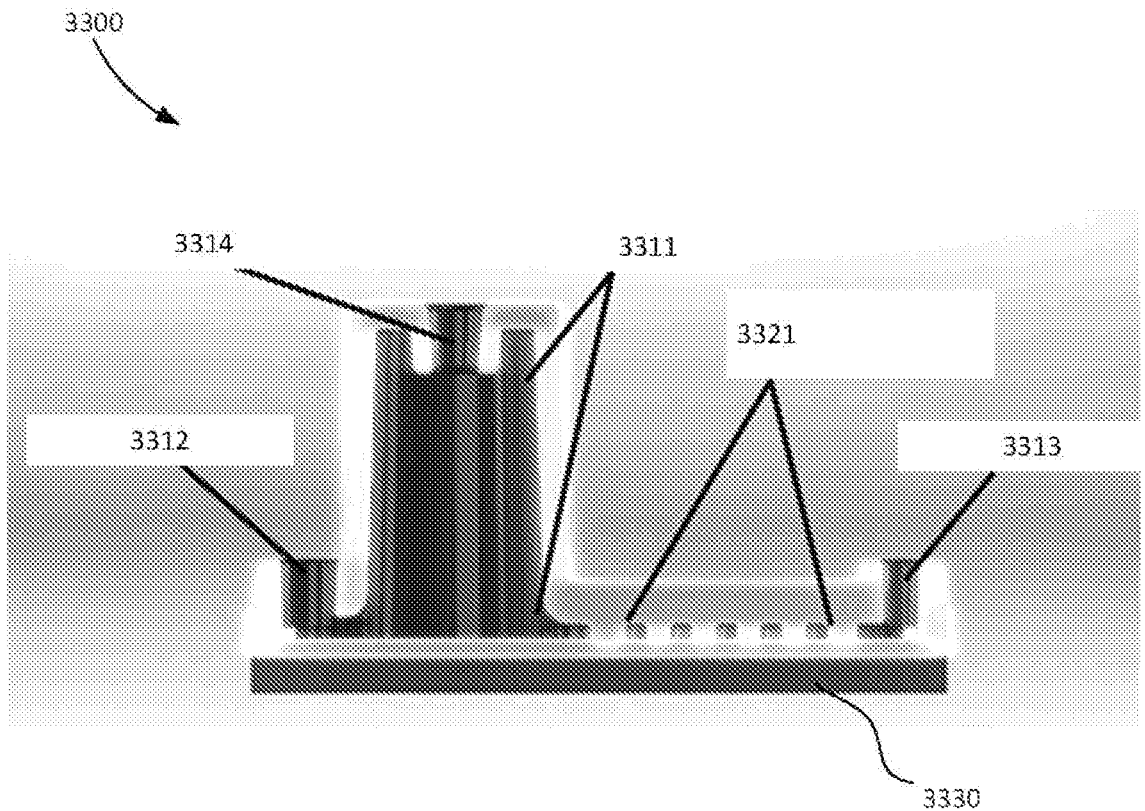
FIG. 16 is a cross-sectional view of the lysing module shown in FIG. 13.
Figure 17:
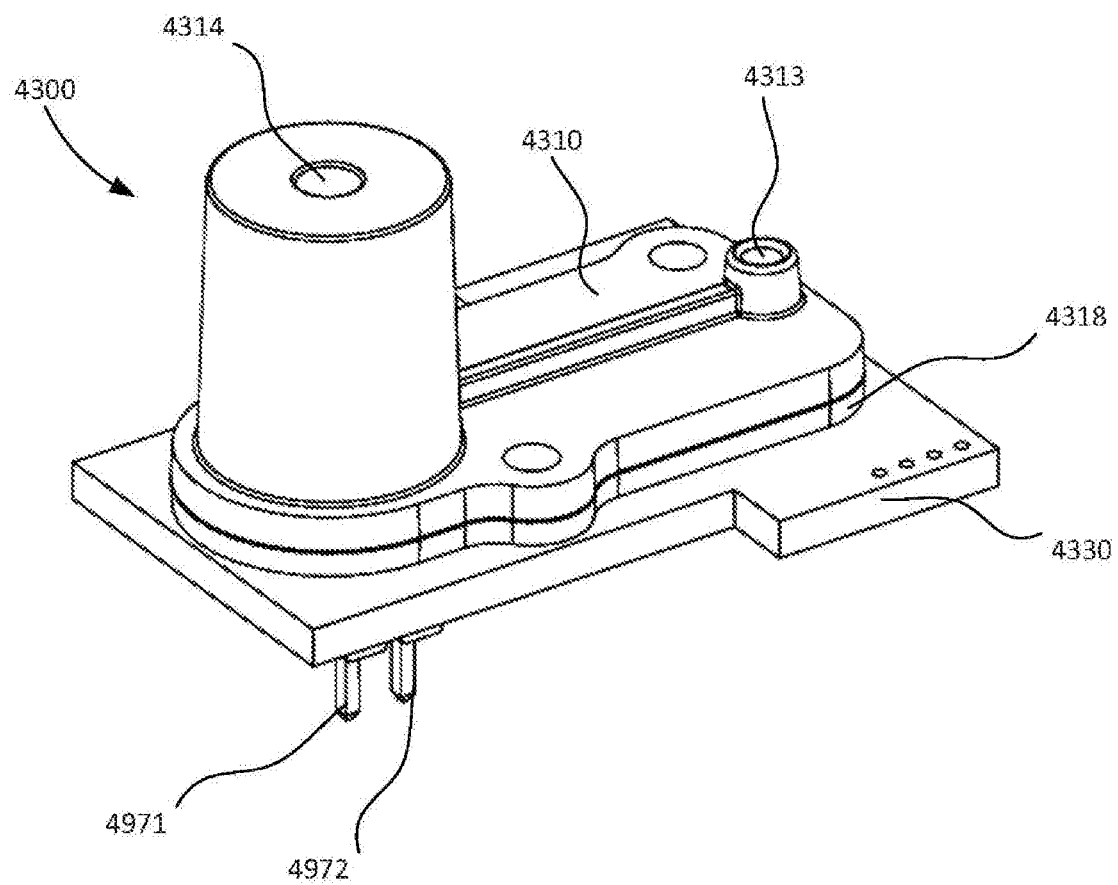
FIGS. 17 and 18 is are perspective views of a lysing module according to an embodiment, which can perform any of the methods described herein.
Figure 18:
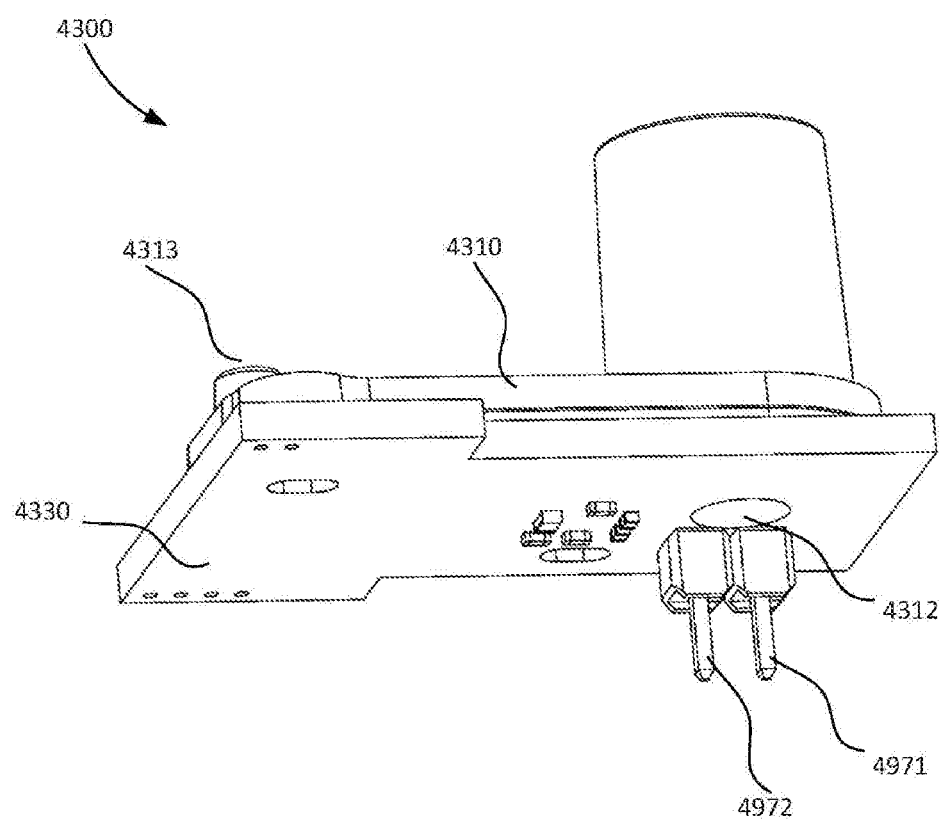
Figure 19:
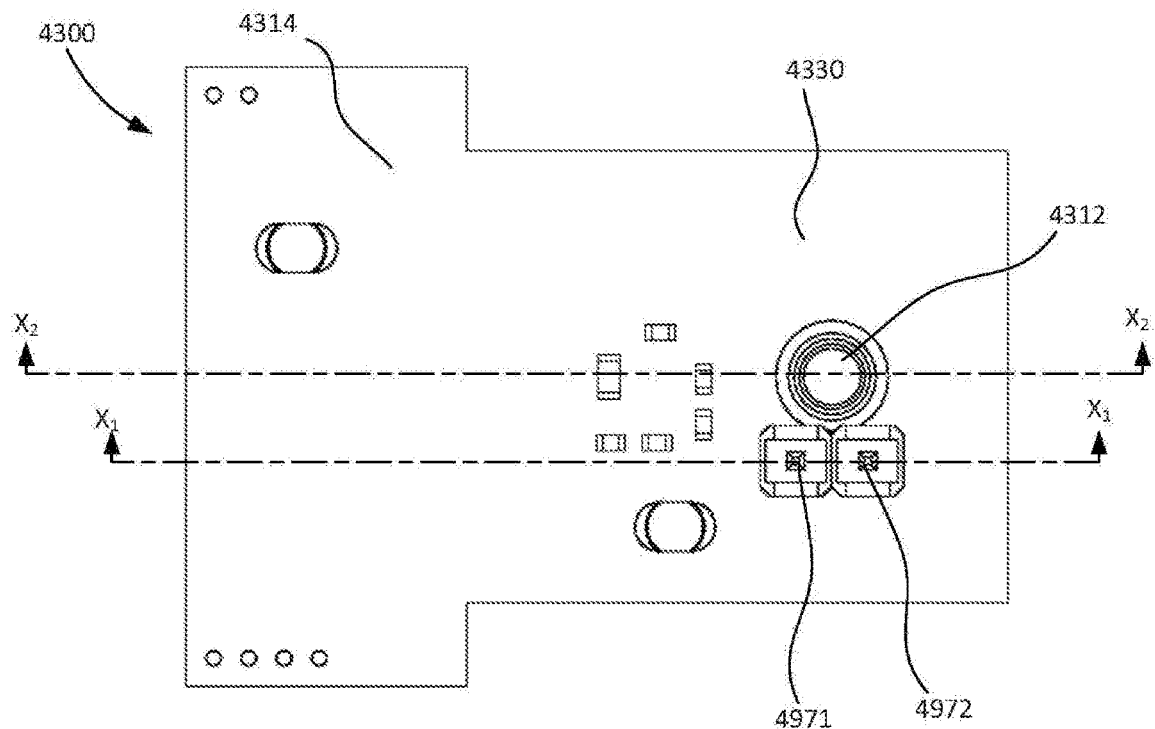
FIG. 19 is a bottom view of the lysing module shown in FIGS. 17 and 18.
Figure 20:
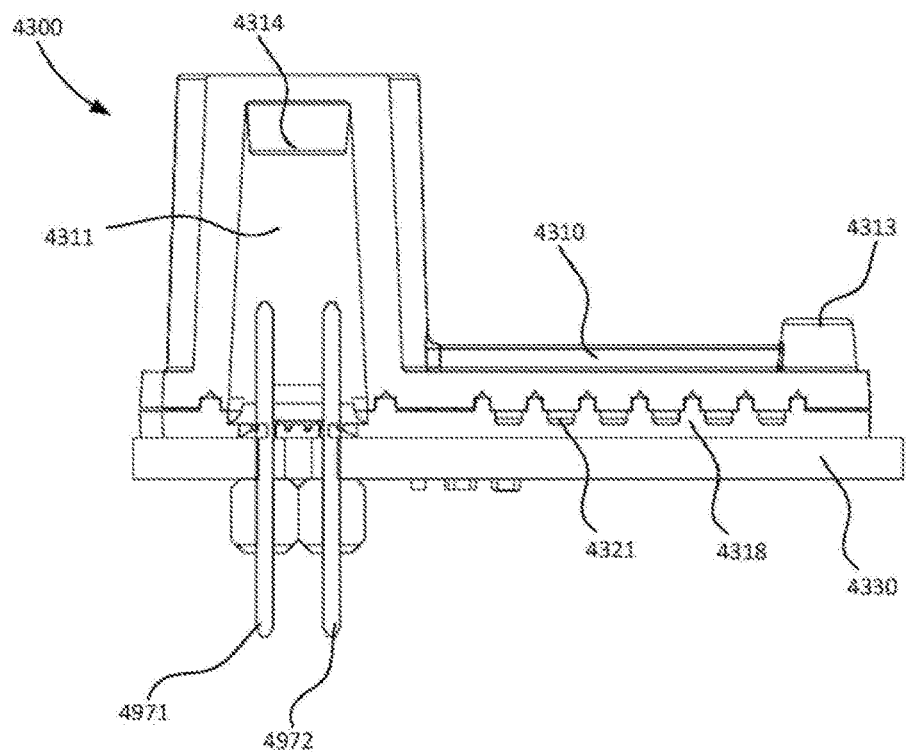
FIG. 20 is a cross-sectional view of the lysing module shown in FIGS. 17 and 18 taken along line $X_1$-$X_1$ in FIG. 19.

For example, FIG. 12 depicts an example of a sample preparation device (or module) 2200 that may be used to perform the methods provided herein. The sample preparation module 2200 can be included in any of the molecular diagnostic test devices described herein, including the device 1000 described above. It should be understood that the invention is not limited to a particular arrangement or configuration of the sample preparation device, and any suitable arrangement or configuration may be used. In some cases, the sample preparation device 2200 comprises an input port 2170. The input port is configured to receive a sample (e.g., biological sample). For example, the input port 2170 may be configured to receive about 50 µL to about 20 mL of a liquid sample. The input port 2170 may comprise a reservoir or chamber for holding or storing the sample. The input port 2170 may comprise a cap or lid (similar to the lid 1152 described above) that can be placed over the input port to contain the sample in the reservoir or chamber. The input port 2170 may be operably coupled to a filter assembly 2230. In use, the sample may be relayed (e.g., pushed or flowed) to the filter assembly 2230 in any manner as described herein. The filter assembly 2230 may contain one or more filter membranes for capturing biological cells or entities on the filter. In some instances, the filter assembly 2230 (or any of the filter assemblies described herein) contains at least two filter membranes, one with a larger pore size and one with a smaller pore size. The two filter membranes may be arranged such that the sample first passes through the membrane with the larger pore size and then the membrane with the smaller pore size. The filter membrane may be of any suitable material as described herein, non-limiting examples including nylon, cellulose, polyethersulfone (PES), polyvinylidene difluoride (PVDF), polycarbonate, borosilicate glass fiber and the like. In some examples, the filter membrane is nylon. In some cases, the filter membrane has an average pore size of about 0.2 µm to about 20 µm. For example, the filter membrane may have an average pore size of about 0.2 µm, about 0.5 µm, about 1 µm, about 2 µm, about 3 µm, about 4 µm, about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, about 20 µm, or greater than 20 µm. In some examples, the surface of the filter membrane may be chemically treated or coated in such a way as to improve the binding of a biological cell or entity to the membrane. The biological cells or entities may be captured on the membrane while the majority of the liquid ("flow-through") is flowed through the filter membrane. In some cases, the flow-through is substantially devoid of biological cells or entities. In some cases, the flow-through is disposed of by relaying the flow-through to one or more waste chambers operably coupled to the filter assembly. In other cases, the flow-through is relayed to a collection chamber for further downstream processing.

In some aspects, the sample preparation device 2200 further comprises one or more chambers 2210 or reservoirs for housing a wash solution. The one or more chambers or reservoirs (also referred to as wash modules) housing the wash solution may be operably coupled to the filter assembly such that actuation of the wash chamber or reservoir 2210 relays the wash solution to the filter assembly 2230. In some cases, the wash solution is provided as a lyophilized pellet or bead that sits within the chamber or reservoir. The lyophilized pellet or bead can be reconstituted in one or more solutions. The wash solution may be flowed through the filter assembly 2230 and the majority of the liquid can be collected in the one or more waste chambers 2205. Non-limiting examples of wash solutions suitable for use with the sample preparation device have been described above.

In certain aspects, the sample preparation device further comprises one or more chambers or reservoirs for housing a lysis solution. The chamber or reservoir housing the lysis solution may be operably coupled to the filter assembly such that actuation of the chamber or reservoir relays the lysis solution to the filter assembly. In some cases, the lysis solution may be flowed through the filter assembly. The lysis solution may cause the lysis or disruption of the biological cells or entities on the filter membrane. In some cases, the reagents of the lysis solution are provided as a lyophilized pellet or bead that sits within the chamber or reservoir (e.g., within a lysing module, similar to the lysing modules 1300, 3300 and 4300 described herein). The lyophilized pellet or bead can be reconstituted in one or more solutions. In some cases, the lysis enzyme is stored separately as a lyophilized bead or pellet within the device. In some cases, the lyophilized lysis enzyme may be reconstituted in the lysis buffer prior to addition to the cells. In other cases, the cells are eluted from the filter membrane and relayed into the elution chamber 2260 which contains the lyophilized lysis enzyme, thereby reconstituting the enzyme. In cases where a lysis enzyme is used, the enzyme is stable in the device at ambient temperatures for long periods of time. For example, the enzyme may be stable in the device at ambient temperature for at least one day, at least two days, at least three days, at least four days, at least five days, at least six days, at least one week, at least two weeks, at least three weeks, at least four weeks, at least a month, at least two months, at least three months, at least four months, at least five months, at least six months, at least seven months, at least eight months, at least nine months, at least ten months, at least eleven months, at least one year, at least two years, at least three years, at least four years, at least five years, at least six years, at least seven years, at least eight years, at least nine years, at least ten years or longer. The lysis solution containing the lysed cells ("eluent") may be collected in an elution chamber. In some cases, the lysis solution may be back-flowed through the filter assembly. In this instance, the biological cells or entities on the filter membrane may be pushed or washed from the membrane and collected in an elution chamber with the lysis solution. The cells or entities (or lysed or otherwise disrupted cells or entities) diluted in the lysis solution may be referred to as the "eluent."

In some aspects, the sample preparation device 2200 may further comprise one or more heating modules (not shown). The one or more heating modules may be operably coupled to the elution chamber 2260. The one or more heating modules may heat the elution chamber to a temperature sufficient for lysis of the biological cells or entities to occur. In some cases, the lysis solution comprises one or more enzymes (e.g., Proteinase K). In some cases, the one or more heating modules heats the elution chamber to a temperature sufficient for optimal performance of the lysis enzyme. In some examples, the heating module heats the elution chamber (and the fluid contained therein) to a temperature of about 4° C., about 10° C., about 15° C., about 20° C., about 25° C., about 30° C., about 40° C., about 45° C., about 50° C., about 55° C., about 60° C., about 65° C., about 70° C., about 75° C. or greater than 75° C.

In some aspects, the sample preparation device 2200 and/or any of the molecular diagnostic devices described herein further comprises an inactivation chamber (also referred to as an inactivation module or a lysing module). The inactivation chamber may be operably coupled to the elution chamber. The eluent may be relayed from the elution chamber to the inactivation chamber. In some instances, the elution chamber and the inactivation chamber are the same chamber and are coupled to a heating element that can heat the chamber to an optimal lysis temperature, and can further heat the chamber to an optimal inactivation temperature (e.g., from about 56° C. to about 95° C.).

For example, a non-limiting example of an inactivation chamber 3300 is depicted in FIGS. 13-16. In this example, the inactivation chamber comprises a chamber body 3310, a bottom lid 3318, and a heater 3330. As depicted in FIG. 12, the chamber body 3310 may defines an input port 3312, a holding tank (or first volume) 3311, a permanent vent 3314, an inactivation segment (or second volume) 3321, and an output port 3313. The input port 3312 may be configured to receive the eluent from the elution chamber and/or directly from a filter assembly (e.g., the filter assembly 1230). In other embodiments, as described herein, the input port 3312 can be fluidically coupled to a sample input module without the biological input being conveyed through a filter. The eluent may flow into the inactivation chamber (or lysing module 3300) and be collected in the holding tank 3311. The holding tank may have a capacity of about 1 µL to about 100 mL, about 100 µL to about 10 mL, about 300 µL to 1 mL, or about 300 µL to about 650 µL. The holding tank may be used to lyse the sample. For example, in some embodiments, the eluent containing the target organisms can be heated by the heater 3330 to maintain the eluent at or above a target lysing temperature. Similarly stated, in some embodiments, the heater 3330 can be coupled to the chamber body 3310 and/or the bottom lid 3318 such that the heater 3330 can convey thermal energy into the lysing module 3300 to produce a lysing temperature zone within the holding tank (or first volume) 3311. The lysing temperature zone can maintain the eluent at any of the temperatures and for any of the time periods described herein.

The vent 3314 may be a hole which allows air to flow into or out of the lysing module 3300 (including the first volume 3311 and the second volume 3321) as sample is brought in or out. The vent 3314 can also relieve pressure within either of the first volume 3311 or the second volume 3321 when the eluent is heated. Although described as being a permanent vent (i.e., a vent having a fixed opening), in some embodiments, the lysing module 3300 (or any of the lysing modules described herein) can have an active vent. For example, in some embodiments, the lysing module 3300 (or any of the lysing modules described herein) can include a valve that controls the venting of pressure and/or air from within the lysing module 3300.

The eluent may flow from the holding tank 3311 through the inactivation segment of the lysing module 3300. More specifically, the holding tank 3311 is in fluid communication with the inactivation segment 3321 such that when a pressure gradient is applied across the input port 3312 and the output port 3313, the eluent can flow from the holding tank 3311 (first volume) through the inactivation segment 3321 (second volume). The pressure gradient can be applied by any suitable mechanism, such as for example, a pump (e.g., the fluidic drive module 1400). The inactivation segment 3321 may be a small, shallow channel that allows efficient and rapid heating of the eluent as it leaves the holding tank. In a non-limiting example, the inactivation segment 3321 is configured in a serpentine pattern. The serpentine pattern may allow for rapid inactivation of the lysis enzymes in the eluent. The eluent, after being flowed through the inactivation segment, may be flowed into the output port 3313 to be collected. The volume of liquid passed through the heated channel could be from about 1 µL to about 100 mL, about 10 µL to about 10 mL, about 100 µL to about 5 mL, or about 250 µL to about 750 µL.

As described above, the inactivation module 3300 may be in contact with a heating element 3330, which can be, for example, a printed circuit board (PCB) heater. The heating element 3330 may function to heat the eluent as it flows through the inactivation segment at a high temperature sufficient to inactivate the one or more lysis enzymes contained within the eluent. For example, the heating element may heat the eluent to about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C. or greater than 100° C. By heating the liquid eluent to a high temperature, the lysis enzymes as well as any other enzymes present can be deactivated. In some embodiments, the sample can be heated to about 95 C for about 3 minutes. In some embodiments, the serpentine path 3321 may be preceded by a check valve (not shown) to maintain a back pressure such that fluid does not enter the serpentine path 3321 before the desired temperature has been achieved. The serpentine area may be preheated to the desired temperature (50° C. to 99° C. or more) before fluid is drawn through the serpentine channel. If fluid were to flow into the serpentine channel prematurely without controlled flow, large bubbles may form in the channel as the heater warms up which could result in portions of the fluid to pass through the channel without receiving the proper temperature treatment.

In some embodiments there may be a one-way check valve that allows flow between the inactivation chamber and the mixing chamber (and prevents reverse flow). However, before flow can occur a certain amount of "cracking pressure" must be achieved. If the holding tank of the inactivation chamber is well vented from a vent port, the liquid that is placed into the holding tank will not flow into the serpentine channel due to the cracking pressure of the check valve at the exit of the serpentine channel. The cracking pressure may be from 0.05 to 50 psi. In some examples, the check valves used may have a cracking pressure of approximately 0.5 psi.

As described, the solution within the second volume 3321 is rapidly heated to temperatures of up to about 100 degrees Celsius. The lysing module 3300 and/or the formulation of the input solution (e.g., the eluent), however, can collectively reduce the likelihood that the liquid portion of the input solution will boil during the lysing/inactivation operations. Such boiling can produce undesirable bubbles and/or air pockets and can reduce the repeatability of the lysing and/or inactivation operations. Moreover, to facilitate use of the device at a variety of different altitudes, the lysing module 3300 and/or the formulation of the input solution can collectively reduce the likelihood that the liquid portion of the input solution will boil at a temperature of 99 degrees Celsius or higher, 98 degrees Celsius or higher, 96 degrees Celsius or higher, 94 degrees Celsius or higher, 92 degrees Celsius or higher, 90 degrees Celsius or higher, or 88 degrees Celsius or higher. For example, in some embodiments, the input solution can include salts and/or sugars to raise the boiling temperature of the input solution. In other embodiments, the lysing module 3300 can include one or more vent openings into either the first volume 3311 or the second volume 3321 or both (to limit pressure build-up during heating).

After the lysing and inactivation operations, the output from the lysing module 3300 can be conveyed into an (e.g., the amplification module 1600 or any other amplification modules described herein). Similarly stated, the output from the lysing module 3300, which contains the extracted nucleic acid molecules, can be conveyed to an amplification module. The amplification module can then perform a thermal reaction (e.g., an amplification reaction) on the prepared solution containing target nucleic acid mixed with required reagents. In some embodiments, the amplification module is configured to conduct rapid amplification of an input target. In some embodiments, the amplification module is configured to generate an output copy number that reaches or exceeds the threshold of the sensitivity of an associated detection module (e.g., the detection module 1800).

FIGS. 17-22 show various views of a lysing module 4300 (also referred to as an inactivation module), according to an embodiment. The lysing module 4300 includes a chamber body 4310, a bottom lid 4318, a heater 4330, and an electrode assembly. The chamber body 4310 and the bottom lid 4318 can be referred to as a flow member. Although the flow member is shown as being constructed from two pieces (the body 4310 and the bottom lid 4318) that are coupled together, in other embodiments, the flow member can be monolithically constructed. The chamber body 4310 and the bottom lid 4318 define an input port 4312, a first (or holding) volume 4311, a vent 4314, a second (or inactivation) volume 4321, and an output port 4313. The input port 4312 can receive the eluent from the elution chamber and/or directly from a filter assembly (e.g., the filter assembly 1230). In other embodiments, as described herein, the input port 4312 can be fluidically coupled to a sample input module without the biological input being conveyed through a filter. In use, the eluent can flow into the lysing module 4300 and be collected in the holding volume 4311. The sample can be lysed within the holding volume 4311. For example, in some embodiments, the eluent containing the target organisms can be heated by the heater 4330 to maintain the eluent at or above a target lysing temperature. Similarly stated, in some embodiments, the heater 4330 can be coupled to the chamber body 4310 and/or the bottom lid 4318 such that the heater 4330 can convey thermal energy into the lysing module 4300 to produce a lysing temperature zone within the holding volume 4311. The lysing temperature zone can maintain the eluent at any of the temperatures and for any of the time periods described herein.

The vent opening 4314 is in fluid communication with the first volume 4311, and thus allows air to flow into or out of the lysing module 4300 (including the first volume 4311 and the second volume 4321) as sample is conveyed into and/or out of the lysing module 4300. The vent 4314 can also relieve pressure within either of the first volume 4311 or the second volume 4321 when the eluent is heated. Although shown as being a permanent vent (i.e., a vent having a fixed opening), in some embodiments, the lysing module 4300 (or any of the lysing modules described herein) can have an active vent. For example, in some embodiments, the lysing module 4300 (or any of the lysing modules described herein) can include a valve that controls the venting of pressure and/or air from within the lysing module 4300.

The first volume 4311 is in fluid communication with the second volume 4322. In this manner, the eluent can flow from the first (or holding) volume 4311 through the second (or inactivation) volume 4321 of the lysing module 4300. More specifically, when a pressure gradient is applied across the input port 4312 and the output port 4313, the eluent can flow from the holding volume 4311 (first volume) through the second volume 4322. The pressure gradient can be applied by any suitable mechanism, such as for example, a pump (e.g., the fluidic drive module 1400). As shown, the second volume 4321 is a serpentine channel that provides a high surface area to volume ratio. This arrangement allows for rapid inactivation of the lysis enzymes in the eluent. The eluent, after being flowed through the inactivation segment, may be flowed into the output port 4313 to be collected and/or conveyed to an amplification module (not shown).

As described above, the flow member is in contact with a heating element 4330, which can be, for example, a printed circuit board (PCB) heater. The heating element 4330 may function to heat the eluent as it flows through the second volume 4311 at a high temperature sufficient to inactivate the one or more lysis enzymes contained within the eluent. For example, the heating element may heat the eluent to about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C. or greater than 100° C. By heating the liquid eluent to a high temperature, the lysis enzymes as well as any other enzymes present can be deactivated. In some embodiments, the sample can be heated to about 95 C for about 4 minutes.

In some embodiments the heater on the PCB 4330 is specifically designed to heat the serpentine portion of the lysing module 4300 (i.e., the second volume 4321) while not heating the holding volume 4311. Because the lid 4318 of the lysing module 4300 is thick, the heater surface may be heated well above the desired temperature of the fluid. Since the electrodes 1971, 1972 (described in more detail below) are thermally conductive and come into direct contact with the fluid, the fluid surrounding the electrodes 1971, 1972 will experience the same temperature as the heater surface, which may cause evaporation. To minimize the heating of the holding volume 4311, a slot (not shown) may be cut in the PCB 4330 to isolate the heater from the portion of the PCB adjacent and/or in contact with the holding volume 4311. For example, in some embodiments, the heater 4330 can include a series of slots and/or openings as described in U.S. patent application Ser. No. 15/494,145, entitled "Printed Circuit Board Heater for an Amplification Module," which is incorporated herein by reference in its entirety. Moreover, in some embodiments, the heating element of the heater 4330 is located on an internal layer so the top copper pour (not shown) can be used as a heat spreader to minimize temperature variation along the serpentine path. The six wires soldered to the PCB 4330 may remove heat from the surrounding area, creating temperature gradients across the heater surface. To minimize this effect, wires may be soldered on both sides of the heater surface so the temperature roll off is symmetrical.

In some embodiments, the lysing module 4300 can determine whether there is liquid in the first volume 4311 and/or the second volume 4321. Specifically, the lysing module 4300 includes electrical probes to determine electrical resistance of the fluid within the first volume. In some embodiments, the molecular diagnostic device (e.g., the device 1000) can include an electronic controller configured to determine when the user has actuated the elution module (e.g., by pressing an elution actuator, similar to the button 1070 described above) by detecting the presence of liquid in the first volume 4311. In this manner, the introduction of liquid into the first volume 4311 can trigger the start of the device.

Specifically, the control system and/or the lysing module 4300 includes two electrodes 4971, 4972 inside the first volume 4311. The electrodes 4971, 4972 are connected to circuitry (e.g., a controller, not shown) that detects a resistance change between the two electrodes 4971, 4972. Fluid may be reliably detected between the electrodes 4971, 4972 due to the high gain of the circuit, which may easily differentiate between an open circuit condition (no fluid) and a non-negligible resistance across the electrodes 4971, 4972 (fluid detected). Use of a sample matrix with high salt concentration increases the conductivity of the fluid, which may make the fluid easily detectable even with variation across samples.

The electrodes 4971, 4972 and the circuitry (not shown) are designed to detect fluid without impacting the biological processes that take place in the device. For example, the electrodes 4971, 4972 are specifically chosen so as not inhibit PCR reactions. In some embodiments, the electrodes 4971, 4972 are gold plated.

Both DNA and cells have a net charge so they may migrate in the presence of an electric field. Because the resistance change between the electrodes 4971, 4972 is determined by measuring a change in electric potential, precautions may be taken to minimize the impact of this electromotive force. For example, once fluid is detected voltage may be removed from the electrodes 4971, 4972 and they may be electrically shorted together. This ensures there is no potential difference between the electrodes 4971, 4972 and the charged particles (DNA, cells, salts, etc.) will not bind to the electrodes, which would prevent them from entering the amplification module (not shown).

As described, the solution within the second volume 4321 is rapidly heated to temperatures of up to about 100 degrees Celsius. The lysing module 4300 and/or the formulation of the input solution (e.g., the eluent), however, can collectively reduce the likelihood that the liquid portion of the input solution will boil during the lysing/inactivation operations. Such boiling can produce undesirable bubbles and/or air pockets and can reduce the repeatability of the lysing and/or inactivation operations. Moreover, to facilitate use of the device at a variety of different altitudes, the lysing module 4300 and/or the formulation of the input solution can collectively reduce the likelihood that the liquid portion of the input solution will boil at a temperature of 99 degrees Celsius or higher, 98 degrees Celsius or higher, 96 degrees Celsius or higher, 94 degrees Celsius or higher, 92 degrees Celsius or higher, 90 degrees Celsius or higher, or 88 degrees Celsius or higher. For example, in some embodiments, the input solution can include salts and/or sugars to raise the boiling temperature of the input solution. In other embodiments, the lysing module 4300 can include one or more vent openings into either the first volume 4311 or the second volume 4321 or both (to limit pressure build-up during heating).

After the lysing and inactivation operations, the output from the lysing module 4300 can be conveyed into an (e.g., the amplification module 1600 or any other amplification modules described herein). Similarly stated, the output from the lysing module 4300, which contains the extracted nucleic acid molecules, can be conveyed to an amplification module. The amplification module can then perform a thermal reaction (e.g., an amplification reaction) on the prepared solution containing target nucleic acid mixed with required reagents. In some embodiments, the amplification module is configured to conduct rapid amplification of an input target. In some embodiments, the amplification module is configured to generate an output copy number that reaches or exceeds the threshold of the sensitivity of an associated detection module (e.g., the detection module 1800).

Figure 23:
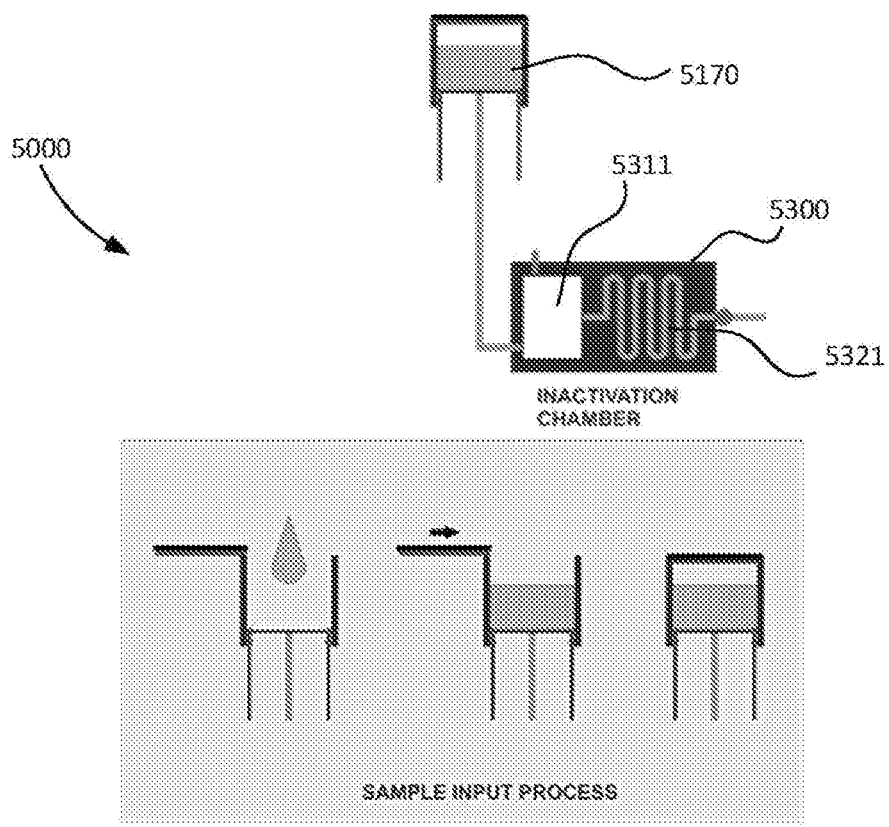
FIG. 23 is a schematic illustration of a portion of a molecular diagnostic test device, according to an embodiment, which can perform the methods described herein.

Although the device shown in FIG. 10 is described as including a filter assembly, in some embodiments, a sample preparation device need not include a filter or filter assembly. For example, in some embodiments the sample input may be directly linked to an inactivation chamber, as shown schematically in FIG. 23. Advantages of a device without a filter assembly include lower pressures in the device, no risk of breaking a filter, fewer parts, fewer reagents required, higher recovery of target organisms from the clinical sample matrix and higher recovery of DNA from target organisms. FIG. 23 shows a portion of a molecular test device 5000 that includes a sample input module 5170 and an inactivation (or lysing) module 5300. The device 5000 can be similar to the device 1000 described above, and can include an amplification module, a detection module or the like. In this case, the device 5000 differs from the device 1000 in that the sample is flowed from the input module 5170 into the holding tank of the inactivation module 5300. The sample may be lysed either in the holding tank 5311 or in the inactivation segment 5321. In this case the sample may be lysed by heating without need for a specialized lysis buffer or lysis enzymes. Any proteases or nucleases released from the cells of the sample will be inactivated by heating. For example, a sample may be flowed into the holding tank and held until the inactivation segment 5321 reaches a set temperature (for example greater than 90 C) and then flowed through the inactivation segment. In the inactivation segment the sample is rapidly heated to 95 C causing the cells in the sample to lyse and proteins from within the cells to be inactivated.

Figure 24:
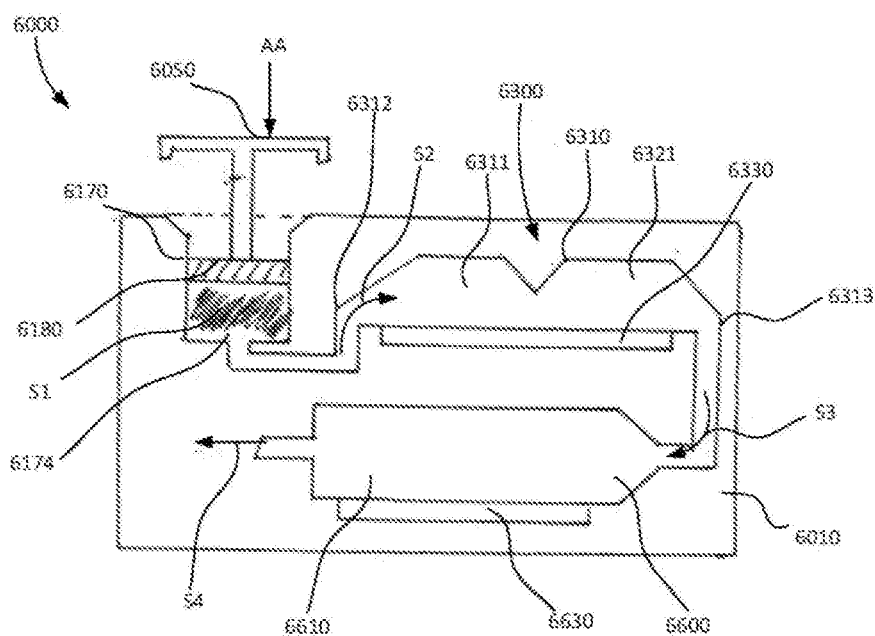
FIG. 24 is a schematic illustration of a molecular diagnostic test device, according to an embodiment, which can perform the methods described herein.

As another example of an embodiment in which the sample is not conveyed through a filter, FIG. 24 is a schematic illustration of a molecular diagnostic test device 6000 (also referred to as a "test device" or "device"), according to an embodiment. The test device 6000 includes a housing 6010, a sample input module 6170, a lysing module 6300, and an amplification module 6600. The housing 6010 can be any structure within which the sample input module 6170, the lysing module 6300, and the amplification module 6600 are contained. In some embodiments, the test device 6000 can have a size, shape and/or weight such that the device can be carried, held, used and/or manipulated in a user's hands (i.e., it can be a "handheld" device). In other embodiments, the test device 6000 can be a self-contained, single-use device of the types shown and described herein (e.g., the device 1000) or in International Patent Publication No. WO2016/109691, entitled "Devices and Methods for Molecular Diagnostic Testing," which is incorporated herein by reference in its entirety.

The sample input module 6170 is disposed within the housing 6010, and is configured receive a biological sample S1 containing a biological entity. The biological sample S1 can be any of the sample types described herein, and the biological entity can be any of the entities described herein. The sample input module 6170 defines a sample volume 6174, and includes a piston 6180 that is movably disposed within the sample volume 6174. In use the biological sample S1 can be conveyed into the sample volume 6174 by any suitable mechanism, such as, for example, via a pipette, a dropper, or the like. In some embodiments, the biological sample S1 can be conveyed via an opening into the sample volume 6174 that can be blocked to prevent backflow of the sample back out of the sample input volume 6174. For example, in some embodiments, the sample input module 6170 can include any suitable flow control devices, such as check valves, duck-bill valves, or the like, to control the flow of the biological sample S1 within the device 6000.

The sample input module 6170 (and any of the sample input modules described herein) can be actuated by any suitable mechanism to convey the biological sample S1 towards the lysing module 6300 to enable the nucleic acid extraction methods described herein. For example, in the embodiment shown, the sample input module 6170 is actuated by the sample actuator (or button) 6050. The sample actuator 6050 is movably coupled to the housing 6010, and is aligned with and can move the piston 6180 when the sample input module 6170 is actuated. The sample actuator 6050 is a non-electronic actuator that is manually depressed by a user to actuate the sample input module 6170. In other embodiments, however, the sample actuator 6050 can be an electronic actuator. In some embodiments, the sample actuator 6050 can include a lock tab (not shown) that is fixedly received within the notch or opening of the housing 6010 to fix the sample actuator 6050 in its second or "actuated" position, as described above. In this manner, the device 6000 cannot be reused after the initial actuation. When the piston 6180 is moved downward within the sample volume 6174, as shown by the arrow AA, the sample within the sample volume 6174 is conveyed towards the lysing module 6300. The flow of the biological sample S1 towards the lysing module 6300 is shown by the arrow S2 in FIG. 24.

The lysing module 6300 (also referred to as the inactivation module), which can be a portion of a sample preparation module, is configured to process the biological sample S1 to facilitate detection of an organism therein that is associated with a disease. Specifically, the lysing module 6300 is configured to concentrate and lyse cells in the biological sample S1, thereby allowing subsequent extraction of a nucleic acid to facilitate amplification (e.g., via the amplification module 6600) and/or detection (e.g., via a detection module, not shown). As shown, the processed/lysed sample (e.g., the sample S3) is pushed and/or otherwise transferred from the lysing module 6300 to other modules within the device 6000 (e.g., the amplification module 6600). By eliminating the need for external sample preparation and a cumbersome instrument, the device 6000 is suitable for use within a point-of-care setting (e.g., doctor's office, pharmacy or the like) or at the user's home, and can receive any suitable biological sample S1. The biological sample S1 (and any of the input samples described herein) can be, for example, blood, urine, male urethral specimens, vaginal specimens, cervical swab specimens, and/or nasal swab specimens gathered using a commercially available sample collection kit.

The lysing module includes a flow member 6310 and a heater 6330. The flow member 6310 includes an input port 6312 and an output port 6313, and defines a first volume 6311 and a second volume 6321. As shown, the first volume 6311 can receive an input solution (identified as S2) containing at least the biological sample S1 and a lysis buffer. The lysis buffer can be any of the lysis buffers described herein. Moreover, the lysis buffer can be mixed with the biological sample S1 to form the input solution S2 in any suitable manner or at any suitable location within the device 6000. For example, in some embodiments, the lysis buffer can be stored within the sample input module 6170, and can be mixed with the biological sample S1 when the biological sample S1 is conveyed into the volume 6174. In other embodiments, the lysis buffer can be stored in a reagent module (not shown) and can be mixed with the biological sample S1 when the sample input module 6170 is actuated (e.g., via the actuator 6050). In yet other embodiments, the lysis buffer can be stored in the lysing module 6300 (e.g., the first volume 6311).

The heater 6330 is coupled to the flow member 6310 and is configured to produce thermal energy that is conveyed into the first volume 6311, the second volume 6321, or both the first volume 6311 and the second volume 6321 to lyse organisms within the biological sample S1 and/or the input solution S2. In this manner, the lysing module 6300 can release one or more nucleic acid molecules from within the cells and/or organisms within the biological sample S1 and/or the input solution S2. Specifically, the heater 6330 and the flow member 6310 are collectively configured to maintain the input solution S2 at a desired lysing temperature for a predetermined amount of time to facilitate and/or promote lysing of the organisms therein. For example, in some embodiments, the first volume 6311 and/or the second volume 6321 can be maintained at a temperature between about 55 degrees Celsius and about 600 degrees Celsius for a time period of about 25 seconds or more. In other embodiments, the first volume 6311 and/or the second volume 6321 can be maintained at a temperature between about 92 degrees Celsius and about 98 degrees Celsius.

In addition to lysing organisms within the input solution S2 to release nucleic acid molecules, the heater 6330 and the flow member 6310 are configured to heat the first volume 6311, the second volume 6321, or both the first volume 6311 and the second volume 6321 to inactivate enzymes present within the biological sample S1 and/or the input solution S2. Specifically, by heating the input solution S2, the lysing module 6300 can denature certain proteins and/or inactivate certain enzymes present within organisms that are within the input solution S2. Such proteins and/or enzymes can, in certain instances, limit the efficiency or effectiveness of the desired amplification operation. Thus, rapid and efficient inactivation can improve the repeatability and accuracy of the amplification and/or the detection of the molecular diagnostic device 6000. In some embodiments, for example, the heater 6330 and the flow member 6310 can collectively produce an inactivation temperature zone within which the input solution S2 can be heated to within the desired temperature range and/or for the desired time period to produce the desired inactivation. For example, in some embodiments, the input solution S2 within the lysing module 6300 can be maintained at a temperature between about 55 degrees Celsius and about 600 degrees Celsius for a time period of about 25 seconds or more. In other embodiments, the input solution S2 within the lysing module 6300 can be maintained at a temperature between about 92 degrees Celsius and about 98 degrees Celsius.

Although described as occurring in two separate heating operations, the lysing and the inactivation can be performed by a single heating operation. For example, in some embodiments, the input solution S2 can be heated to the desired temperature range to both lyse the organisms and inactivate the enzymes as the input solution S2 flows through the first volume 6311 and/or the second volume 6321. Said another way, in some embodiments, the lysing module 6300 can perform "flow through" inactivation and lysing operations. For example, in some embodiments, either of the first volume 6311 or the second volume 6321 (or both) can define a tortuous flow path through which the input solution S2 flows during the lysing/inactivation operation. In this manner, the surface area-to-volume ratio of the first volume 6311 and/or the second volume 6321 can be high enough such that the heat transfer into the input solution S2 occurs rapidly as it flows through the lysing module. In some embodiments, for example, the first volume 6311 and/or the second volume 6321 can define a serpentine flow path. In some embodiments, a ratio of the surface area of the second volume 6321 to the volume of the second volume 6321 is 20 $cm^{-1}$.

In some embodiments, the flow member 6310 (and any of the flow members described herein) can have a volume about 650 microliters or greater, and the flow can be such that at least 60 microliters of the input solution S2 is prepared for amplification (i.e., has nucleic acids extracted therefrom). In other embodiments, at least 20 microliters of the input solution S2 is prepared for amplification by the methods and devices described herein. In other embodiments, at least 30 microliters of the input solution S2 is prepared for amplification by the methods and devices described herein. In yet other embodiments, at least 50 microliters of the input solution S2 is prepared for amplification by the methods and devices described herein.

As described above, in some embodiments, the input solution S2 is rapidly heated to temperatures of up to about 100 degrees Celsius. The lysing module 6300 and/or the formulation of the input solution S2, however, can collectively reduce the likelihood that the liquid portion of the input solution S2 will boil during the lysing/inactivation operations. Such boiling can produce undesirable bubbles and/or air pockets and can reduce the repeatability of the lysing and/or inactivation operations. Moreover, to facilitate use of the device at a variety of different altitudes, the lysing module 6300 and/or the formulation of the input solution S2 can collectively reduce the likelihood that the liquid portion of the input solution S2 will boil at a temperature of 99 degrees Celsius or higher, 98 degrees Celsius or higher, 96 degrees Celsius or higher, 94 degrees Celsius or higher, 92 degrees Celsius or higher, 90 degrees Celsius or higher, or 88 degrees Celsius or higher. For example, in some embodiments, the input solution S2 can include salts and/or sugars to raise the boiling temperature of the input solution S2. In other embodiments, the lysing module 6300 can include one or more vent openings into either the first volume 6311 or the second volume 6321 or both (to limit pressure build-up during heating). In such embodiments, the vent opening can be such that a limited amount of pressure is allowed within the first volume 6311 or the second volume 6321 to raise the boiling temperature of the input solution S2.

After the lysing and inactivation operations, the output from the lysing module 6300 can be conveyed into the amplification module 6600. Similarly stated, the output from the lysing module 6300, which is identified as the prepared solution S3, and which contains the extracted nucleic acid molecules, can be conveyed to the amplification module 6600. The amplification module 6600 can then perform a thermal reaction (e.g., an amplification reaction) on the prepared solution S3 containing target nucleic acid mixed with required reagents. In some embodiments, the amplification module 6600 is configured to conduct rapid amplification of an input target. In some embodiments, the amplification module 6600 is configured to generate an output copy number that reaches or exceeds the threshold of the sensitivity of an associated detection module.

The amplification module 6600 includes a flow member 6610 and a heater 6630. The flow member 6610 can be any suitable flow member that defines a volume or a series of volumes within which the that prepared solution S3 can flow and/or be maintained to amplify the target nucleic acid molecules within the solution S3. The heater 6630 can be any suitable heater or group of heaters coupled to the flow member 6610 that can heat the prepared solution S3 within the flow member 6610 to perform any of the amplification operations as described herein. For example, in some embodiments, the amplification module 6600 (or any of the amplification modules described herein) can be similar to the amplification modules shown and described in U.S. Patent Application No. 65/494,145, entitled "Printed Circuit Board Heater for an Amplification Module," which is incorporated herein by reference in its entirety.

In some embodiments, the flow member 6610 defines a single volume within which the prepared solution S3 is maintained and heated to amplify the nucleic acid molecules within the prepared solution S3. In other embodiments, the flow member 6610 can define a "switchback" or serpentine flow path through which the prepared solution S3 flows. Similarly stated, the flow member 6610 defines a flow path that is curved such that the flow path 6618 intersects the heater 6630 at multiple locations. In this manner, the amplification module 6600 can perform a "flow through" PCR where the prepared solution S3 flows through multiple different temperature regions.

The flow member 6610 (and any of the flow members described herein) can be constructed from any suitable material and can have any suitable dimensions to facilitate the desired amplification performance for the desired volume of sample. For example, in some embodiments, the amplification module 6600 (and any of the amplification modules described herein) can perform 6000x or greater amplification in a time of less than 65 minutes. For example, in some embodiments, the flow member 6610 (and any of the flow members described herein) is constructed from at least one of a cyclic olefin copolymer or a graphite-based material. Such materials facilitate the desired heat transfer properties into the flow path 6620. Moreover, in some embodiments, the flow member 6610 (and any of the flow members described herein) can have a thickness of less than about 0.5 mm. In some embodiments, the flow member 6610 (and any of the flow members described herein) can have a volume about 150 microliters or greater, and the flow can be such that at least 10 microliters of sample is amplified. In other embodiments, at least 20 microliters of sample are amplified by the methods and devices described herein. In other embodiments, at least 30 microliters of sample are amplified by the methods and devices described herein. In yet other embodiments, at least 50 microliters of sample are amplified by the methods and devices described herein.

The heater 6630 can be any suitable heater or collection of heaters that can perform the functions described herein to amplify the prepared solution S3. In some embodiments, the heater 6630 can establish multiple temperature zones through which the prepared solution S3 flows and/or can define a desired number of amplification cycles to ensure the desired test sensitivity (e.g., at least 30 cycles, at least 34 cycles, at least 36 cycles, at least 38 cycles, or at least 40 cycles). The heater 6630 (and any of the heaters described herein) can be of any suitable design. For example, in some embodiments, the heater 6630 can be a resistance heater, a thermoelectric device (e.g. a Peltier device), or the like. In some embodiments, the heater 6630 can be one or more linear "strip heaters" arranged such that the flow path crosses the heaters at multiple different points. In other embodiments, the heater 6630 can be one or more curved heaters having a geometry that corresponds to that of the flow member 6610 to produce multiple different temperature zones in the flow path.

Although the amplification module 6600 is generally described as performing a thermal cycling operation on the prepared solution S3, in other embodiment, the amplification module 6600 can perform any suitable thermal reaction to amplify nucleic acids within the solution S3. In some embodiments, the amplification module 6600 (and any of the amplification modules described herein) can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process.

Figure 25:
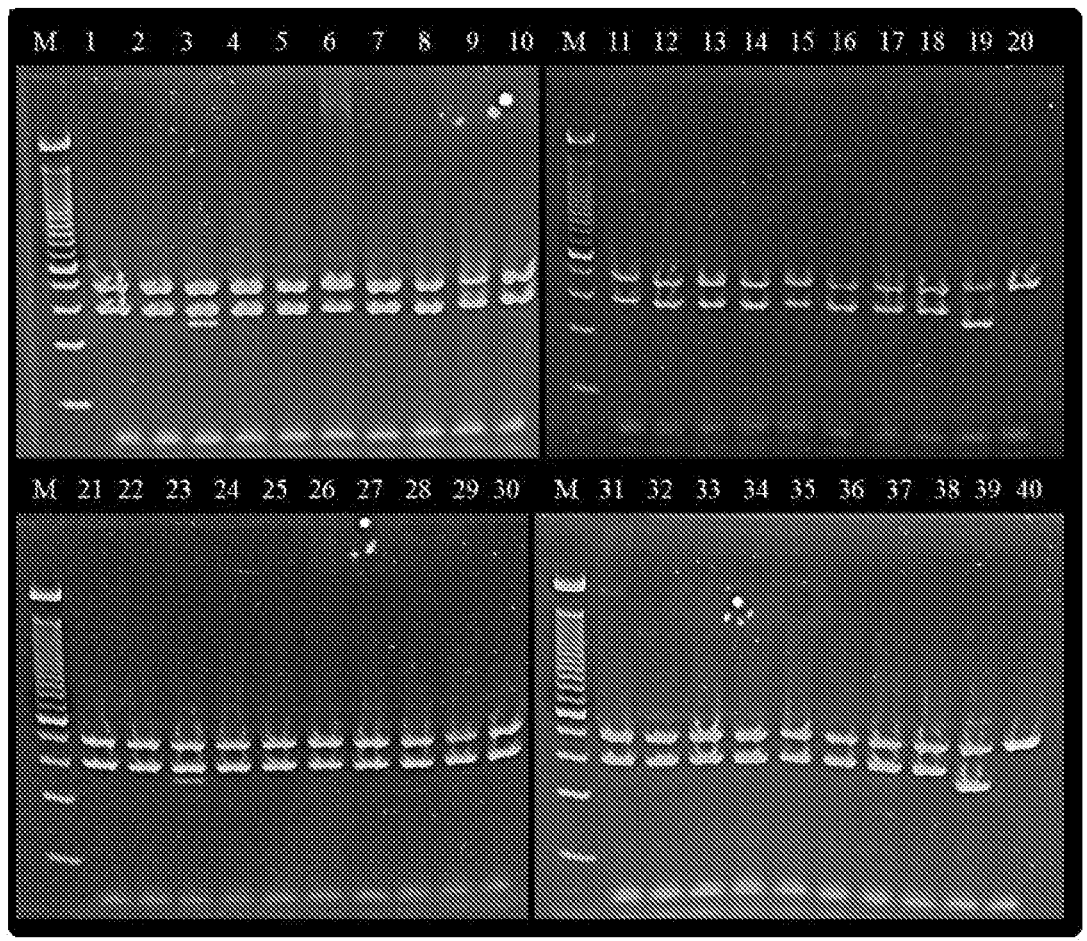
FIG. 25 illustrates the results of a PCR reaction performed upon DNA extracted using the methods of this disclosure.

FIG. 25 is a photograph of a molecular diagnostic test device that can perform any of the methods described herein.

The devices described herein may include and/or be coupled to an amplification module or PCR module of the types shown and described herein, in which a polymerase chain reaction may be performed. The amplification module may be proceeded by a mixing chamber in which the nucleic acid is mixed with components for performing a polymerase chain reaction. Examples of components which may be required for a polymerase chain reaction include nucleotide triphosphates, polymerase enzymes, nucleic acid primers, calcium ions and buffer. In some examples, all components of the reaction mixture may be present in the sample buffer. In other examples the sample buffer may comprise all components except for a polymerase enzyme which may be provided in the mixing chamber. The choice of polymerase enzyme may depend on the purification and lysis protocol used. In some examples, the devices may also comprise a detection module which is capable of detecting nucleic acids amplified in the amplification module.

The devices described herein may be contained with a housing. In some cases, the device is self-contained. In some cases, the device is a handheld device. In some cases, the device is configured for one-time use (e.g., disposable). In some instances, the devices may generate a nucleic acid sample that may be collected prior to performing one or more downstream applications. For example, the sample can be held in a chamber or reservoir within the housing of the device or can be relayed to a chamber or reservoir that sits outside of the housing of the device. In other examples, the device is coupled to one or more additional devices that can perform the one or more downstream applications, for example, a device that can perform a polymerase chain reaction (PCR).

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Comparison of a Traditional DNA Extraction Method Versus an Embodiment of the Methods Described Herein In this example, DNA was extracted from clinical samples using either a standard DNA extraction protocol or a DNA extraction protocol using the methods described herein.

Clinical samples that were positive for *Neisseria gonorrhoeae* and/or *Chlamydia trachomatis* (Samples 101, 105, 108, 117 and 122) were obtained and screened for the presence of these bacteria (See Table 1). These samples were processed utilizing two different methods for DNA extraction. For the first method, 500 μL of each of these samples were taken for DNA extraction utilizing the Qiagen QIAmp® DNA Mini Kit according to the manufacturer's recommendations for isolation of bacterial DNA from bodily fluids ("standard method"). For the second method, 500 μL of each of the samples were taken for DNA extraction utilizing an embodiment of the methods provided herein. Briefly, 500 μL of the sample was preloaded into a clean syringe and 1 mL of air was aspirated into the same syringe. The syringe containing both the sample and air was connected to the filter housing and the entire volume was pushed through (i.e., liquid followed by air). A new syringe was preloaded with 600 μL of wash solution, then the wash solution was pushed through the filter housing. The orientation of the filter was flipped and a female luer lug was attached to the end. Using a new syringe, 350 μL of TT buffer (Tris Acid, Tris Base, a non-ionic surfactant Tween® 80, Antifoam SE-15, a preservative ProClin™300 and molecular grade waters was pushed through the filter in order to elute the sample off the filter into a 1.5 mL tube. The 1.5 mL tube was preloaded with a lyophilized proteinase K pellet. The tube was incubated in a heat block at 56° C. for 1 minute to allow for optimal proteinase K activity. The proteinase K was heat inactivated by placing the tube in a heat block at 95° C. for 10 minutes.

TABLE 1

| Condition | Sample | Purification Method |
|---|---|---|
| 1 | 105 | Qiagen |
| 2 | 117 | Qiagen |
| 3 | 101 | Qiagen |
| 4 | 108 | Qiagen |
| 5 | 122 | Qiagen |
| 6 | 105 | Click SP |
| 7 | 117 | Click SP |
| 8 | 101 | Click SP |
| 9 | 108 | Click SP |
| 10 | 122 | Click SP |
| 11 | Positive Control | N/A |
| 12 | No template control (water) | N/A |

Figure 3:
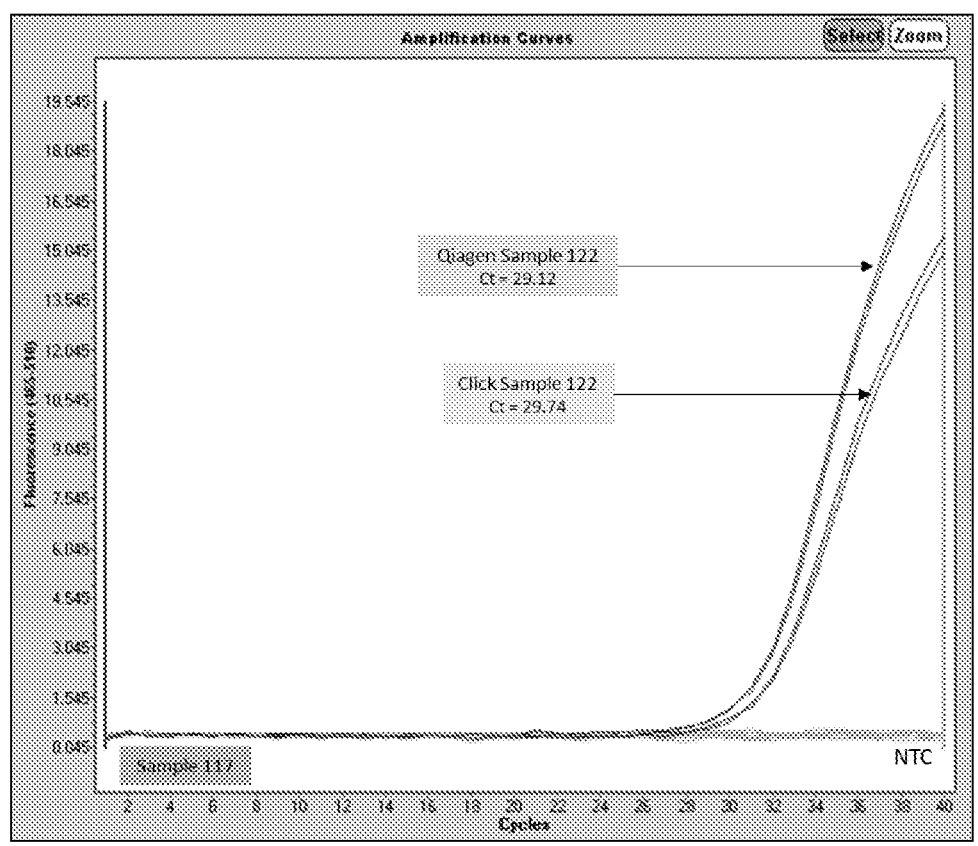
FIG. 3 depicts a comparison of data generated from a real-time PCR reaction performed on DNA extracted from a clinical sample positive for both *N. gonorrhoeae* and *C. trachomatis* (Sample 122) and a clinical sample positive for *N. gonorrhoeae* (Sample 117) utilizing the methods provided herein versus standard DNA extraction methods.
Figure 4:
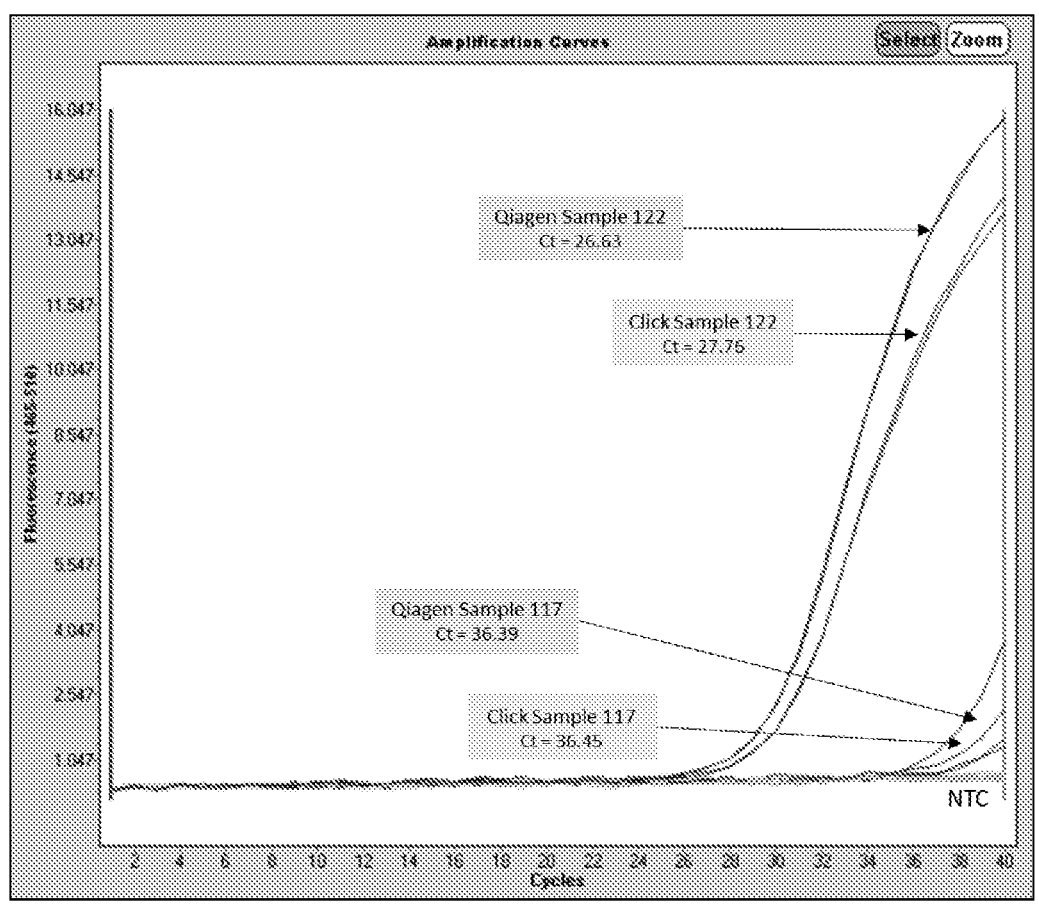
FIG. 4 depicts a comparison of data generated from a real-time PCR reaction performed on DNA extracted from a clinical sample positive for both *N. gonorrhoeae* and *C. trachomatis* (Sample 122) and a clinical sample positive for *N. gonorrhoeae* (Sample 117) utilizing the methods provided herein versus standard DNA extraction methods.

Each sample was mixed with PCR reagents. Primer/probe sets designed to amplify sequences from several different organisms were added to each sample. 1 μL of N. subflava DNA (1,000 copies/rxn) were added to the sample/PCR mix designated for the NS assay. The mixtures were divided into two wells of 20 μL each on a LightCycler® plate. The plate was loaded onto the LightCycler® Real-Time PCR System (Roche) and run under the following PCR conditions:
Stage 1: 95 C for 20 seconds
Stage 2: 40 cycles of: 95 C for 1 second, 60 C for 6 seconds FIGS. 3 and 4 depict a comparison of data generated from real-time PCR reactions performed on DNA extracted from a clinical sample positive for both *N. gonorrhoeae* and *C. trachomatis* (Sample 122) and a clinical sample positive for *N. gonorrhoeae* (Sample 117) utilizing the methods provided herein versus standard DNA extraction methods. Primer Set #1 detected the presence of *N. gonorrhoeae* in Sample 122 prepared using either method as shown in FIG. 3. Primer Set #2 detected the presence of *N. gonorrhoeae* in both Sample 122 and Sample 117, prepared using either method as shown in FIG. 4. Both the standard ("Qiagen sample") and the new method ("Click sample") yielded a Ct value of ~36 with an endpoint signal of less than 5, indicating that the sample had a low titer of *N. gonorrhoeae*. (FIG. 4)

Figure 5:
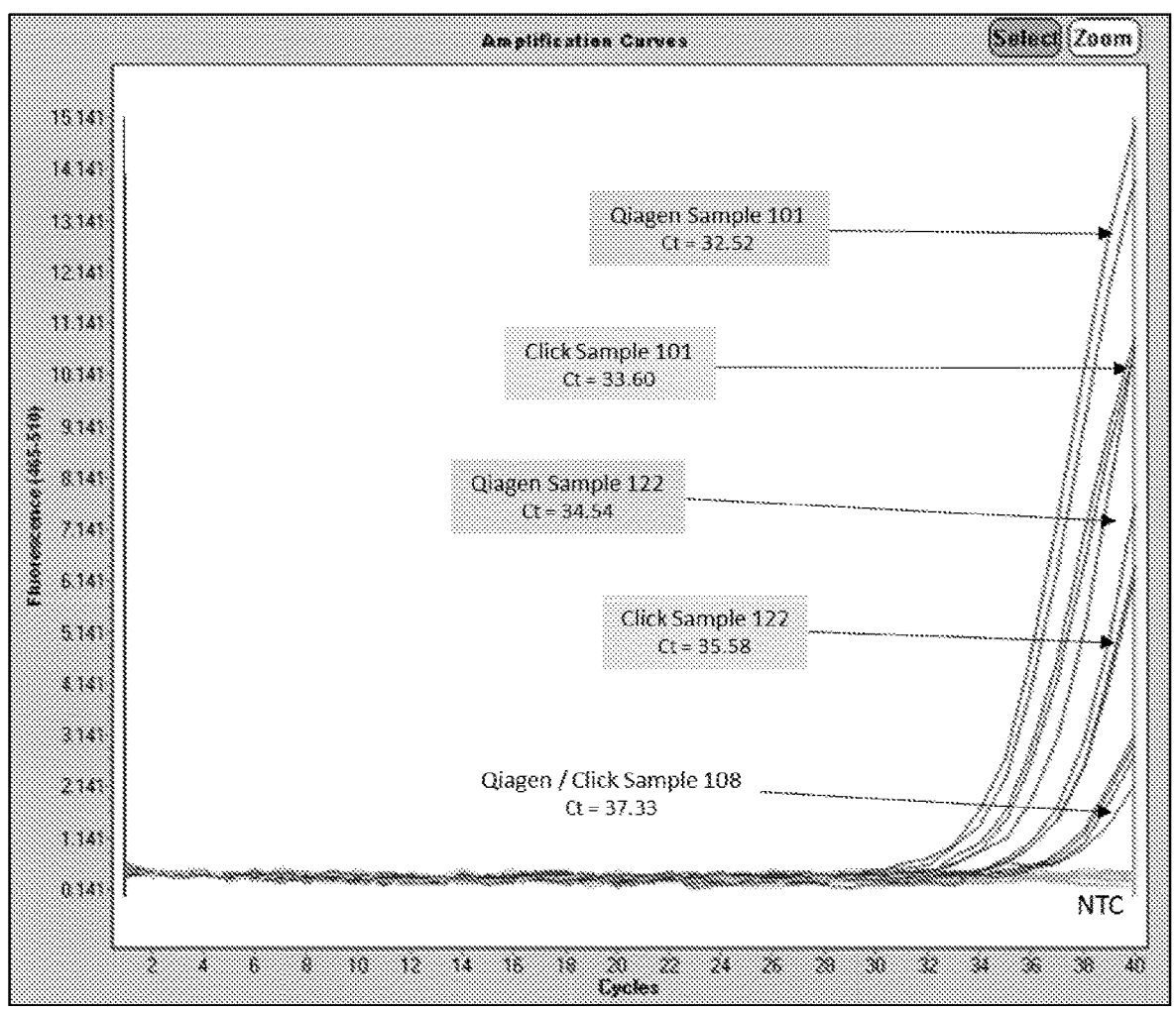
FIG. 5 depicts a comparison of data generated from a real-time PCR reaction performed on DNA extracted from a clinical sample positive for both *N. gonorrhoeae* and *C. trachomatis* (Sample 122), a clinical samples positive for *C. trachomatis* (Samples 101 and 108) utilizing the methods provided herein versus standard DNA extraction methods.
Figure 6:
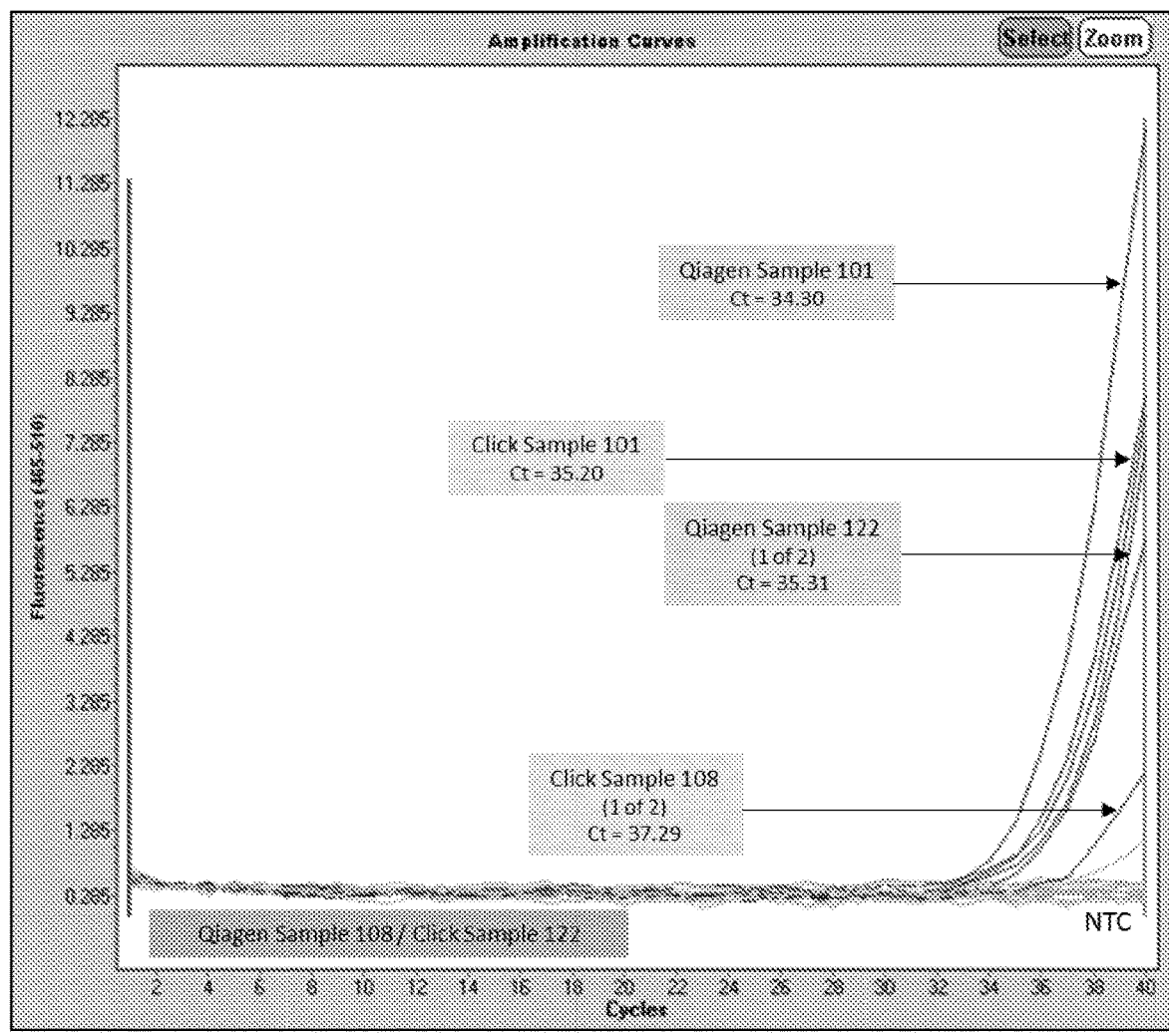
FIG. 6 depicts a comparison of data generated from a real-time PCR reaction performed on DNA extracted from a clinical sample positive for both *N. gonorrhoeae* and *C. trachomatis* (Sample 122) and clinical samples positive for *C. trachomatis* (Samples 101 and 108) utilizing the methods provided herein versus standard DNA extraction methods.

FIGS. 5 and 6 depict a comparison of data generated from real-time PCR reactions performed on DNA extracted from a clinical sample positive for both *N. gonorrhoeae* and *C. trachomatis* (Sample 122), and clinical samples positive for *C. trachomatis* (Samples 101 and 108) utilizing the methods provided herein versus standard DNA extraction methods. Both standard ("Qiagen") and new methods ("Click") of DNA extraction did not detect the presence of *C. trachomatis* in Sample 105 using either Primer Set #3 or Primer Set #4. Primer Set #3 was able to detect the presence of *C. trachomatis* in Samples 108, 122 and 101 using either sample preparation method (FIG. 5). Primer Set #4 was able to detect the presence of *C. trachomatis* in Sample 101 for both sample preparation methods, and only Sample 122 for the standard method, and only Sample 108 for the new method (FIG. 6).

Figure 7:
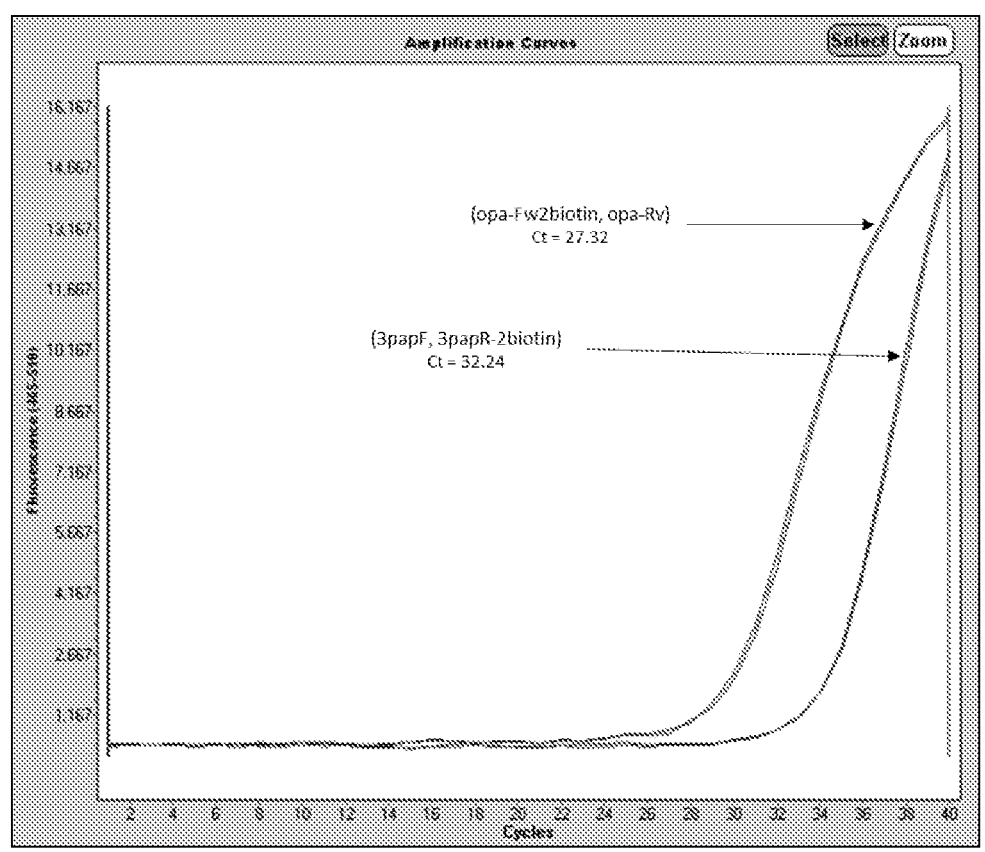
FIG. 7 depicts a comparison of data generated from a real-time PCR reaction performed on *N. gonorrhoeae* DNA utilizing different sets of primers.
Figure 8:
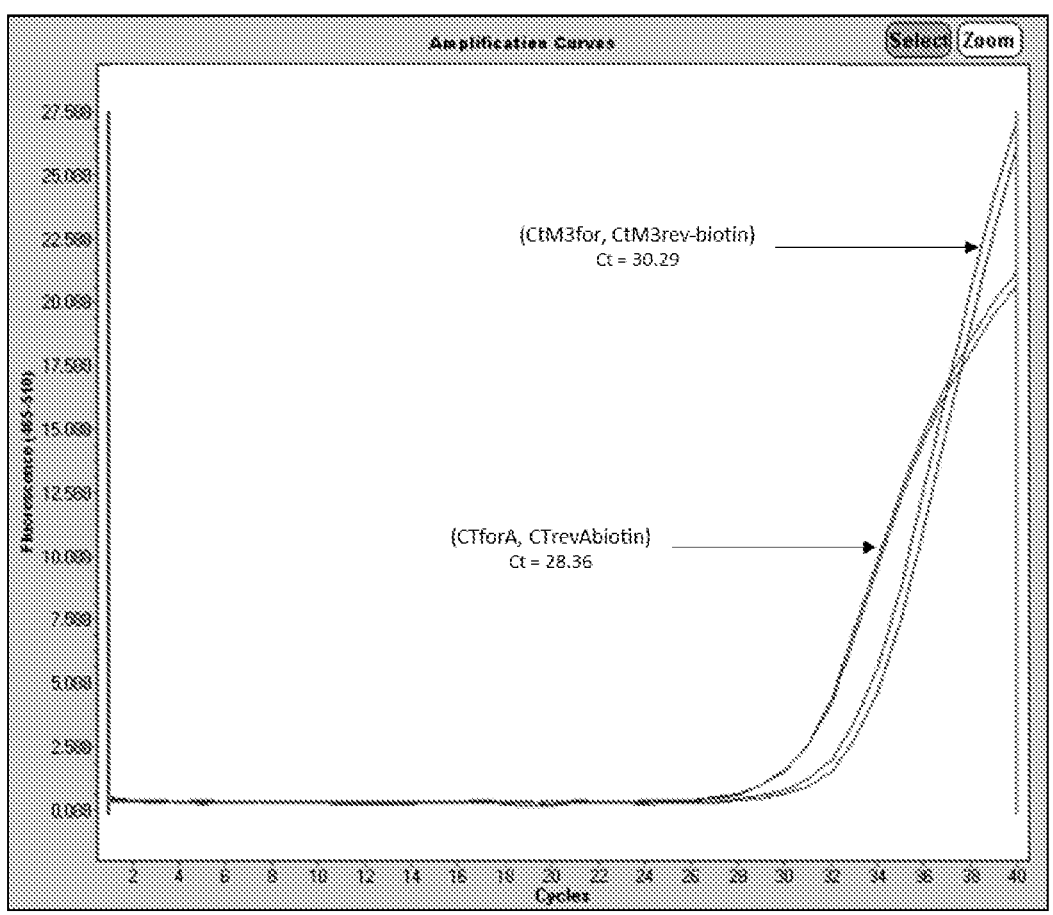
FIG. 8 depicts a comparison of data generated from a real-time PCR reaction performed on *C. trachomatis* DNA utilizing different sets of primers.

FIGS. 7 and 8 depict a comparison of data generated from real-time PCR reactions performed on *N. gonorrhoeae* positive control DNA or *C. trachomatis* positive control DNA, respectively, utilizing different sets of primers.

Figure 9:
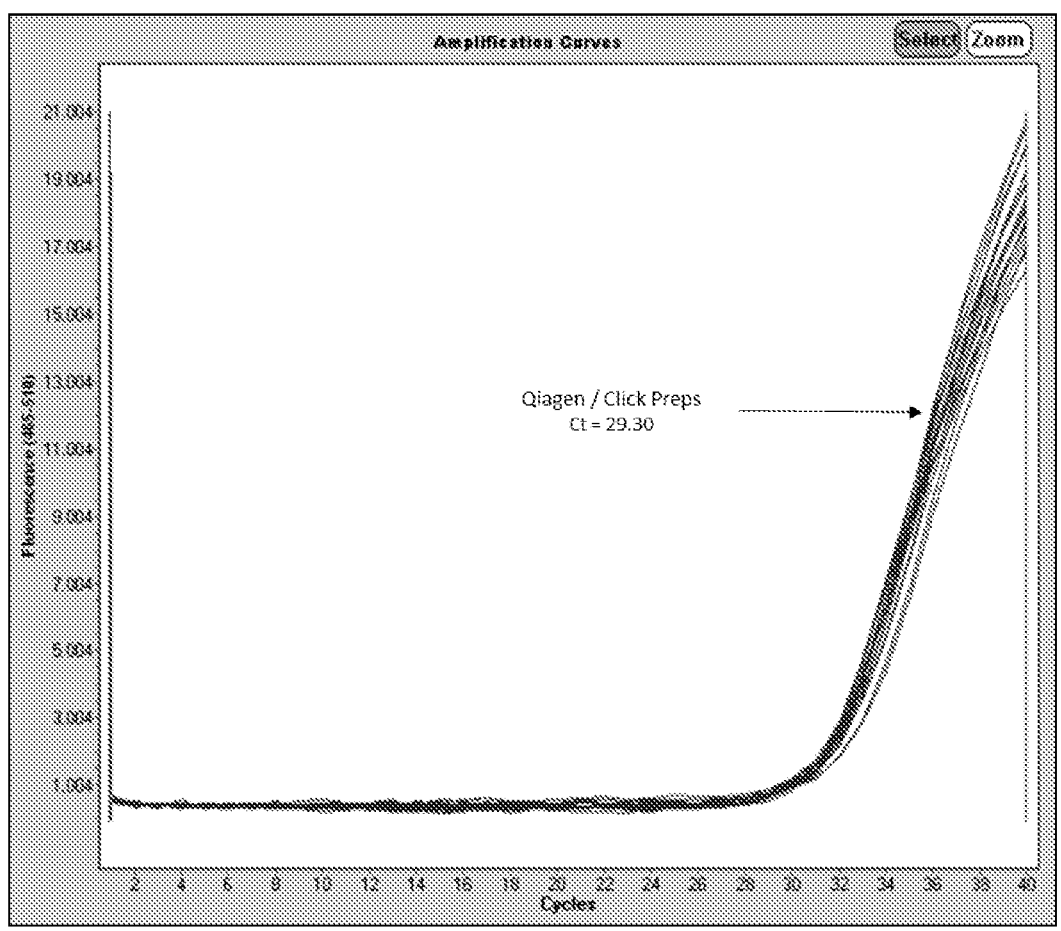
FIG. 9 depicts data generated from a real-time PCR reaction performed on *N. gonorrhoeae* DNA spiked into a sample and PCR mixture to test for sample inhibition.

FIG. 9 depicts data generated from a real-time PCR reaction performed on *N. gonorrhoeae* DNA spiked into a sample and PCR mixture to test for sample inhibition.

Example 2

PCR Amplification from Samples Purified Without a Filter Step

In this example DNA was purified from a range of samples using the no filter method described herein. Briefly samples are flowed into the holding chamber of the inactivation module. The heat-treated fluid is flowed through the serpentine path and into a mixing chamber containing PCR reagents. PCR is performed and PCR products are detected. In this example, purified DNA is subjected to PCR using the probe sets of example 1.

FIG. 25 shows successful PCR amplification from DNA isolated from 19 different clinical samples, shown in Table 2, using this method.

TABLE 2

Samples used in FIG. 25

| Condition | Sample | Dilution factor |
|---|---|---|
| 1 | Positive Control | No dilution |
| 2 | 100 | No dilution |
| 3 | 101 | No dilution |
| 4 | 103 | No dilution |
| 5 | 104 | No dilution |
| 6 | 108 | No dilution |
| 7 | 110 | No dilution |
| 8 | 112 | No dilution |
| 9 | 113 | No dilution |
| 10 | 114 | No dilution |
| 11 | 118 | No dilution |
| 12 | 119 | No dilution |
| 13 | 121 | No dilution |
| 14 | 122 | No dilution |
| 15 | 123 | No dilution |
| 16 | 125 | No dilution |
| 17 | 126 | No dilution |
| 18 | 127 | No dilution |

TABLE 2-continued

Samples used in FIG. 25

| Condition | Sample | Dilution factor |
|---|---|---|
| 19 | 106 | No dilution |
| 20 | 171 | No dilution |
| 21 | Positive Control | 1:3 |
| 22 | 100 | 1:3 |
| 23 | 101 | 1:3 |
| 24 | 103 | 1:3 |
| 25 | 104 | 1:3 |
| 26 | 108 | 1:3 |
| 27 | 110 | 1:3 |
| 28 | 112 | 1:3 |
| 29 | 113 | 1:3 |
| 30 | 114 | 1:3 |
| 31 | 118 | 1:3 |
| 32 | 119 | 1:3 |
| 33 | 121 | 1:3 |
| 34 | 122 | 1:3 |
| 35 | 123 | 1:3 |
| 36 | 125 | 1:3 |
| 37 | 126 | 1:3 |
| 38 | 127 | 1:3 |
| 39 | 106 | 1:3 |
| 40 | 171 | 1:3 |

Figure 26:
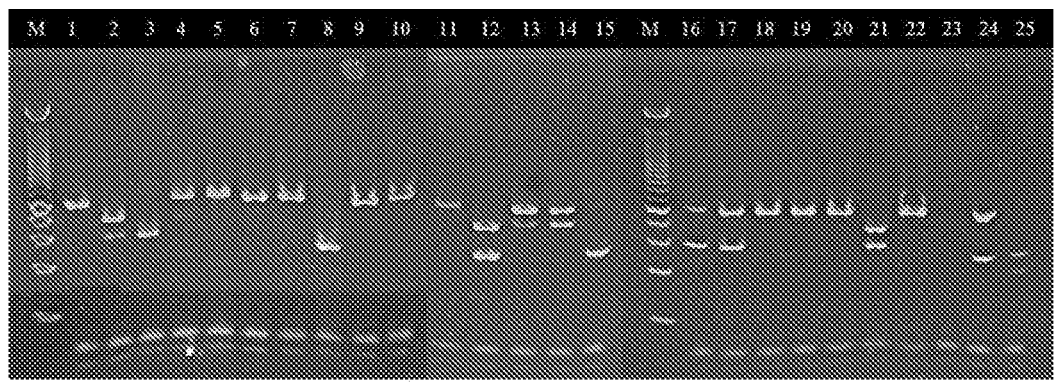
FIG. 26 illustrates the results of a PCR reaction performed upon DNA extracted using the methods of this disclosure.

FIG. 26 shows the results of PCR amplification on DNA extracted from the samples in Table 3. Samples in Table 2 were purified in buffer comprising 50 mM Tris pH 8.4, Tween-80, 2% (w/v), BSA, 0.25% (w/v), Proclin 300 0.03% (w/v), and Antifoam SE-15, 0.002% (v/v) made up in purified water, (TT buffer). Amplification was seen in every sample indicating that the PCR reaction possesses high tolerance to inhibitors.

TABLE 3

Samples used in FIG. 26

| Condition | Sample | Microorganism present |
|---|---|---|
| 1 | Control NS cells | NS |
| 2 | 97 | |
| 3 | 170 | NG |
| 4 | 172 | CT |
| 5 | 174 | NS |
| 6 | 175 | NS |
| 7 | 176 | NS |
| 8 | 177 | TV |
| 9 | 178 | NS |
| 10 | 179 | NS |
| 11 | 180 | NS |
| 12 | 271 | CT |
| 13 | 272 | CT |
| 14 | 273 | CT |
| 15 | 285 | NG |
| 16 | 288 | NG |
| 17 | 289 | NG |
| 18 | 340 | NS |
| 19 | 341 | NS |
| 20 | 342 | NS |
| 21 | 109 | |
| 22 | Control NS cells | NS |
| 23 | Control NS cells | NS |
| 24 | PCR positive control | |
| 25 | No template control | |

FIG. 26 depicts the result of an experiment comparing different sample buffers. The sample buffers used were the TT buffer described above, MSwab buffer (MS; Copan Diagnostics, CA), and Liquid Amies Buffer (LA; Copan Diagnostics, CA). PCR products were run on 4% agarose gels to determine the success of the PCR reaction. Samples rehydrated in TT buffer amplified as expected, equal to the controls. The other two medias MS and LA showed varying results, suggesting variable inhibition of the PCR by contaminants from the sample buffer.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The devices and methods described herein are not limited to performing a molecular diagnostic test on human samples. In some embodiments, any of the devices and methods described herein can be used with veterinary samples, food samples, and/or environmental samples.

Although the fluid transfer assemblies are shown and described herein as including a piston pump (or syringe), in other embodiments, any suitable pump can be used. For example, in some embodiments any of the fluid transfer assemblies described herein can include any suitable positive-displacement fluid transfer device, such as a gear pump, a vane pump, and/or the like.

What is claimed is:

1. A method of nucleic acid extraction, comprising:
   (a) conveying a biological sample into a sample input module of a molecular diagnostic test device; and
   (b) actuating the molecular diagnostic test device to:
   (c) convey the biological sample from the sample input module to a lysing module, the lysing module including a heater and defining a first reaction volume and a second reaction volume;
   (d) maintain an input solution containing the biological sample and a lysis buffer within the first reaction volume to lyse at least a portion of the biological sample thereby extracting a plurality of nucleic acid molecules;
   (e) activate the heater to heat a portion of the lysing module to produce an inactivation temperature zone within the second reaction volume; and
   (f) produce a flow of the input solution within the second reaction volume such that a volume of the input solution is heated within the inactivation temperature zone to inactivate an enzyme within the input solution.

2. The method of claim 1, wherein the volume of the input solution is at least 10 microliters.

3. The method of claim 1, wherein:
   (a) the first reaction volume is in fluid communication with the second reaction volume; and
   (b) the lysing module defines a vent opening into the first reaction volume.

4. The method of claim 3, wherein:
   (a) the volume of the input solution is heated to an inactivation temperature of about 95 degrees Celsius; and
   (b) the input solution within the first reaction volume contains at least one of a salt or a sugar to raise a boiling temperature of the input solution.

5. The method of claim 1, wherein the portion of the lysing module is a second portion, the actuating the molecular diagnostic test device further causes the molecular diagnostic test device to:
(a) heat a first portion of the lysing module to produce a lysing temperature zone within the second reaction volume, the flow of the input solution within the second reaction volume being such that the volume of the input solution is heated within the lysing temperature zone to lyse a biological entity within the volume of the input solution.

6. The method of claim 1, wherein the plurality of nucleic acid molecules includes DNA, the DNA being extracted from the biological sample with a A260/A280 ratio of at least 1.5.

7. The method of claim 1, wherein the actuating the molecular diagnostic test device includes moving a sample actuator to produce a pressure within the sample input module to convey the biological sample from the sample input module towards the lysing module.

8. The method of claim 7, wherein the sample actuator is a non-electronic actuator.

9. The method of claim 8, wherein the actuating the molecular diagnostic test device further causes the molecular diagnostic test device to:
(a) receive an electronic signal from a sensor within the lysing module, the electronic signal indicating the presence of the input solution within the first reaction volume; and
(b) activate the heater in response to the electronic signal.

10. The method of claim 1, wherein the actuating the molecular diagnostic test device further causes the molecular diagnostic test device to:
(a) heat a portion of an amplification module within the molecular diagnostic test device to amplify a nucleic acid from the plurality of nucleic acid molecules to produce an output containing a target amplicon; and
(b) convey the output to a detection module of the molecular diagnostic test device.

11. The method of claim 10, further comprising:
(a) viewing a visible signal indicating a presence of the target amplicon; and
(b) discarding, after the viewing, the molecular diagnostic test device.

12. The method of claim 3, wherein the volume of the input solution is heated to an inactivation temperature of between about 92° C. and about 98° C.

13. The method of claim 1, wherein the volume of the input solution is between 10 microliters and 10 milliliters.

14. The method of claim 3, wherein the input solution within the first reaction volume contains at least one of a salt or a sugar to raise a boiling temperature of the input solution.

15. The method of claim 1, wherein the molecular diagnostic test device is devoid of a filter.

16. The method of claim 1, wherein:
the molecular diagnostic test device further includes an amplification module and a detection module; and
the actuating the molecular diagnostic test device further causes the molecular diagnostic test device to:
convey the input solution to the amplification module;
heat the input solution within the amplification module to amplify a nucleic acid from the plurality of nucleic acid molecules to produce an output containing a target amplicon; and
convey the output to the detection module of the molecular diagnostic test device to react the target amplicon with a detection reagent to produce a signal that indicates a presence of the target amplicon.

17. The method of claim 16, further comprising:
reading, via an exterior of the housing, a result associated with the signal; and
discarding, after the reading, the molecular diagnostic test device.

* * * * *

UNITED STATES PATENT AND TRADEMARK OFFICE
CERTIFICATE OF CORRECTION

| | | |
|---|---|---|
| PATENT NO. | : 11,193,119 B2 | Page 1 of 1 |
| APPLICATION NO. | : 16/186240 | |
| DATED | : December 7, 2021 | |
| INVENTOR(S) | : Swenson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 355 days.

Signed and Sealed this
Twenty-fifth Day of February, 2025

Coke Morgan Stewart
*Acting Director of the United States Patent and Trademark Office*